(12) United States Patent
Frank et al.

(10) Patent No.: US 7,973,072 B2
(45) Date of Patent: Jul. 5, 2011

(54) SUBSTITUTED BENZO-CONDENSED CYCLOHEXANONE DERIVATIVES AND THE USE THEREOF FOR MEDICAMENT PRODUCTION

(75) Inventors: Robert Frank, Aachen (DE); Michael Przewosny, Aachen (DE); Ruth Jostock, Stolberg (DE)

(73) Assignee: Gruenenthal GmbH, Aachen (DE)

( * ) Notice: Subject to any disclaimer, the term of this patent is extended or adjusted under 35 U.S.C. 154(b) by 766 days.

(21) Appl. No.: 11/915,129

(22) PCT Filed: May 17, 2006

(86) PCT No.: PCT/EP2006/004654
§ 371 (c)(1),
(2), (4) Date: Nov. 20, 2007

(87) PCT Pub. No.: WO2006/122771
PCT Pub. Date: Nov. 23, 2006

(65) Prior Publication Data
US 2008/0161352 A1    Jul. 3, 2008

(30) Foreign Application Priority Data

May 20, 2005  (DE) .................. 10 2005 024 013
Aug. 17, 2005  (DE) .................. 10 2005 039 145

(51) Int. Cl.
*A61K 31/382* (2006.01)
*C07D 335/06* (2006.01)
(52) U.S. Cl. ........................ 514/432; 549/23
(58) Field of Classification Search ............. 549/23; 514/432
See application file for complete search history.

(56) References Cited

FOREIGN PATENT DOCUMENTS

| CN | 1147514 A | 4/1997 |
|----|-----------|--------|
| CN | 1394858 A | 2/2003 |
| DE | 1 913 199 | 9/1970 |
| DE | 2 018 097 | 10/1970 |
| EP | 0 496 342 A1 | 7/1992 |
| EP | 0 567 138 A2 | 10/1993 |
| GB | 1 218 778 | 1/1971 |
| WO | WO 97/23202 A1 | 7/1997 |

OTHER PUBLICATIONS

Qi, Ping et al., "Synthesis and antifungal activities of Mannich bases of thiochromanones", Zhongguo Yaowu Huaxue Zazhi, vol. 13, No. 3, pp. 134-137, 2003, XP009078734.
Zhu, Quanhong at al., "Synthesis and antifungal activities of mannich bases of thiochromanone derivatives", Zhongguo Yaowu Huaxue Zazhi, vol. 10, No. 1, pp. 1-4, 2000, XP009078763.
Fang, Lin et al., "Studies on the synthesis and antifungal activity of thiochromanone derivatives", Chinese Chemical Letters, vol. 8, No. 11, pp. 939-942, 1997, XP009078733.
Venturelli, Paola et al., "Molecular modelling and quantitative structure-activity relationship analysis using theoretical descriptors of 1,4-benzodioxan (WB-4101) related compounds .alpha.1-adrenergic antagonists", The Ochem, 95, pp. 327-340, 1992, XP009078735.
Pigini, Maria et al., "Structure-activity relationships in 1,4-benzodioxan-related compounds. Investigation on the role of the dehydrodioxane ring on .alpha.1-adrenoreceptor blocking activity", Journal of Medicinal Chemistry, 31(12), 2300-4, 1988, XP002123239.
Maiti, Swaraj B. et al., "Effect of remote heteroatoms and nature of the reducing agents on the stereochemical course of reductions of the carbon-nitrogen . pi.-bond of a new class of tetrahydropyridines", Journal of the Chemical Society, Perkin Transaction 1: Organic and Bioorganic Chemistry, (1972-1999), vol. 3, p. 611-21, CODEN: JCPRB$; ISSN 0300-922X, 1998, XP009078775.
Benthe, H. F. et al., "Noradrenaline-antagonistic activity of some phenylethylamine and phenoxyethylamine derivatives", Arzneimittelforschung, vol. 22, No. 9, pp. 1468-1474, 1972, XP009078776.
Mirsha, A. et al., "Amebicides derived from chromanones and thiochromanones", Journal of the Institution of Journal of the Institution of Chemists, (India), vol. 42, No. 6, pp. 223-225, 1970, XP009078722.
Kaushiva, B. S., "Antiamebic action of substituted quinolines, quinaldines, quinazolines, quinazolones, chromanones, thiochromanones, diaminoalkanes, benzylamines, and cresols", Ann. Biochem. Exptl. Med. (Calcutta), Suppl. vol. 20, pp. 493-504, 1960, XP009078721.
Chu, Sae-Lee et al., "The preparation of the derivatives of 3-dialkylaminomethylthiachroman-4-ones", Huaxue Xuebao, vol. 22, pp. 371-378, 1956, XP009078727.
Sen, A. B. et al., "Possible antiamebic agents. V. Mannich bases from substituted thiochromanones", J. Indian Chem. Soc., vol. 35, pp. 197-201, 1958, XP009078723.
Sen, A. B. et al., "Possible antiamebic agents. III. Mannich bases from thiachroman-4-ones", J. Indian Chem. Soc., 34, pp. 687-690, 1957, XP009078724.
Wiley, Paul F., "Amebacidal chromanones" Journal of the American Chemical Society, vol. 73, pp. 4205-4209, 1951, XP009078729.
Turner et al., J. Am. Chem. Soc., vol. 78, 1956, pp. 5923-5926, XP009078884.
Nangia, A. et Bheema Rao, P.: Tetrahedron Letters, vol. 33, No. 17, 1992, pp. 2375-2378, XP009078885.
Boger, D. L. et Mathvink, R. J.: J. Org. Chem., vol. 57, No. 5, 1992, pp. 1429-1443, XP009078883.
Andrisano et al.: J. Chromatogr., vol. 803, 1998, pp. 189-195, XP004117832.
Ninagawa, A. et al., "The Acid-catalyzed Reactions of 4-Chromanones with Formalehyde", Bulletine of the Chemical Society of Japan, vol. 52 (4), pp. 1169-1173, (1979).
Katritzky, A. R., et al., "Benzotriazole-assisted Synthesis of Novel Mannich Bases from Ketones and Diverse Aldehydes", Tetrahedron, vol. 46, No. 3, 1990.
International Search Report dated Apr. 24, 2007 including English translation of the relevant portion (Twenty (20) pages).
PCT/IPEA/409 with English translation (Thirteen (13) pages), (2008).

(Continued)

Primary Examiner — Bernard Dentz
(74) Attorney, Agent, or Firm — Crowell & Moring LLP

(57) ABSTRACT

The invention relates to substituted benzo-condensed cyclohexanone derivatives, to a method for the production thereof, to medicaments containing said derivatives and to the use of the inventive compounds for producing medicaments.

15 Claims, No Drawings

OTHER PUBLICATIONS

German Search Report dated Feb. 13, 2006 including English translation (Ten (10) pages).

L. C. Hendershot et al., "Antagonism of the Frequency of Phenlyquinone-Induced Writhing in the Mouse by Weak Analgesics and Nonanalgesics", The Biochemical Reasearch Laboratory, Sep. 19, 1958, pp. 237-240, vol. 125.

David Dubuisson et al., "The Formalin Test: A Quantitative Study of the Analgesic Effects of Morphine, Meperidine, and Brain Stem Stimulation in Rats and Cats", Pain, Department of Psychology, McGill University, 1977, vol. 4, pp. 161-174.

Terence J Coderre et al., "Contribution of Central Neuroplasticity to Pathological Pain: Review of Clinical and Experimental Evidence", Pain, Review Article, vol. 52, 1993, pp. 259-285.

I.C. Hendershot et al., "Antagonism of the Frequency of Phenlyquinone-Induced Writhing in the Mouse by Weak Analgesics and Nonanalgesics," J. Pharmacol. Exp. Ther., The Biochemical Research Laboratory, 1959, vol. 125, pp. 237-240.

Louis J Ravin, " Performulation," Remington's Pharmaceutical Sciences, editor A.R. Gennaro, 17th edition, Mack Publishing Company, Easton, PA, 1985, Pharmaceutics Department, SmithKline Beckman Corporation, pp. 1409-1423, Chapter 76.

Anthony R Disanto, "Bioavailability and Bioequivalency Testing," Remington's Pharmaceutical Sciences, editor A.R. Gennaro, 17th edition, Mack Publishing Company, Easton, PA, 1985, Clinical Biopharmaceutics/New Formulation Development, The Upjohn Company, pp. 1424-1431, Chapter 77.

Adelbert M Knevel, Remington's Pharmaceutical Sciences, editor A.R. Gennaro, 17th edition, Mack Publishing Company, Easton, PA, 1985, "Separation," School of Pharmacy and Pharmacal Sciences Purdue University, pp. 1432-1442, Chapter 78.

G Briggs Phillips, "Sterilization," Remington's Pharmaceutical Sciences, editor A.R. Gennaro, 17th edition, Mack Publishing Company, Easton, PA, 1985, Health Industries manufacturers Association, pp. 1443-1454, Chapter 79.

Frederick p. Siegel, "Tonicity, Osmoticity, Osmolality and Osmolarity," Remington's Pharmaceutical Sciences, editor A.R. Gennaro, 17th edition, Mack Publishing Company, Easton, PA, 1985, College of Pharmacy, University of Illinois, pp. 1455-1472, Chapter.

Robert L. Giles, et al., "Plastic Packaging Materials," Remington's Pharmaceutical Sciences, editor A.R. Gennaro, 17th edition, Mack Publishing Company, Easton, PA, 1985, Glenn Beall Engineering, Inc. et al, pp. 1473-1477, Chapter 81.

Carl J. Lintner, "Stability of Pharmaceutical Products," Remington's Pharmaceutical Sciences, editor A.R. Gennaro, 17th edition, Mack Publishing Company, Easton, PA, 1986, Lintner Associates, pp. 1478-1486, Chapter 82.

Clyde R Erskine, "Quality Assurance and Control," Remington's Pharmaceutical Sciences, editor A.R. Gennaro, 17th edition, Mack Publishing Company, Easton, PA, 1985, SmithKline Beckman Corporation, pp. 1487-1491, Chapter 83.

J G Nairn, "Solutions, Emulsions, Suspensions and Extractives," Remington's Pharmaceutical Sciences, editor A.R. Gennaro, 17th edition, Mack Publishing Company, Easton, PA, 1985, Faculty of Pharmacy, University of Toronto, pp. 1492-1517, Chapter 84.

Kenneth E Avis, "Parenteral Preparations," Remington's Pharmaceutical Sciences, editor A.R. Gennaro, 17th edition, Mack Publishing Company, Easton, PA, 1985, College of Pharmacy, University of Tennessee Center for the health Sciences, pp. 1518-1541, Chapter 85.

Salvatore J Turco, et al., "Intravenous Admixtures," Remington's Pharmaceutical Sciences, editor A.R. Gennaro, 17th edition, Mack Publishing Company, Easton, PA, 1985, Temple University School of Pharmacy et al., pp. 1542-1553, Chapter 86.

John D Mullins, "Ophthalmic Preparations," Remington's Pharmaceutical Sciences, editor A.R. Gennaro, 17th edition, Mack Publishing Company, Easton, PA, 1985, Research and Development Alcon Laboratories. pp. 1553-1566, Chapter 87.

Lawrence H Block, "Medicated Applications," Remington's Pharmaceutical Sciences, editor A.R. Gennaro, 17th edition, Mack Publishing Company, Easton, PA, 1985, Duquesne University School of Pharmacy, pp. 1567-1584, Chapter 88.

Edward G Ripple, "Powders," Remington's Pharmaceutical Sciences, editor A.R. Gennaro, 17th edition, Mack Publishing Company, Easton, PA, 1985, College of Pharmacy, University of Minnesota, pp. 1585-1602, Chapter 89.

Robert E King et al., "Oral Solid Dosage Forms," Remington's Pharmaceutical Sciences, editor A.R. Gennaro, 17th edition, Mack Publishing Company, Easton, PA, 1985, Philadelphia College of Pharmacy and Science, pp. 1603-1632, Chapter 90.

Stuart C Porter, "Coating of Pharmaceutical Dosage Forms," Remington's Pharmaceutical Sciences, editor A.R. Gennaro, 17th edition, Mack Publishing Company, Easton, PA. 1985. Colorcon. Inc., pp. 1633-1643, Chapter 91.

Mark A Longer et al., "Sustained-Release Drug Delivery Systems," Remington's Pharmaceutical Sciences, editor A.R. Gennaro, 17th edition, Mack Publishing Company, Easton, PA, 1985, School of Pharmacy, University of Wisconsin, pp. 1644-1661, Chapter 92.

John J Sclarra et al., "Aerosols," Remington's Pharmaceutical Sciences, editor A.R. Gennaro, 17th edition, Mack Publishing Company, Easton, PA, 1985, Arnold & Marie Schwartz College of Pharmacy and Health Sciences, pp. 1662-1677, Chapter 93.

SUBSTITUTED BENZO-CONDENSED CYCLOHEXANONE DERIVATIVES AND THE USE THEREOF FOR MEDICAMENT PRODUCTION

The present invention relates to substituted benzofused cyclohexanone derivatives, to processes for their preparation, to medicaments comprising these compounds and to the use of these compounds for producing medicaments.

The treatment of pain, especially of neuropathic pain, has great significance in medicine. There is a global demand for effective pain therapies. The urgent need for research into patient-oriented and targeted treatment of chronic and non-chronic states of pain, which is understood to mean the successful and satisfactory treatment of pain for the patient, is also documented in a large number of scientific studies which have recently appeared in the field of applied analgesics and fundamental research into nociception.

A suitable starting point for the treatment of pain, especially of neuropathic pain, is the vanilloid receptor of subtype 1 (VR1/TRPV1), which is frequently also referred to as the capsaicin receptor. This receptor is stimulated, inter alia, by vanilloids, for example capsaicin, heat and protons, and plays a central role in the development of pain. Furthermore, it is of significance for a multitude of further physiological and pathophysiological processes, for example migraines; depressions; neurodegenerative disorders; cognitive disorders; states of anxiety; epilepsy; coughing; diarrhea; pruritus; disorders of the cardiovascular system; disorders of food uptake; medicament dependence; medicament abuse and especially urine incontinence.

It was therefore an object of the present invention to provide novel compounds which are suitable especially as active pharmaceutical ingredients in medicaments, preferably in medicaments for the treatment of disorders or diseases which are mediated at least partly by vanilloid receptors 1 (VR1/TRPV1 receptors).

It has now been found that, surprisingly, substituted benzofused cyclohexanone derivatives of the general formula I specified below are suitable for treating pain and have an excellent affinity for the vanilloid receptor of subtype I (VR1/TRPV1 receptor). Furthermore, these inventive benzofused cyclohexanone derivatives also exhibit a high affinity for cannabinoid receptors CB1 (CB1 receptors) and/or cannabinoid receptors CB2 (CB2 receptors). The inventive benzofused cyclohexanone compounds are therefore suitable especially for prophylaxis and/or treatment of disorders or diseases which are mediated at least partly by vanilloid receptors 1 (VR1/TRPV1) and/or cannabinoid receptors CB1 (CB1 receptors) and/or cannabinoid receptors CB2 (CB2 receptors).

The present invention therefore provides substituted benzofused cyclohexanone derivatives of the general formula I

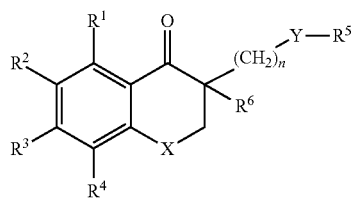

I in which
n is 1, 2 or 3;
X is $CH_2$, O, S, S(=O), $S(=O)_2$, N(H), $N(R^7)$, $N[C(=O)—R^8]$ or $N[C(=O)—O—R^9]$;

Y is O, O—C(=O), O—C(=O)—O, O—S(=O)$_2$, O—C(=O)—N(H), O—C(=S)—N(H), N(H), N(H)—C(=O)—N(H) or N(H)—C(=S)—N(H); where the free atom which binds to the $R^5$ radical is always stated last; with the proviso that Y is not N(H) when $R^6$ is simultaneously a hydrogen radical, $R^1$, $R^2$, $R^3$ and $R^4$ are each independently
  H, F, Cl, Br, I, —SF$_5$, —CN, —NC, —NO$_2$, —SO$_3$H, —NH$_2$, —OH, —SH,
  —OR$^{10}$, —SR$^{11}$, —NR$^{12}$R$^{13}$, —NH—R$^{14}$, —NH—C(=O)—R$^{15}$, —NR$^{16}$—C(=O)—R$^{17}$, —C(=O)—NH$_2$, —C(=O)—NH—R$^{18}$, —C(=O)—NR$^{19}$R$^{20}$, —C(=O)—H, —C(=O)—R$^{21}$, —C(=O)—OH, —C(=O)—OR$^{22}$, —O—C(=O)—R$^{23}$ or a linear or branched, saturated or unsaturated, unsubstituted or at least monosubstituted aliphatic radical;

$R^5$ is a —C(=O)—R$^{26}$ group;
  is a —S(=O)$_2$—R$^{27}$ group;
  is a linear or branched, saturated or unsaturated, unsubstituted or at least monosubstituted aliphatic radical;
  is an unsubstituted or at least monosubstituted, unsaturated or saturated cycloaliphatic radical optionally having at least one heteroatom as a ring member; which may be bonded via a linear or branched, unsubstituted or at least monosubstituted alkylene, alkenylene or alkynylene group;
  or an unsubstituted or at least monosubstituted aryl or heteroaryl radical which may be bonded via a linear or branched, unsubstituted or at least monosubstituted alkylene, alkenylene or alkynylene group, and/or fused to an unsubstituted or at least monosubstituted mono- or polycyclic ring system;
  with the proviso that $R^5$ is not a linear or branched, saturated or unsaturated, unsubstituted or at least monosubstituted aliphatic radical when $R^6$ is simultaneously a hydrogen radical or is —(CH$_2$)$_q$—O—R$^{24}$ in which q=1, 2 or 3 and $R^{24}$ is a linear or branched, saturated or unsaturated, unsubstituted or at least monosubstituted aliphatic radical;

$R^6$ is a hydrogen radical;
  is —(CH$_2$)$_p$—Z—R$^{24}$ where p=1, 2 or 3;
  or is —(CH$_2$)$_q$—OR$^{25}$ where q=1, 2 or 3;

$R^7$, $R^8$ and $R^9$ are each independently
  a linear or branched, saturated or unsaturated, unsubstituted or at least monosubstituted aliphatic radical;
  or an unsubstituted or at least monosubstituted aryl or heteroaryl radical which is bonded via a linear or branched, unsubstituted or at least monosubstituted alkylene, alkenylene or alkynylene group;

$R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{26}$, $R^{27}$, $R^{28}$ and $R^{29}$ are each independently
  a linear or branched, saturated or unsaturated, unsubstituted or at least monosubstituted aliphatic radical;
  an unsubstituted or at least monosubstituted, unsaturated or saturated cycloaliphatic radical optionally having at least one heteroatom as a ring member;
  or an unsubstituted or at least monosubstituted aryl or heteroaryl radical which may be bonded via a linear or branched, unsubstituted or at least monosubstituted alkylene, alkenylene or alkynylene group and/or may be fused to an unsubstituted or at least monosubstituted mono- or polycyclic ring system;

Z is O, O—C(=O), O—C(=O)—O, O—S(=O)$_2$, O—C(=O)—N(H), O—C(=S)—N(H), N(H), N(H)—C(=O)—N(H) or N(H)—C(=S)—N(H); where the free atom which binds to the $R^{24}$ radical is always stated last;

$R^{24}$ is a —C(=O)—$R^{28}$ group;
is a —S(=O)$_2$—$R^{29}$ group;
is a linear or branched, saturated or unsaturated, unsubstituted or at least monosubstituted aliphatic radical;
is an unsubstituted or at least monosubstituted, unsaturated or saturated cycloaliphatic radical which optionally has at least one heteroatom as a ring member and may be bonded via a linear or branched, unsubstituted or at least monosubstituted alkylene, alkenylene or alkynylene group;
or is an unsubstituted or at least monosubstituted aryl or heteroaryl radical which may be bonded via a linear or branched, unsubstituted or at least monosubstituted alkylene, alkenylene or alkynylene group and/or may be fused to an unsubstituted or at least monosubstituted mono- or polycyclic ring system;
and
$R^{25}$ is a hydrogen radical;
in each case, as appropriate, in the form of one of their pure stereoisomers, especially enantiomers or diastereomers, of its racemates or in the form of a mixture of stereoisomers, especially of the enantiomers and/or diastereomers, in any mixing ratio, or in each case in the form of corresponding salts, or in each case in the form of corresponding solvates,
excluding the compounds
(1-oxo-1,2,3,4-tetrahydronaphthalene-2,2-diyl)bis(methylene)bis(4-methoxybenzoate),
(4-oxochroman-3,3-diyl)bis(methylene)bis(4-methoxybenzoate),
(4-oxothiochroman-3,3-diyl)bis(methylene)bis(4-methoxybenzoate),
(4-oxothiochroman-3,3-diyl)bis(methylene)bis(2,4-dichlorobenzoate),
(4-oxochroman-3,3-diyl)bis(methylene)bis(2,4-dichlorobenzoate),
(1-oxo-1,2,3,4-tetrahydronaphthalene-2,2-diyl)bis(methylene)bis(2,4-dichlorobenzoate),
(4-oxochroman-3,3-diyl)bis(methylene)bis(3-(trifluoromethyl)benzoate),
(4-oxothiochroman-3,3-diyl)bis(methylene)dibenzoate,
(4-oxothiochroman-3,3-diyl)bis(methylene)bis(trifluoromethyl)benzoate),
(4-oxochroman-3,3-diyl)bis(methylene)dibenzoate,
(1-oxo-1,2,3,4-tetrahydronaphthalene-2,2-diyl)bis(methylene)bis(3-(trifluoromethyl)benzoate),
(1-oxo-1,2,3,4-tetrahydronaphthalene-2,2-diyl)bis(methylene)dibenzoate,
(7-methoxy-4-oxochroman-3,3-diyl)bis(methylene)diacetate,
(7-acetoxy-4-oxochroman-3,3-diyl)bis(methylene)diacetate,
(7-(ethoxymethoxy)-4-oxochroman-3,3-diyl)bis(methylene)diacetate,
(6,8-dimethyl-4-oxochroman-3,3-diyl)bis(methylene)diacetate,
(6-methyl-4-oxochroman-3,3-diyl)bis(methylene)diacetate,
(7-methoxy-4-oxochroman-3,3-diyl)bis(methylene)dibenzoate,
(4-oxochroman-3,3-diyl)bis(methylene)diacetate,
(8-methyl-4-oxochroman-3,3-diyl)bis(methylene)diacetate,
(7-methyl-4-oxochroman-3,3-diyl)bis(methylene)diacetate,
(6-benzyl-4-oxochroman-3,3-diyl)bis(methylene)diacetate,
(6-benzyl-8-methyl-4-oxochroman-3,3-diyl)bis(methylene) diacetate,
(8-methyl-4-oxochroman-3,3,6-triyl)tris(methylene)triacetate and
2,2-bis(phenylamino)methyl)-3,4-dihydronaphthalen-1 (2H)-one.

Aliphatic radicals in the context of this invention include acyclic saturated or unsaturated hydrocarbon radicals which may be branched or straight-chain and also unsubstituted or monosubstituted or polysubstituted identically or differently, having preferably from 1 to 20 (i.e. 1, 2, 3, 4, 5, 6, 7, 8, 9, 10, 11, 12, 13, 14, 15, 16, 17, 18, 19 or 20), more preferably having from 1 to 12 (i.e. 1, 2, 3, 4, 5, 6, 7, 8, 9, 10, 11 or 12), most preferably having from 1 to 6 (i.e. 1, 2, 3, 4, 5 or 6) carbon atoms, i.e. $C_{1-20}$-, $C_{1-12}$-, $C_{1-6}$-alkyls, $C_{2-20}$-, $C_{2-12}$-, $C_{2-6}$-alkenyls and $C_{2-10}$-, $C_{2-12}$-, $C_{2-6}$-alkynyls. Alkenyls preferably have at least one C—C double bond and alkynyls preferably have at least one C—C triple bond. Advantageously, aliphatic radicals may be selected from the group which comprises methyl, ethyl, n-propyl, isopropyl, n-butyl, isobutyl, sec-butyl, tert-butyl, n-pentyl, isopentyl, neo-pentyl, n-hexyl, 2-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosanyl, ethenyl (vinyl), ethynyl, propenyl (—CH$_2$CH=CH$_2$, —CH=CH—CH$_3$, —C(=CH$_2$)—CH$_3$), 2-methylpropenyl, propynyl (—CH$_2$—C≡CH, —C≡C—CH$_3$), butenyl, butynyl, pentenyl, pentynyl, hexenyl, hexynyl, octenyl and octynyl.

In connection with aliphatic radicals, the term "substituted"—unless the expression is defined elsewhere in the description or in the claims—in the context of this invention is understood to mean single or multiple substitution, preferably optionally mono-, di-, tri-, tetra-, penta-, hexa-, hepta-, octa- or nonasubstitution, of one or more hydrogen atoms by, for example, F, Cl, Br, I, —CN, —NO$_2$, —OH, —SH and —NH$_2$, where the multiple substitution is multiple, for example double or triple, either on different or on the same atoms, for example triple on the same carbon atom as in the case of —CF$_3$ or —CH$_2$CF$_3$, or on different positions as in the case of —CH(OH)—CH=CCl—CH$_2$Cl.

Multiple substitution can be effected with the same or different substituents. Particularly preferred substituted aliphatic radicals are —CH$_2$—Cl, —CH$_2$—Br, —CH$_2$—CH$_2$—Cl, —CH$_2$—CH$_2$—Br, —CH$_2$—CH$_2$—CH$_2$—Br, —CH$_2$—CH$_2$—CH$_2$—Cl, —CF$_3$, —CHF$_2$, —CH$_2$F, —CCl$_3$, —CBr$_3$, —CH$_2$—CN, —CH$_2$—NO$_2$, —CF$_2$—CF$_3$, —CH$_2$—CF$_3$, —CCl$_2$—CCl$_3$, —CH$_2$—CH$_3$, —CH$_2$—CH$_2$—CN, —CH$_2$—CH$_2$—NO$_2$, —CF$_2$—CF$_2$—CF$_3$, —CH$_2$—CH$_2$—CH$_2$—CN and —CH$_2$—CH$_2$—CH$_2$—NO$_2$.

For the purposes of the present invention, the term "aryl radical" should preferably be understood to mean a radical which is selected from the group which comprises phenyl, naphthyl, phenanthrenyl and anthracenyl, and is unsubstituted or mono- or polysubstituted identically or differently. Aryl is more preferably an unsubstituted or monosubstituted or identically or differently polysubstituted, for example bi-, tri-, tetra- or pentasubstituted, phenyl, 1-naphthyl or 2-naphthyl.

In the context of the present invention, heteroaryl radicals are those heterocycles which are heteroaromatic. Heteroaryl radicals are preferably 5- to 14-membered, i.e. 5-, 6-, 7-, 8-, 9-, 10-, 11-, 12-, 13- or 14-membered, and have preferably 1, 2, 3, 4 or 5 heteroatoms selected independently from the group comprising oxygen, nitrogen and sulfur. Each heteroaryl radical may be present unsubstituted or monosubstituted or polysubstituted, for example bi-, tri-, tetra- or pentasubstituted, identically or differently.

Examples of heteroaryl radicals in the context of the present invention include thiophenyl, furanyl, pyrrolyl, pyrazolyl, pyranyl, pyridinyl, imidazolyl, indolyl, Isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinolinyl, isoquinolinyl, benzimidazolinyl, benzoxazolyl, benzisoxazolyl, benzothiazolyl, benzo[2,1,3] thiadiazolyl, [1,2,3]-benzothiadiazolyl, [2,1,3]-benzoxadiazolyl and [1,2,3]-benzoxadiazolyl.

In relation to aryl and heteroaryl radicals, "substituted" in the context of this invention is understood to mean the single or multiple substitution, preferably mono-, di-, tri-, tetra- or pentasubstitution, of one or more hydrogen atoms of the ring system by suitable substituents. When the definition of these suitable substituents in connection with aryl or heteroaryl radicals is not defined elsewhere in the description or in the claims, suitable substituents are F, Cl, Br, I, —CN, —CF$_3$, —SF$_5$, —OH, —O—C$_{1-10}$-alkyl, —NH$_2$, —NO$_2$, —O—CF$_3$, —S—CF$_3$, —SH, —S—C$_{1-5}$-alkyl, —C$_{1-5}$-alkyl, —C(═O)—OH, —C(═O)—O—C$_{1-5}$-alkyl, —O—C(═O)—C$_{1-5}$-alkyl, —NH—C$_{1-5}$-alkyl, —N(C$_{1-5}$-alkyl)$_2$, —NH—C(═O)—O—C$_{1-5}$alkyl, —C(═O)—H, —C(═O)—C$_{1-5}$-alkyl, —C(═O)—NH$_2$, —C(═O)—NH—C$_{1-5}$-alkyl, C(═O)—N—(C$_{1-5}$-alkyl)$_2$, —S(═O)$_2$—C$_{1-5}$-alkyl, —S(═O)$_2$-phenyl, —NH—S(═O)$_2$—C$_{1-5}$-alkyl, —S(═O)$_2$—NH—C$_{1-5}$-alkyl, cyclohexyl, cyclopentyl, pyridinyl, pyridazinyl, —(CH$_2$)-benzo[b]furanyl, —O-phenyl, —O-benzyl, phenyl and benzyl, where the cyclic moiety of the pyridinyl, cyclopentyl, cyclohexyl, pyridazinyl, —S(═O)$_2$-phenyl, —O-phenyl, —O-benzyl, phenyl, —(CH$_2$)-benzo[b]furanyl and benzyl radicals may in each case be substituted preferably by 1, 2, 3, 4 or 5 substituents selected independently from the group consisting of F, Cl, Br, —OH, —CF$_3$, —SF$_5$, —CN, —NO$_2$, —C$_{1-5}$-alkyl, —O—C$_{1-5}$-alkyl, —O—CF$_3$, —S—CF$_3$, phenyl and —O-benzyl.

The multiple substitution is effected with the same or with different substituents.

The aforementioned linear or branched alkylene, alkenylene or alkynylene groups preferably have from 1 to 5 carbon atoms, i.e. they are C$_{1-5}$-alkylene, C$_{2-5}$-alkenylene or C$_{2-5}$-alkynylene groups, each of which may be preferably unsubstituted or substituted by 1, 2, 3, 4 or 5 substituents selected independently from the group consisting of F, Cl, Br, —OH, —SH, —NH$_2$, —CN, —NO$_2$ and phenyl, where the phenyl radical may be preferably substituted by 1, 2, 3, 4 or 5 substituents selected independently from the group consisting of methyl, ethyl, n-propyl, isopropyl, n-butyl, isobutyl, sec-butyl, tert-butyl, n-pentyl, isopentyl and neopentyl.

Optionally substituted alkylene may particularly preferably be selected from the group consisting of —(CH$_2$)—, —(CH$_2$)$_2$—, —C(H)(CH$_3$)—, —C(CH$_3$)$_2$—, —(CH$_2$)$_3$—, —(CH$_2$)$_4$—, —(CH$_2$)$_5$—, —C(H)(CH$_3$)—(CH$_2$)—, —C(H)(C$_2$H$_5$)—(CH$_2$)—, —C(phenyl)$_2$- and —C(H)(phenyl).

Optionally substituted alkenylene groups may particularly preferably be selected from the group consisting of —CH═CH—, —C(CH$_3$)═CH—, —C(C$_2$H$_5$)═CH—, —CH═C(CH$_3$)—, —CH═C(C$_2$H$_5$)—, —CH═C(phenyl)-, —CH═C(p-tolyl), —C(phenyl)═CH— and —C(p-tolyl)═CH—.

An alkynylene group is more preferably a —C≡C— group.

Cycloaliphatic radicals in the context of this invention are cyclic saturated or unsaturated hydrocarbon radicals having preferably 3, 4, 5, 6, 7, 8, 9, 10, 11, 12, 13, 14, 15 or 16, more preferably 3, 4, 5, 6, 7 or 8 carbon atoms, where each radical may be unsubstituted or monosubstituted or polysubstituted identically or differently. Cycloaliphatic radicals preferably have 1, 2, 3, 4 or 5 heteroatoms selected independently from the group consisting of oxygen, nitrogen (NH) and sulfur.

Examples of cycloaliphatic radicals include cyclopropyl, cyclobutyl, cyclopentyl, cyclohexyl, cyclooctyl, cyclononyl, cyclodecyl, cycloundecyl, cyclododecyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl and dithiolanyl.

A mono- or polycyclic ring system is understood in the context of the present invention to mean mono- or polycyclic hydrocarbon radicals which may be saturated or unsaturated and optionally have 1, 2, 3, 4 or 5 heteroatom(s) as ring member(s), which are each independently selected from the group consisting of oxygen, nitrogen and sulfur.

Such a mono- or polycyclic ring system may, for example, be fused to an aryl radical or a heteroaryl radical.

When a polycyclic ring system, for example a bicyclic ring system, is present, the different rings may each independently have a different degree of saturation, i.e. be saturated or unsaturated. A polycyclic ring system is preferably a bicyclic ring system.

Examples of aryl radicals which are fused to a mono- or polycyclic ring system include [1,3]-benzodioxolyl, [1,4]-benzodioxanyl, [1,2,3,4]-tetrahydronaphthyl, [1,2,3,4]-tetrahydroquinolinyl, [1,2,3,4]-tetrahydroquinazolinyl and [3,4]-dihydro-2H-1,4-benzoxazinyl.

In connection with cycloaliphatic radicals and mono- or polycyclic ring systems, the term "substituted"—unless the expression is defined elsewhere in the description or in the claims—in the context of this invention is understood to mean the single or multiple substitution, for example the mono-, di-, tri-, tetra-, penta-, hexa-, hepta-, octa- or nonasubstitution, of one or more hydrogen atoms by, for example, oxo (═O), thioxo (═S), F, Cl, Br, I, —CN, —CF$_3$, —SF$_5$, —OH, —O—C$_{1-5}$-alkyl, —NH$_2$, —NO$_2$, —O—CF$_3$, —S—CF$_3$, —SH, —S—C$_{1-5}$-alkyl, —C$_{1-5}$-alkyl, —C(═O)—OH, —C(═O)—O—C$_{1-5}$-alkyl, —O—C(═O)—C$_{1-5}$-alkyl, —NH—C$_{1-5}$-alkyl, —N(C$_{1-5}$-alkyl)$_2$, —NH—C(═O)—O—C$_{1-5}$-alkyl, —C(═O)—H, —C(═O)—C$_{1-5}$-alkyl, —C(═O)—NH$_2$, —C(═O)—NH—C$_{1-5}$-alkyl, C(═O)—N—(C$_{1-5}$-alkyl)$_2$, —S(═O)$_2$—C$_{1-5}$-alkyl, —S(═O)$_2$-phenyl, —NH—S(═O)$_2$—C$_{1-5}$-alkyl, —S(═O)$_2$—NH—C$_{1-5}$-alkyl, cyclohexyl, cyclopentyl, pyridinyl, pyridazinyl, —(CH$_2$)-benzo[b]furanyl, —O-phenyl, —O-benzyl, phenyl and benzyl, where the cyclic moiety of the pyridinyl, cyclopentyl, cyclohexyl, pyridazinyl, —S(═O)$_2$-phenyl, —O-phenyl, —O-benzyl, phenyl, —(CH$_2$)-benzo[b]furanyl and benzyl radicals may in each case be substituted preferably by 1, 2, 3, 4 or 5 substituents selected independently from the group consisting of F, Cl, Br, —OH, —CF$_3$, —SF$_5$, —CN, —NO$_2$, —C$_{1-5}$-alkyl, —O—C$_{1-5}$-alkyl, —O—CF$_3$, —S—CF$_3$, phenyl and —O-benzyl. The polysubstitution can be effected multiply, for example doubly or triply, either on different or on the same atoms. The polysubstitution can be effected with identical or different substituents.

At least some of the compounds excluded above, whose structures are reproduced explicitly below,

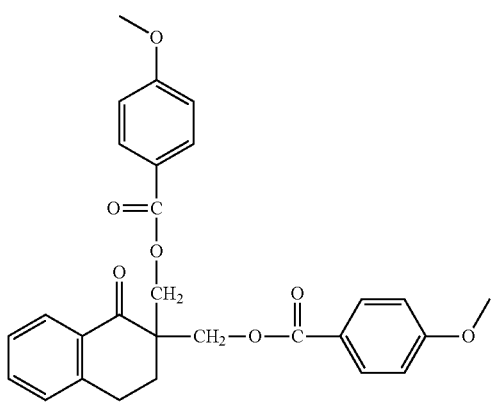
(1-oxo-1,2,3,4-tetrahydronaphthalene-2,2-diyl)bis(methylene)bis(4-methoxybenzoate)

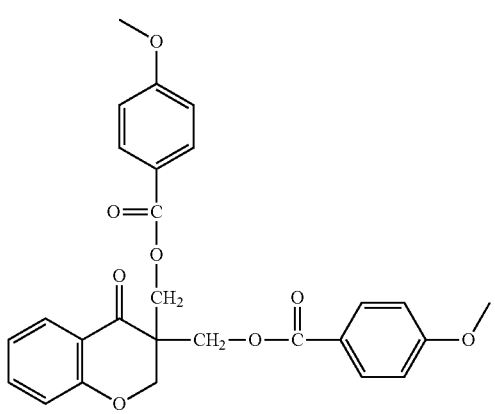
(4-oxochroman-3,3-diyl)bis(methylene) bis(4-methoxybenzoate)

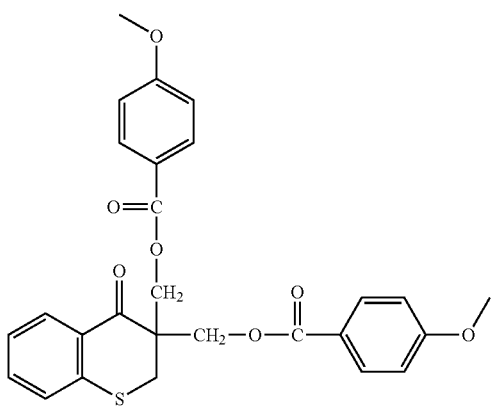
(4-oxothiochroman-3,3-diyl)bis(methylene) bis(4-methoxybenzoate)

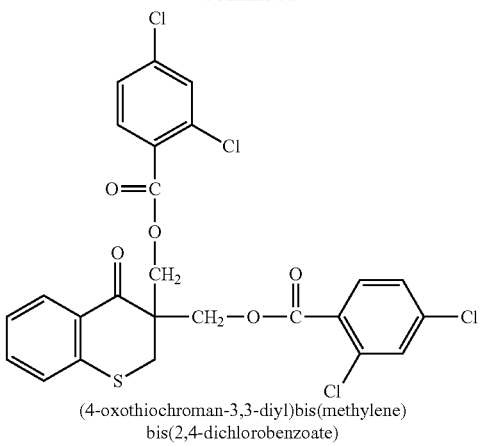
(4-oxothiochroman-3,3-diyl)bis(methylene) bis(2,4-dichlorobenzoate)

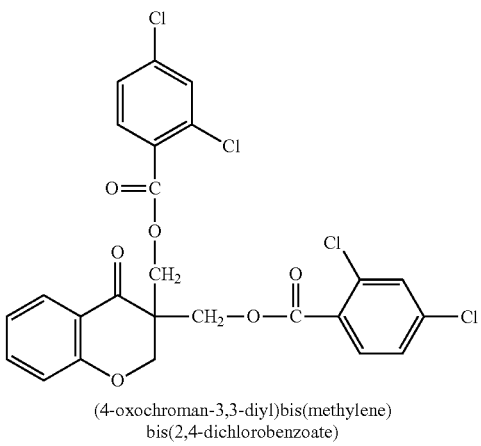
(4-oxochroman-3,3-diyl)bis(methylene) bis(2,4-dichlorobenzoate)

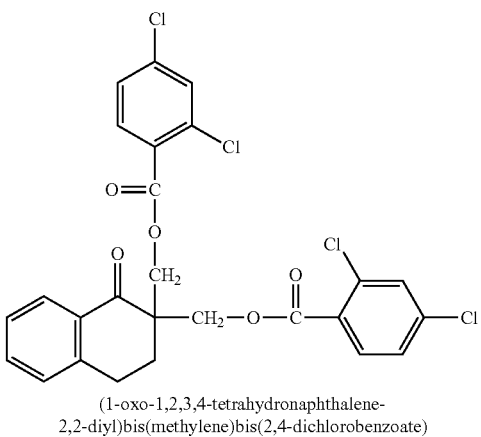
(1-oxo-1,2,3,4-tetrahydronaphthalene-2,2-diyl)bis(methylene)bis(2,4-dichlorobenzoate)

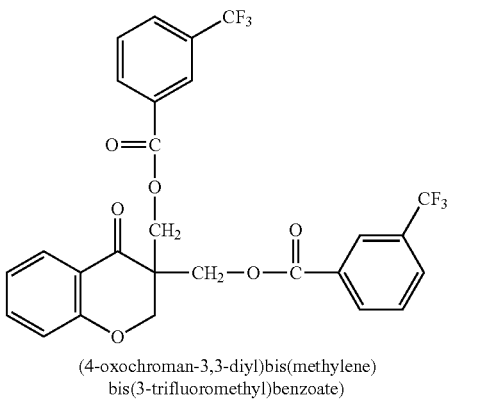
(4-oxochroman-3,3-diyl)bis(methylene) bis(3-trifluoromethyl)benzoate)

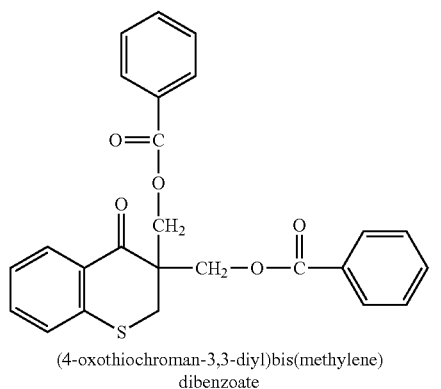
(4-oxothiochroman-3,3-diyl)bis(methylene)
dibenzoate

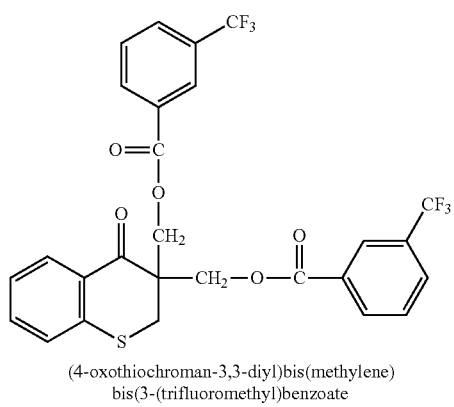
(4-oxothiochroman-3,3-diyl)bis(methylene)
bis(3-(trifluoromethyl)benzoate

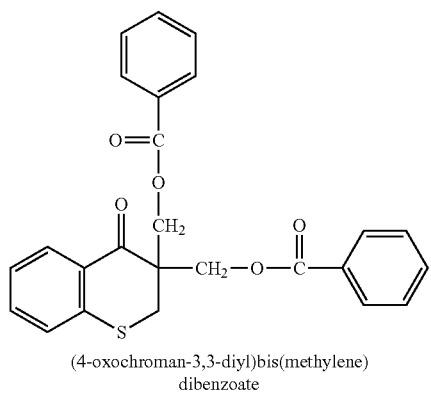
(4-oxochroman-3,3-diyl)bis(methylene)
dibenzoate

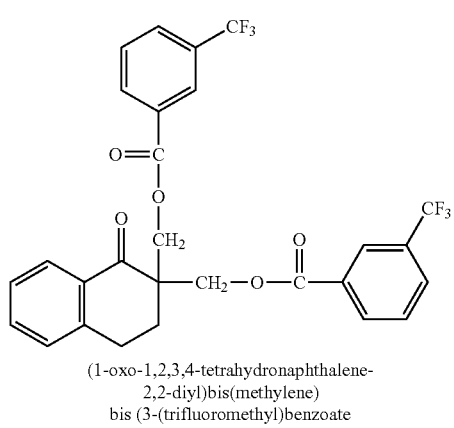
(1-oxo-1,2,3,4-tetrahydronaphthalene-
2,2-diyl)bis(methylene)
bis (3-(trifluoromethyl)benzoate

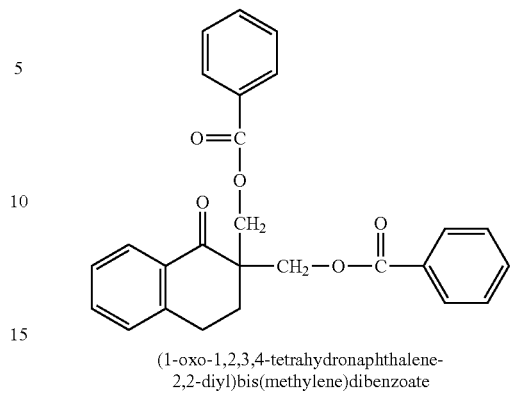
(1-oxo-1,2,3,4-tetrahydronaphthalene-
2,2-diyl)bis(methylene)dibenzoate

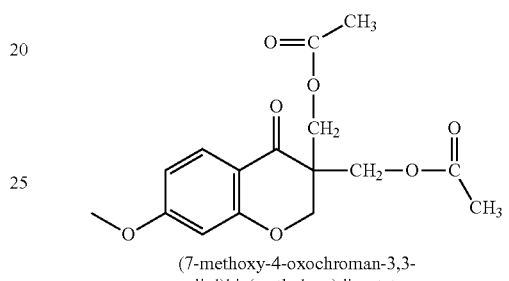
(7-methoxy-4-oxochroman-3,3-
diyl)bis(methylene)diacetate

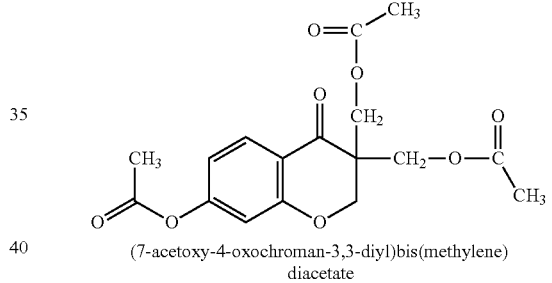
(7-acetoxy-4-oxochroman-3,3-diyl)bis(methylene)
diacetate

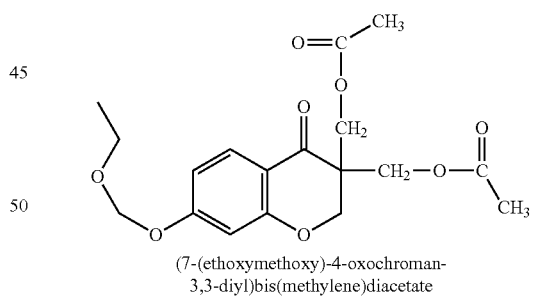
(7-(ethoxymethoxy)-4-oxochroman-
3,3-diyl)bis(methylene)diacetate

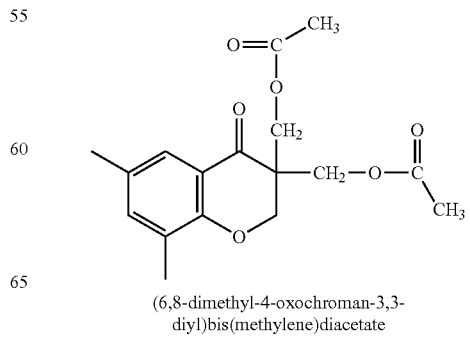
(6,8-dimethyl-4-oxochroman-3,3-
diyl)bis(methylene)diacetate

-continued

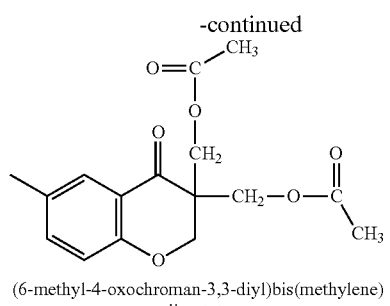
(6-methyl-4-oxochroman-3,3-diyl)bis(methylene) diacetate

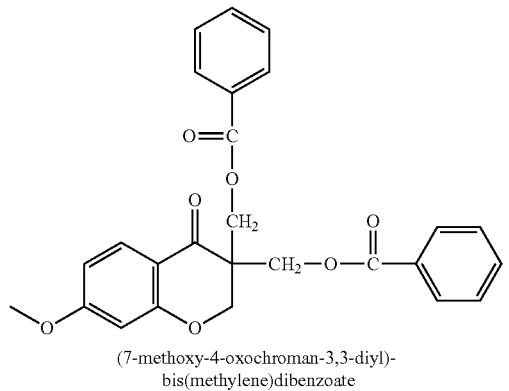
(7-methoxy-4-oxochroman-3,3-diyl)-bis(methylene)dibenzoate

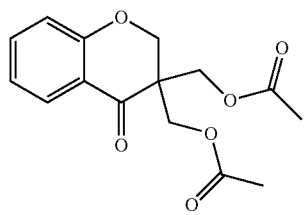
(4-oxochroman-3,3-diyl)bis(methylene) diacetate

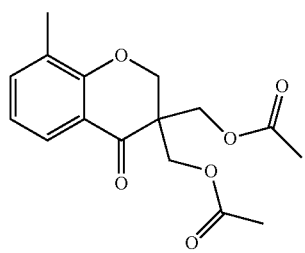
(8-methyl-4-oxochroman-3,3-diyl)bis(methylene) diacetate

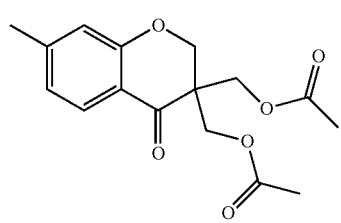
(7-methyl-4-oxochroman-3,3-diyl)bis(methylene) diacetate

-continued

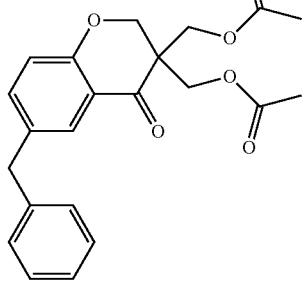
(6-benzyl-4-oxochroman-3,3-diyl) bis(methylene)diacetate

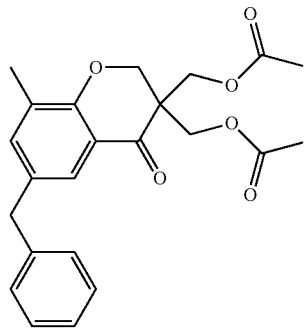
(6-benzyl-8-methyl-4-oxochroman-3,3-diyl)bis(methylene)diacetate

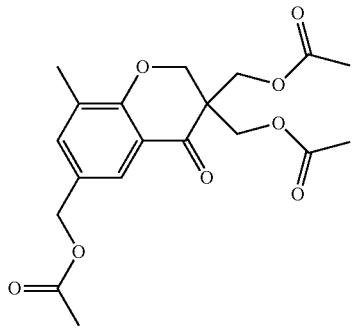
(8-methyl-4-oxochroman-3,3,6-triyl)tris(methylene)triacetate

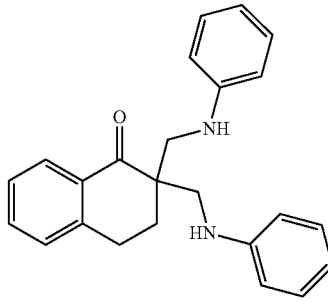
2,2-bis(phenylamino)methyl)-3,4-dihydronaphthalen-1(2H)-one are commercially available and/or have already been synthesized, but have not been used to date as active pharmaceutical ingredients in medicaments. The compounds excluded as active pharmaceutical ingredients in the medicaments described below and their use for producing medicaments as described below therefore likewise form part of the subject matter of the present invention.

Particular preference is given to substituted benzofused cyclohexanone derivatives of the general formula I specified above in which n is 1;

X is $CH_2$, O, S, S(=O), S(=O)$_2$, N(H), N($R^7$), N[C(=O)—$R^8$] or N[C(=O)—O—$R^9$];

Y is O, O—C(=O), O—C(=O)—O, O—S(=O)$_2$, O—C(=S)—N(H) or O—C(=O)—N(H); where the free atom which binds to the $R^5$ radical is always stated last;

$R^1$, $R^2$, $R^3$ and $R^4$ are each independently
H, F, Cl, Br, I, —SF$_5$, —CN, —NC, —NO$_2$, —OH, —SH, —OR$^{10}$, —SR$^{11}$,
or a radical selected from the group consisting of methyl, —CF$_3$, —CHF$_2$, —CH$_2$F, —CCl$_3$, —CBr$_3$, —CH$_2$—CN, —CH$_2$—NO$_2$, ethyl, —CF$_2$—CF$_3$, —CH$_2$—CF$_3$, —CCl$_2$—CCl$_3$, —CF$_2$—CH$_3$, —CH$_2$—CH$_2$—CN, —CH$_2$—CH$_2$—NO$_2$, n-propyl, —CF$_2$—CF$_2$—CF$_3$, —CH$_2$—CH$_2$—CH$_2$—CN, —CH$_2$—CH$_2$—CH$_2$—NO$_2$, isopropyl, n-butyl, sec-butyl, isobutyl, tert-butyl, 1,1-dimethylpropyl, n-pentyl, sec-pentyl, n-hexyl and n-heptyl;

$R^5$ is a —C(=O)—R$^{26}$ group;
is a —S(=O)$_2$—R$^{27}$ group;
is a radical selected from the group consisting of methyl, ethyl, n-propyl, isopropyl, n-butyl, sec-butyl, isobutyl, tert-butyl, 1,1-dimethylpropyl, n-pentyl, sec-pentyl, n-hexyl and n-heptyl;
is a radical selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl and thiomorpholinyl;
or is a radical selected from the group consisting of phenyl, benzyl, phenethyl, naphthyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinolinyl, isoquinolinyl, benzimidazolinyl, benzoxazolyl, benzisoxazolyl and benzothiazolyl, where the radical may in each case optionally be substituted by 1, 2, 3, 4 or 5 substituents selected independently from the group consisting of —SF$_5$, F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl, tert-butyl, —C(=O)—OH, —C(=O)—O—CH$_3$, —C(=O)—O—C$_2$H$_5$, —C(=O)—O—C(CH$_3$)$_3$, —O—C(=O)—CH$_3$, —O—C(=O)—C$_2$H$_5$, —O—C(=O)—C(CH$_3$)$_3$, —N(CH$_3$)$_2$, —N(C$_2$H$_5$)$_2$, —NH—CH$_3$, —NH—C$_2$H$_5$, —NH—C(=O)—O—CH$_3$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—C(CH$_3$)$_3$, —C(=O)—NH$_2$, —C(=O)—NH—CH$_3$, —C(=O)—NH—C$_2$H$_5$, —C(=O)—N—(CH$_3$)$_2$, —C(=O)—N—(C$_2$H$_5$)$_2$, —S(=O)$_2$—CH$_3$, —S(=O)$_2$—C$_2$H$_5$, —NH—S(=O)$_2$—CH$_3$, —NH—S(=O)$_2$—C$_2$H$_5$, —S(=O)$_2$—NH—CH$_3$ and —S(=O)$_2$—NH—C$_2$H$_5$;
with the proviso that $R^5$ is not a radical selected from the group consisting of methyl, ethyl, n-propyl, isopropyl, n-butyl, sec-butyl, isobutyl, tert-butyl, 1,1-dimethylpropyl, n-pentyl, sec-pentyl, n-hexyl and n-heptyl when $R^6$ is simultaneously a hydrogen radical or is —(CH$_2$)—O—R$^{24}$ in which R$^{24}$ is a radical selected from the group consisting of methyl, ethyl, n-propyl, isopropyl, n-butyl, sec-butyl, isobutyl, tert-butyl, 1,1-dimethylpropyl, n-pentyl, sec-pentyl, n-hexyl and n-heptyl;

$R^6$ is a hydrogen radical;
is —(CH$_2$)—Z—R$^{24}$;
or is —(CH$_2$)—OR$^{25}$;

$R^7$, $R^8$ and $R^9$ are each independently
a radical selected from the group consisting of methyl, ethyl, n-propyl, isopropyl, n-butyl, sec-butyl, isobutyl, tert-butyl, 1,1-dimethylpropyl, n-pentyl, sec-pentyl, n-hexyl and n-heptyl;
or a radical selected from the group consisting of benzyl and phenethyl, where the radical may in each case optionally be substituted by 1, 2, 3, 4 or 5 substituents selected independently from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl and tert-butyl;

$R^{10}$ and $R^{11}$, are each independently
a radical selected from the group consisting of methyl, ethyl, n-propyl, isopropyl, n-butyl, sec-butyl, isobutyl, tert-butyl, 1,1-dimethylpropyl, n-pentyl, sec-pentyl, n-hexyl and n-heptyl;
or a radical selected from the group consisting of phenyl, benzyl and phenethyl, where the radical may in each case optionally be substituted by 1, 2, 3, 4 or 5 substituents selected independently from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl and tert-butyl;

Z is O, O—C(=O), O—C(=O)—O, O—S(=O)$_2$, O—C(=S)—N(H) or O—C(=O)—N(H); where the free atom which binds to the R$^{24}$ radical is always stated last;

$R^{24}$ is a —C(=O)—R$^{28}$ group;
is a —S(=O)$_2$—R$^{29}$ group;
is a radical selected from the group consisting of methyl, ethyl, n-propyl, isopropyl, n-butyl, sec-butyl, isobutyl, tert-butyl, 1,1-dimethylpropyl, n-pentyl, sec-pentyl, n-hexyl and n-heptyl;
is a radical selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl and thiomorpholinyl;
or is a radical selected from the group consisting of phenyl, benzyl, phenethyl, naphthyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinolinyl, isoquinolinyl, benzimidazolinyl, benzoxazolyl, benzisoxazolyl and benzothiazolyl, where the radical may in each case optionally be substituted by 1, 2, 3, 4 or 5 substituents selected independently from the group consisting of —SF$_5$, F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl, tert-butyl, —C(=O)—OH, —C(=O)—O—CH$_3$, —C(=O)—O—C$_2$H$_5$, —C(=O)—O—C(CH$_3$)$_3$, —O—C(=O)—CH$_3$, —O—C(=O)—C$_2$H$_5$, —O—C(=O)—C(CH$_3$)$_3$, —N(CH$_3$)$_2$, —N(C$_2$H$_5$)$_2$, —NH—CH$_3$, —NH—C$_2$H$_5$, —NH—C(=O)—O—CH$_3$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—C(CH$_3$)$_3$, —C(=O)—NH$_2$, —C(=O)—NH—CH$_3$, —C(=O)—NH—C$_2$H$_5$, —C(=O)—N—(CH$_3$)$_2$, —C(=O)—N—(C$_2$H$_5$)$_2$, —S(=O)$_2$—CH$_3$, —S(=O)$_2$—C$_2$H$_5$, —NH—S(=O)$_2$—CH$_3$, —NH—S(=O)$_2$—C$_2$H$_5$, —S(=O)$_2$—NH—CH$_3$ and —S(=O)$_2$—NH—C$_2$H$_5$;

$R^{25}$ is a hydrogen radical; and $R^{26}$, $R^{27}$, $R^{28}$ and $R^{29}$ are each independently
  a radical selected from the group consisting of phenyl, naphthyl, thiophenyl, furanyl and pyridinyl, where the radical may in each case optionally be substituted by 1, 2, 3, 4 or 5 substituents selected independently from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl, tert-butyl, —N(CH$_3$)$_2$, —N(C$_2$H$_5$)$_2$, —NH—CH$_3$ and —NH—C$_2$H$_5$;

in each case, as appropriate, in the form of one of their pure stereoisomers, especially enantiomers or diastereomers, of its racemates or in the form of a mixture of stereoisomers, especially of the enantiomers and/or diastereomers, in any mixing ratio, or in each case in the form of corresponding salts, or in each case in the form of corresponding solvates, excluding the compounds
(1-oxo-1,2,3,4-tetrahydronaphthalene-2,2-diyl)bis(methylene)bis(4-methoxybenzoate),
(4-oxochroman-3,3-diyl)bis(methylene)bis(4-methoxybenzoate),
(4-oxothiochroman-3,3-diyl)bis(methylene)bis(4-methoxybenzoate),
(4-oxothiochroman-3,3-diyl)bis(methylene)bis(2,4-dichlorobenzoate),
(4-oxochroman-3,3-diyl)bis(methylene)bis(2,4-dichlorobenzoate),
(1-oxo-1,2,3,4-tetrahydronaphthalene-2,2-diyl)bis(methylene)bis(2,4-dichlorobenzoate),
(4-oxochroman-3,3-diyl)bis(methylene)bis(3-(trifluoromethyl)benzoate),
(4-oxothiochroman-3,3-diyl)bis(methylene)dibenzoate,
(4-oxothiochroman-3,3-diyl)bis(methylene)bis(3-trifluoromethyl)benzoate),
(4-oxothiochroman-3,3-diyl)bis(methylene)dibenzoate,
(1-oxo-1,2,3,4-tetrahydronaphthalene-2,2-diyl)bis(methylene)bis(3-trifluoromethyl)benzoate,
(1-oxo-1,2,3,4-tetrahydronaphthalene-2,2-diyl)bis(methylene)dibenzoate,
(7-methoxy-4-oxochroman-3,3-diyl)bis(methylene)diacetate,
(7-acetoxy-4-oxochroman-3,3-diyl)bis(methylene)diacetate,
(7-(ethoxymethoxy)-4-oxochroman-3,3-diyl)bis(methylene)diacetate,
(6,8-dimethyl-4-oxochroman-3,3-diyl)bis(methylene)diacetate,
(6-methyl-4-oxochroman-3,3-diyl)bis(methylene)diacetate,
(7-methoxy-4-oxochroman-3,3-diyl)bis(methylene)dibenzoate,
(4-oxochroman-3,3-diyl)bis(methylene)diacetate,
(8-methyl-4-oxochroman-3,3-diyl)bis(methylene)diacetate,
(7-methyl-4-oxochroman-3,3-diyl)bis(methylene)diacetate,
(6-benzyl-4-oxochroman-3,3-diyl)bis(methylene)diacetate,
(6-benzyl-8-methyl-4-oxochroman-3,3-diyl)bis(methylene)diacetate,
(8-methyl-4-oxochroman-3,3,6-triyl)tris(methylene)triacetate and
2,2-bis(phenylamino)methyl)-3,4-dihydronaphthalen-1(2H)-one.

Very particular preference is given to substituted benzofused cyclohexanone derivatives of the above-specified general formula I in which n is 1;

X is CH$_2$, O, S, S(=O) or S(=O)$_2$;

Y is O, O—C(=O), O—C(=O)—O, O—S(=O)$_2$, O—C(=S)—N(H) or O—C(=O)—N(H); where the free atom which binds to the $R^5$ radical is always stated last;

$R^1$, $R^2$, $R^3$ and $R^4$, are each independently
  H, F, Cl, Br, —SF$_5$, —OH, —OR$^{10}$,
  or a radical selected from the group consisting of methyl, —CF$_3$, —CHF$_2$, —CH$_2$F, —CCl$_3$, —CBr$_3$, —CH$_2$—CN, —CH$_2$—NO$_2$, ethyl, —CF$_2$—CF$_3$, —CH$_2$—CF$_3$, n-propyl, isopropyl, n-butyl, sec-butyl, isobutyl, tert-butyl, 1,1-dimethylpropyl and n-pentyl;

$R^5$ is a —C(=O)—R$^{26}$ group;
  is a —S(=O)$_2$—R$^{27}$ group;
  is a radical selected from the group consisting of methyl, ethyl, n-propyl, isopropyl, n-butyl, sec-butyl, isobutyl, tert-butyl, 1,1-dimethylpropyl, n-pentyl, sec-pentyl, n-hexyl and n-heptyl;
  is a radical selected from the group consisting of cyclopropyl, cyclobutyl, cyclopentyl, cyclohexyl, cycloheptyl, cyclopentenyl, cyclohexenyl and cycloheptenyl;
  or is a radical selected from the group consisting of phenyl, naphthyl, thiophenyl, furanyl, pyridinyl, indolyl, thiazolyl and oxazolyl, where the radical may in each case optionally be substituted by 1, 2, 3, 4 or 5 substituents selected independently from the group consisting of F, Cl, Br, —CF$_3$, —O—CH$_3$, —O—C$_2$H$_5$, —O—CF$_3$, —S—CF$_3$, methyl, ethyl, n-propyl, isopropyl, n-butyl, sec-butyl, isobutyl and tert-butyl;
  with the proviso that $R^5$ is not a radical selected from a group consisting of methyl, ethyl, n-propyl, isopropyl, n-butyl, sec-butyl, isobutyl, tert-butyl, 1,1-dimethylpropyl, n-pentyl, sec-pentyl, n-hexyl and n-heptyl when $R^6$ is simultaneously a hydrogen radical or is —(CH$_2$)—O—R$^{24}$ in which $R^{24}$ is a radical selected from the group consisting of methyl, ethyl, n-propyl, isopropyl, n-butyl, sec-butyl, isobutyl, tert-butyl, 1,1-dimethylpropyl, n-pentyl, sec-pentyl, n-hexyl and n-heptyl, $R^6$ is a hydrogen radical;
  is —(CH$_2$)—Z—R$^{24}$;
  or is —(CH$_2$)—OR$^{25}$;

$R^{10}$ is a radical selected from the group consisting of methyl, ethyl, n-propyl, isopropyl, n-butyl, sec-butyl, isobutyl, tert-butyl, 1,1-dimethylpropyl, n-pentyl, sec-pentyl, n-hexyl and n-heptyl;

Z is O, O—C(=O), O—C(=O)—O, O—S(=O)$_2$, O—C(=S)—N(H) or O—C(=O)—N(H); where the free atom which binds to the $R^{24}$ radical is always stated last;

$R^{24}$ is a —C(═O)—$R^{28}$ group;
is a —S(═O)$_2$—$R^{29}$ group;
is a radical selected from the group consisting of methyl, ethyl, n-propyl, isopropyl, n-butyl, sec-butyl, isobutyl, tert-butyl, 1,1-dimethylpropyl, n-pentyl, sec-pentyl, n-hexyl and n-heptyl;
is a radical selected from the group consisting of cyclopropyl, cyclobutyl, cyclopentyl, cyclohexyl, cycloheptyl, cyclopentenyl, cyclohexenyl and cycloheptenyl;
or is a radical selected from the group consisting of phenyl, naphthyl, thiophenyl, furanyl, pyridinyl, indolyl, thiazolyl and oxazolyl, where the radical may in each case optionally be substituted by 1, 2, 3, 4 or 5 substituents selected independently from the group consisting of F, Cl, Br, —CF$_3$, —O—CH$_3$, —O—C$_2$H$_5$, —O—CF$_3$, —S—CF$_3$, methyl, ethyl, n-propyl, isopropyl, n-butyl, sec-butyl, isobutyl and tert-butyl;
$R^{25}$ is a hydrogen radical; and
$R^{26}$, $R^{27}$, $R^{28}$ and $R^{29}$ are each independently
a radical selected from the group consisting of phenyl, naphthyl, thiophenyl, furanyl and pyridinyl, where the radical may in each case optionally be substituted by 1, 2, 3, 4 or 5 substituents selected independently from the group consisting of F, Cl, Br, I, —CF$_3$, —SF$_5$, —O—CH$_3$, —O—C$_2$H$_5$, —S—CF$_3$, methyl, ethyl, n-propyl, isopropyl, n-butyl, sec-butyl, isobutyl and tert-butyl;
in each case, as appropriate, in the form of one of their pure stereoisomers, especially enantiomers or diastereomers, of its racemates or in the form of a mixture of stereoisomers, especially of the enantiomers and/or diastereomers, in any mixing ratio, or in each case in the form of corresponding salts, or in each case in the form of corresponding solvates,
excluding the compounds
(1-oxo-1,2,3,4-tetrahydronaphthalene-2,2-diyl)bis(methylene)bis(4-methoxybenzoate),
(4-oxochroman-3,3-diyl)bis(methylene)bis(4-methoxybenzoate),
(4-oxothiochroman-3,3-diyl)bis(methylene)bis(4-methoxybenzoate),
(4-oxothiochroman-3,3-diyl)bis(methylene)bis(2,4-dichlorobenzoate),
(4-oxochroman-3,3-diyl)bis(methylene)bis(2,4-dichlorobenzoate),
(1-oxo-1,2,3,4-tetrahydronaphthalene-2,2-diyl)bis(methylene)bis(2,4-dichlorobenzoate),
(4-oxochroman-3,3-diyl)bis(methylene)bis(3-(trifluoromethyl)benzoate),
(4-oxothiochroman-3,3-diyl)bis(methylene)dibenzoate,
(4-oxothiochroman-3,3-diyl)bis(methylene)bis(3-(trifluoromethyl)benzoate),
(4-oxochroman-3,3-diyl)bis(methylene)debenzoate
(1-oxo-1,2,3,4-tetrahydronaphthalene-2,2-diyl)bis(methylene)bis(3-(trifluoromethyl)benzoate),
(1-oxo-1,2,3,4-tetrahydronaphthalene-2,2-diyl)bis(methylene)dibenzoate,
(7-methoxy-4-oxochroman-3,3-diyl)bis(methylene)diacetate,
(7-acetoxy-4-oxochroman-3,3-diyl)bis(methylene)diacetate,
(7-(ethoxymethoxy)-4-oxochroman-3,3-diyl)bis(methylene)diacetate,
(6,8-dimethyl-4-oxochroman-3,3-diyl)bis(methylene)diacetate,
(6-methyl-4-oxochroman-3,3-diyl)bis(methylene)diacetate,
(7-methoxy-4-oxochroman-3,3-diyl)bis(methylene)dibenzoate,
(4-oxochroman-3,3-diyl)bis(methylene)diacetate,
(8-methyl-4-oxochroman-3,3-diyl)bis(methylene)diacetate,
(7-methyl-4-oxochroman-3,3-diyl)bis(methylene)diacetate,
(6-benzyl-4-oxochroman-3,3-diyl)bis(methylene)diacetate,
(6-benzyl-8-methyl-4-oxochroman-3,3-diyl)bis(methylene)diacetate,
(8-methyl-4-oxochroman-3,3,6-triyl)tris(methylene)triacetate and
2,2-bis((phenylamino)methyl)-3,4-dihydronaphthalen-1(2H)-one.

Even more preferred are substituted benzofused cyclohexanone derivatives of the above-specified general formula I selected from the group consisting of

[2] (4-oxothiochroman-3,3-diyl)bis(methylene)bis(2-(trifluoromethyl)-benzoate)
[3] (6-methoxy-4-oxothiochroman-3,3-diyl)bis(methylene)bis(3-(trifluoromethyl)benzoate)
[4] (8-chloro-4-oxothiochroman-3,3-diyl)bis(methylene)bis(3-(trifluoromethyl)benzoate)
[5] (8-methyl-4-oxothiochroman-3,3-diyl)bis(methylene)bis(3-(trifluoromethyl)benzoate)
[6] (8-methyl-4-oxothiochroman-3,3-diyl)bis(methylene)bis(2-(trifluoromethyl)benzoate)
[7] (6,8-dimethyl-4-oxothiochroman-3,3-diyl)bis(methylene)bis(4-tert-butylbenzenesulfonate)
[8] 4-tert-butylbenzenesulfonic acid 3-hydroxymethyl-4-oxo-thiochroman-3-ylmethyl ester
[9] (8-methyl-4-oxothiochroman-3,3-diyl)bis(methylene)bis(4-tert-butylbenzenesulfonate)
[10] (6,8-dimethyl-4-oxothiochroman-3,3-diyl)bis(methylene)bis(3-(trifluoromethyl)benzoate)
[11] (6-fluoro-4-oxothiochroman-3,3-diyl)bis(methylene)bis(3-(trifluoromethyl)benzoate)
[12] (6,8-dimethyl-4-oxothiochroman-3,3-diyl)bis(methylene)bis(2-(trifluoromethyl)benzoate)
[13] 4-tert-butylbenzenesulfonic acid 3-hydroxymethyl-8-methyl-4-oxo-thiochroman-3-ylmethyl ester
[14] (8-chloro-4-oxothiochroman-3,3-diyl)bis(methylene)bis(2-(trifluoromethyl)phenylcarbamate)
[15] (6-fluoro-4-oxothiochroman-3,3-diyl)bis(methylene)bis(2-(trifluoromethyl)benzoate)
[16] 2-trifluoromethylbenzoic acid 6-fluoro-3-hydroxymethyl-4-oxo-thiochroman-3-ylmethyl ester
[17] (6-fluoro-4-oxothiochroman-3,3-diyl)bis(methylene)bis(4-tert-butylbenzenesulfonate)
[18] 4-tert-butylbenzenesulfonic acid 6-fluoro-3-hydroxymethyl-4-oxo-thiochroman-3-ylmethyl ester
[19] 4-tert-butylbenzenesulfonic acid 8-chloro-3-hydroxymethyl-4-oxo-thiochroman-3-ylmethyl ester
[20] (8-chloro-4-oxothiochroman-3,3-diyl)bis(methylene)bis(3-(trifluoromethyl)phenylcarbamate)
[21] 2-trifluoromethylbenzoic acid 8-chloro-3-hydroxymethyl-4-oxo-thiochroman-3-ylmethyl ester
[22] (5-methyl-4-oxothiochroman-3,3-diyl)bis(methylene)bis(4-tert-butylbenzenesulfonate)
[23] 2-trifluoromethylbenzoic acid 3-hydroxymethyl-6-methoxy-4-oxo-thiochroman-3-ylmethyl ester
[24] (7,8-dichloro-4-oxothiochroman-3,3-diyl)bis(methylene)bis(4-tert-butylbenzenesulfonate)
[25] (6-methoxy-4-oxothiochroman-3,3-diyl)bis(methylene)bis(4-tert-butylbenzenesulfonate)
[26] (8-chloro-4-oxothiochroman-3,3-diyl)bis(methylene)bis(2-(trifluoromethyl)benzoate)
[27] (5-methyl-4-oxothiochroman-3,3-diyl)bis(methylene)bis(2-(trifluoromethyl)phenylcarbamate)

[28] (5-methyl-4-oxothiochroman-3,3-diyl)bis(methylene) bis(3-(trifluoromethyl)phenylcarbamate)
[29] (7,8-dichloro-4-oxothiochroman-3,3-diyl)bis(methylene)bis(3-(trifluoromethyl)phenylcarbamate)
[30] (6-fluoro-4-oxothiochroman-3,3-diyl)bis(methylene) bis(3-(trifluoromethyl)phenylcarbamate)
[31] (7,8-dichloro-4-oxothiochroman-3,3-diyl)bis(methylene)bis(2-(trifluoromethyl)phenylcarbamate)
[32] 2-trifluoromethylbenzoic acid 3-hydroxymethyl-5-methyl-4-oxo-thiochroman-3-ylmethyl ester
[33] (5-methyl-4-oxothiochroman-3,3-diyl)bis(methylene) bis(3-(trifluoromethyl)benzoate)
[34] 3-trifluoromethylbenzoic acid 3-hydroxymethyl-5-methyl-4-oxo-thiochroman-3-ylmethyl ester
[35] (5-methyl-4-oxothiochroman-3,3-diyl)bis(methylene) bis(2-(trifluoromethyl)benzoate)
[36] 3,3-bis(4-tert-butylbenzenesulfonyloxymethyl)-5-methyl-1,1-dioxo-1$\lambda^6$-thiochroman-4-one
[37] 3,3-bis(3-trifluoromethylphenylcarbamoyloxymethyl)-5-methyl-1,1-dioxo-1$\lambda^6$-thiochroman-4-one
[38] bis(4-chlorophenyl)(4-oxothiochroman-3,3-diyl)bis(methylene)-dicarbonate
[39] (7-methyl-4-oxothiochroman-3,3-diyl)bis(methylene) bis(phenylcarbamate)
[40] (5-methyl-4-oxothiochroman-3,3-diyl)bis(methylene) bis(phenylcarbamate)
[41] 3,3-bis(phenylcarbamoyloxymethyl)thiochroman-4-one
[42] 3,3-bis(4-methoxyphenylcarbamoyloxymethyl)thiochroman-4-one
[43] 3,3-bis(phenylcarbamoyloxymethyl)-1,1-dioxo-1$\lambda^6$-thiochroman-4-one
[44] 3,3-bis(phenylcarbamoyloxymethyl)-1-oxo-1$\lambda^4$-thiochroman-4-one
[45] 3,3-bis(phenylcarbamoyloxymethyl)-5-methyl-1-oxo-1$\lambda^4$-thiochroman-4-one
[46] 3,3-bis(phenylcarbamoyloxymethyl)-5-methyl-1,1-dioxo-1$\lambda^6$-thiochroman-4-one
[47] 3,3-bis(phenylcarbamoyloxymethyl)-7-methyl-1-oxo-1$\lambda^4$-thiochroman-4-one
[48] 3,3-bis(phenylcarbamoyloxymethyl)-7-methyl-1,1-dioxo-1$\lambda^6$-thiochroman-4-one
[49] phenylcarbamic acid 3-methoxymethyl-4-oxothiochroman-3-ylmethyl ester
[50] 3,3-bis(4-tert-butylphenylcarbamoyloxymethyl)thiochroman-4-one
[51] 3,3-bis(2-tert-butylphenylcarbamoyloxymethyl)thiochroman-4-one
[52] 3,3-bis(4-trifluoromethylphenylcarbamoyloxymethyl) thiochroman-4-one
[53] 3,3-bis(2-trifluoromethylphenylcarbamoyloxymethyl) thiochroman-4-one
[54] 3,3-bis(3-trifluoromethylphenylcarbamoyloxymethyl) thiochroman-4-one
[55] phenylcarbamic acid 4-oxothiochroman-3-ylmethyl ester and
[56] bis(3-trifluoromethyl)(4-oxothiochroman-3,3-diyl)bis(methylene)-dicarbonate;
in each case, as appropriate, in the form of one of its pure stereoisomers, especially enantiomers or diastereomers, of its racemates or in the form of a mixture of stereoisomers, especially of the enantiomers and/or diastereomers, in any mixing ratio, or in each case in the form of corresponding salts, or in each case in the form of corresponding solvates.

Preference may additionally be given to inventive substituted compounds which, in the FLIPR assay, in a concentration of 10 μM, have an inhibition of the $Ca^{2+}$ ion current in dorsal root ganglia of rats of at least 10%, preferably of at least 30%, more preferably of at least 50%, even more preferably of at least 70%, even more preferably of at least 90%, compared to the maximum achievable inhibition of the $Ca^{2+}$ ion current with capsaicin in a concentration of 10 μM.

In the FLIPR assay, the $Ca^{2+}$ current is quantified with the aid of a $Ca^{2+}$-sensitive dye (Fluo-4 type, Molecular Probes Europe BV, Leiden, the Netherlands) in the fluorescent imaging plate reader (FLIPR, Molecular Devices, Sunnyvale, USA), as described below.

The present invention further provides a process for preparing inventive compounds of the above-specified general formula I, according to which at least one compound of the general formula II

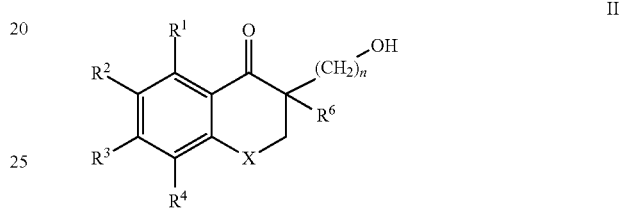

in which X, n and $R^1$ to $R^4$ are each as defined above and $R^6$ is a hydrogen radical, $—(CH_2)_q—NH_2$ or $—(CH_2)_q—OR^{25}$, where q and $R^{25}$ are each as defined above, in a reaction medium, optionally in the presence of at least one base, preferably in the presence of at least one organic base, is reacted with at least one compound of the general formula $R^5—N=C=O$ and optionally at least one compound of the general formula $R^{24}—N=C=O$, where $R^5$ and $R^{24}$ are defined identically as above, to give at least one compound of the general formula Ia

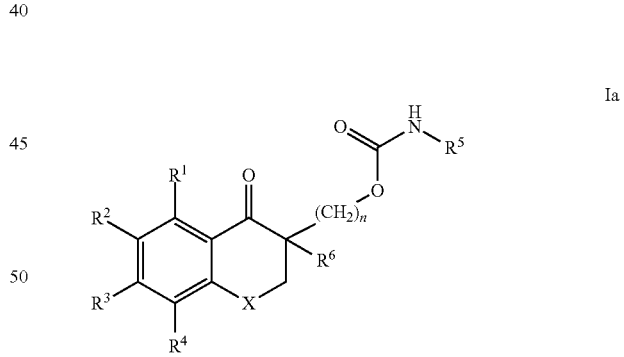

in which X, n and $R^1$ to $R^5$ are each as defined above and $R^6$ is a hydrogen radical, is $—(CH_2)_p—O—C(=O)—N(H)—R^{24}$, is $—(CH_2)_p—N(H)—C(=O)—N(H)—R^{24}$ or is $—(CH_2)_q—OR^{25}$; where p, q, $R^{24}$ and $R^{25}$ are each as defined above; and the latter is optionally purified and/or isolated; or at least one compound of the general formula II in which X, n and $R^1$ to $R^4$ are each as defined above and $R^6$ is a hydrogen radical or $—(CH_2)_q—OR^{25}$, where q and $R^{25}$ are each as defined above; in a reaction medium, optionally in the presence of at least one base, preferably in the presence of at least one organic base, is reacted with at least one compound of the general formula $R^5—S(=O)_2$-LG and optionally at least one compound of the general formula $R^{24}—S(=O)_2$-LG, where $R^5$ and $R^{24}$ are defined identically as above and LG is a leaving group, preferably a halogen atom, more preferably a chlorine atom, to give at least one compound of the general formula Ib,

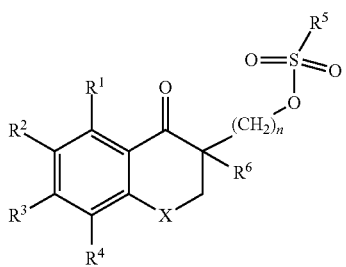

Ib in which X, n and $R^1$ to $R^5$ are each as defined above and $R^6$ is a hydrogen radical, is $-(CH_2)_p-O-S(=O)_2-R^{24}$ or is $-(CH_2)_q-OR^{25}$; where p, q, $R^{24}$ nd $R^{25}$ may each be as defined above; and the latter is optionally purified and/or isolated; or at least one compound of the general formula II in which X, n and $R^1$ to $R^4$ are each as defined above and $R^6$ is a hydrogen radical or $-(CH_2)_q-OR^{25}$ where q and $R^{25}$ are each as defined above; in a reaction medium, optionally in the presence of a base, preferably in the presence of at least one organic base, is reacted with at least one compound of the general formula $R^5-C(=O)$-LG and optionally at least one compound of the general formula $R^{24}-C(=O)$-LG, where $R^5$ and $R^{24}$ are optionally defined identically as above and LG is a leaving group, preferably a halogen atom, more preferably a chlorine atom, to give at least one compound of the general formula Ic

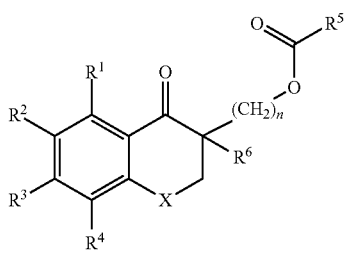

Ic in which X, n and $R^1$ to $R^5$ are each as defined above and $R^6$ is a hydrogen radical, is $-(CH_2)_p-O-C(=O)-R^{24}$ or is $-(CH_2)_q-OR^{25}$; where p, q, $R^{24}$ and $R^{25}$ are each as defined above; and the latter is optionally purified and/or isolated; or at least one compound of the general formula II in which X, n and $R^1$ to $R^4$ are each as defined above and $R^6$ is a hydrogen radical or $-(CH_2)_q-OR^{25}$ where q and $R^{25}$ are each as defined above; in a reaction medium, optionally in the presence of at least one base, preferably in the presence of at least one organic base, is reacted with at least one compound of the general formula $R^5-O-C(=O)$-LG and optionally at least one compound of the general formula $R^{24}-O-C(=O)$-LG, where $R^5$ and $R^{24}$ are defined identically as above and LG is a leaving group, preferably a halogen atom, more preferably a chlorine atom, to give at least one compound of the general formula Id

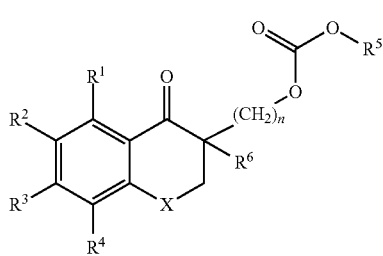

Id in which X, n and $R^1$ to $R^5$ are each as defined above and $R^6$ is a hydrogen radical, is $-(CH_2)_p-O-C(=O)-O-R^{24}$ or is $-(CH_2)_q-OR^{25}$; where p, q, $R^{24}$ and $R^{25}$ are each as defined above; and the latter is optionally purified and/or isolated; or at least one compound of the general formula II in which X, n and $R^1$ to $R^4$ are each as defined above and $R^6$ is a hydrogen radical, $-(CH_2)_q-NH_2$ or $-(CH_2)_q-OR^{25}$, where q and $R^{25}$ are each as defined above; in a reaction medium, in the presence of at least one base, preferably in the presence of at least one metal hydride salt, more preferably in the presence of potassium hydride and/or sodium hydride, is reacted with at least one compound of the general formula $R^5$-LG and optionally at least one compound of the general formula $R^{24}$-LG, where $R^5$ and $R^{24}$ are defined identically as above and LG is a leaving group, preferably a halogen atom, more preferably a chlorine atom, to give at least one compound of the general formula Ie,

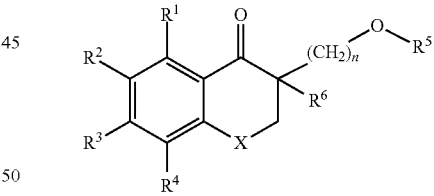

Ie in which X, n and $R^1$ to $R^5$ are each as defined above and $R^6$ is a hydrogen radical, is $-(CH_2)_p-OR^{24}$, is $-(CH_2)_p-NHR^{24}$ or is $-(CH_2)_q-OR^{25}$; where p, q, $R^{24}$ and $R^{25}$ are each as defined above; and the latter is optionally purified and/or isolated; or at least one compound of the general formula II in which X, n and $R^1$ to $R^4$ are each as defined above and $R^6$ is a hydrogen radical, $-(CH_2)_q-NH_2$ or $-(CH_2)_q-OR^{25}$, where q and $R^{25}$ are each as defined above, in a reaction medium, optionally in the presence of at least one base, preferably in the presence of at least one organic base, is reacted with at least one compound of the general formula $R^5-N=C=S$ and optionally at least one compound of the general formula $R^{24}-N=C=S$, where $R^5$ and $R^{24}$ may be defined identically as above, to give at least one compound of the general formula If

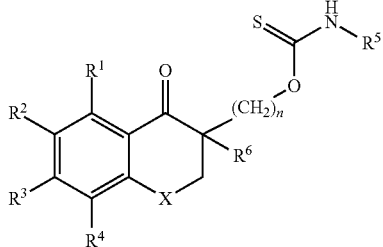

in which X, n and $R^1$ to $R^5$ are each as defined above and $R^6$ is a hydrogen radical, is —$(CH_2)_p$—O—C(=S)—N(H)—$R^{24}$, is —$(CH_2)_p$—N(H)—C(=S)—N(H)—$R^{24}$ or is —$(CH_2)_q$—$OR^{25}$; where p, q, $R^{24}$ and $R^{25}$ are each as defined above; and the latter is optionally purified and/or isolated; and optionally at least one compound of the general formula Ia, Ib, Ic, Id, Ie or If in which X, n and $R^1$ to $R^5$ are each as defined above and Y is O, O—C(=O), O—C(=O)—O, O—S(=O)$_2$, O—C(=S)—N(H) or O—C(=O)—N(H) and $R^6$ is —$(CH_2)_q$—$OR^{25}$ where $R^{25}$ is a hydrogen radical; in a reaction medium, optionally in the presence of at least one base, preferably in the presence of at least one organic base, is reacted with at least one compound of the general formula $R^{24}$—N=C=O to give at least one compound of the general formula Ia, Ib, Ic, Id or Ie in which X, n and $R^1$ to $R^5$ are each as defined above and Y is O, O—C(=O), O—C(=O)—O, O—S(=O)$_2$, O—C(=S)—N(H) or O—C(=O)—N(H) and $R^6$ is —$(CH_2)_p$—O—C(=O)—N(H)—$R^{24}$; and the latter is optionally purified and/or isolated;

or optionally at least one compound of the general formula Ia, Ib, Ic, Id, Ie or If in which X, n and $R^1$ to $R^5$ are each as defined above and Y is O, O—C(=O), O—C(=O)—O, O—S(=O)$_2$, O—C(=S)—N(H) or O—C(=O)—N(H) and $R^6$ is —$(CH_2)_q$—$OR^{25}$ where $R^{25}$ is a hydrogen radical; in a reaction medium, optionally in the presence of at least one base, preferably in the presence of at least one organic base, is reacted with at least one compound of the general formula $R^{24}$—S(=O)$_2$-LG to give at least one compound of the general formula Ia, Ib, Ic, Id or Ie in which X, n and $R^1$ to $R^5$ are each as defined above and Y is O, O—C(=O), O—C(=O)—O, O—S(=O)$_2$, O—C(=S)—N(H) or O—C(=O)—N(H) and $R^6$ is —$(CH_2)_p$—O—S(=O)$_2$—$R^{24}$; and the latter is optionally purified and/or isolated;

or optionally at least one compound of the general formula Ia, Ib, Ic, Id, Ie or If in which X, n and $R^1$ to $R^5$ are each as defined above and Y is O, O—C(=O), O—C(=O)—O, O—S(=O)$_2$, O—C(=S)—N(H) or O—C(=O)—N(H) and $R^6$ is —$(CH_2)_q$—$OR^{25}$ where $R^{25}$ is a hydrogen radical; in a reaction medium, optionally in the presence of at least one base, preferably in the presence of at least one organic base, is reacted with at least one compound of the general formula $R^{24}$—C(=O)-LG to give at least one compound of the general formula Ia, Ib, Ic, Id or Ie in which X, n and $R^1$ to $R^5$ are each as defined above and Y is O, O—C(=O), O—C(=O)—O, O—S(=O)$_2$, O—C(=S)—N(H) or O—C(=O)—N(H) and $R^6$ is —$(CH_2)_p$—O—C(=O)—$R^{24}$; and the latter is optionally purified and/or isolated;

or optionally at least one compound of the general formula Ia, Ib, Ic, Id, Ie or If in which X, n and $R^1$ to $R^5$ are each as defined above and Y is O, O—C(=O), O—C(=O)—O, O—S(=O)$_2$, O—C(=S)—N(H) or O—C(=O)—N(H) and $R^6$ is —$(CH_2)_q$—$OR^{25}$ where $R^{25}$ is a hydrogen radical; in a reaction medium, optionally in the presence of at least one base, preferably in the presence of at least one organic base, is reacted with at least one compound of the general formula $R^{24}$—O—C(=O)-LG to give at least one compound of the general formula Ia, Ib, Ic, Id or Ie in which X, n and $R^1$ to $R^5$ are each as defined above and Y is O, O—C(=O), O—C(=O)—O, O—S(=O)$_2$, O—C(=S)—N(H) or O—C(=O)—N(H) and $R^6$ is —$(CH_2)_p$—O—C(=O)—O—$R^{24}$; and the latter is optionally purified and/or isolated;

or optionally at least one compound of the general formula Ia, Ib, Ic, Id, Ie or If in which X, n and $R^1$ to $R^5$ are each as defined above and Y is O, O—C(=O), O—C(=O)—O, O—S(=O)$_2$, O—C(=S)—N(H) or O—C(=O)—N(H) and $R^6$ is —$(CH_2)_q$—$OR^{25}$ where $R^{25}$ is a hydrogen radical; in a reaction medium, in the presence of at least one base, preferably in the presence of at least one metal hydride salt, more preferably in the presence of potassium hydride and/or sodium hydride, is reacted with at least one compound of the general formula $R^{24}$-LG to give at least one compound of the general formula Ia, Ib, Ic, Id or Ie in which X, n and $R^1$ to $R^5$ are each as defined above and Y is O, O—C(=O), O—C(=O)—O, O—S(=O)$_2$, O—C(=S)—N(H) or O—C(=O)—N(H) and $R^6$ is —$(CH_2)_p$—O—$R^{24}$; and the latter is optionally purified and/or isolated; or optionally at least one compound of the general formula Ia, Ib, Ic, Id, Ie or If in which X, n and $R^1$ to $R^5$ are each as defined above and Y is O, O—C(=O), O—C(=O)—O, O—S(=O)$_2$, O—C(=S)—N(H) or O—C(=O)—N(H) and $R^6$ is —$(CH_2)_q$—$OR^{25}$ where $R^{25}$ is a hydrogen radical; in a reaction medium, optionally in the presence of at least one base, preferably in the presence of at least one organic base, is reacted with at least one compound of the general formula $R^{24}$—N=C=S to give at least one compound of the general formula Ia, Ib, Ic, Id or Ie; in which X, n and $R^1$ to $R^5$ are each as defined above and Y is O, O—C(=O), O—C(=O)—O, O—S(=O)$_2$, O—C(=S)—N(H) or O—C(=O)—N(H) and $R^6$ is —$(CH_2)_p$—O—C(=S)—N(H)—$R^{24}$; and the latter is optionally purified and/or isolated;

or optionally at least one compound of the general formula Ia, Ib, Ic, Id, Ie or If in which X, n and $R^1$ to $R^5$ are each as defined above and Y is O, O—C(=O), O—C(=O)—O, O—S(=O)$_2$, O—C(=S)—N(H) or O—C(=O)—N(H) and $R^6$ is —$(CH_2)_p$—$NH_2$; in a reaction medium, optionally in the presence of at least one base, preferably in the presence of at least one organic base, is reacted with at least one compound of the general formula $R^{24}$—N=C=S to give at least one compound of the general formula Ia, Ib, Ic, Id or Ie in which X, n and $R^1$ to $R^5$ are each as defined above and Y is O, O—C(=O), O—C(=O)—O, O—S(=O)$_2$, O—C(=S)—N (H) or O—C(=O)—N(H) and $R^6$ is —$(CH_2)_p$—N—C(=S)—N(H)—$R^{24}$; and the latter is optionally purified and/or isolated;

or optionally at least one compound of the general formula Ia, Ib, Ic, Id, Ie or If in which X, n and $R^1$ to $R^5$ are each as defined above and Y is O, O—C(=O), O—C(=O)—O, O—S(=O)$_2$, O—C(=S)—N(H) or O—C(=O)—N(H) and $R^6$ is —$(CH_2)_p$—$NH_2$; in a reaction medium, optionally in the presence of at least one base, preferably in the presence of at least one organic base, is reacted with at least one compound of the general formula $R^{24}$—N=C=O to give at least one compound of the general formula Ia, Ib, Ic, Id or Ie in which X, n and $R^1$ to $R^5$ are each as defined above and Y is O, O—C(=O), O—C(=O)—O, O—S(=O)$_2$, O—C(=S)—N (H) or O—C(=O)—N(H) and $R^6$ is —$(CH_2)_p$—N—C(=O)—N(H)—$R^{24}$; and the latter is optionally purified and/or isolated;

or optionally at least one compound of the general formula Ia, Ib, Ic, Id, Ie or If in which X, n and $R^1$ to $R^5$ are each as defined above and Y is O, O—C(=O), O—C(=O)—O, O—S(=O)$_2$, O—C(=S)—N(H) or O—C(=O)—N(H) and $R^6$ is —(CH$_2$)$_p$—NH$_2$; in a reaction medium, in the presence of at least one base, preferably in the presence of at least one metal hydride salt, more preferably in the presence of potassium hydride and/or sodium hydride, is reacted with at least one compound of the general formula $R^{24}$-LG to give at least one compound of the general formula Ia, Ib, Ic, Id or Ie; in which X, n and $R^1$ to $R^5$ are each as defined above and Y is O, O—C(=O), O—C(=O)—O, O—S(=O)$_2$, O—C(=S)—N(H) or O—C(=O)—N(H) and $R^6$ is —(CH$_2$)$_p$—N(H)—$R^{24}$; and the latter is optionally purified and/or isolated;

and optionally at least one compound of the general formula Ia, Ib, Ic, Id, Ie or If in which n, $R^1$ to $R^6$ and Y are each as defined above and X is S in a reaction medium, in the presence of sodium metaperiodate, is converted to at least one compound of the general formula Ia, Ib, Ic, Id or Ie in which n, $R^1$ to $R^6$ and Y are each as defined above and X is S(=O); and the latter is optionally purified and/or isolated;

and optionally at least one compound of the general formula Ia, Ib, Ic, Id, Ie or If, in which n, $R^1$ to $R^6$ and Y are each as defined above and X is S in a reaction medium, in the presence of hydrogen peroxide and acetic acid, is converted to at least one compound of the general formula Ia, Ib, Ic, Id or Ie in which n, $R^1$ to $R^6$ and Y are each as defined above and X is S(=O)$_2$; and the latter is optionally purified and/or isolated.

The present invention further provides a process for preparing inventive compounds of the above-specified formula I, according to which at least one compound of the general formula III

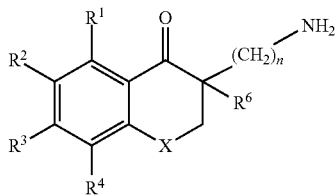

III in which X, n and $R^1$ to $R^4$ are each as defined above and $R^6$ is a hydrogen radical or is —(CH$_2$)$_p$—NH$_2$ where q is as defined above in a reaction medium, optionally in the presence of at least one base, preferably in the presence of at least one organic base, is reacted with at least one compound of the general formula $R^5$—N=C=O and optionally at least one compound of the general formula $R^{24}$—N=C=O, where $R^5$ and $R^{24}$ are defined identically as above to give at least one compound of the general formula Ig

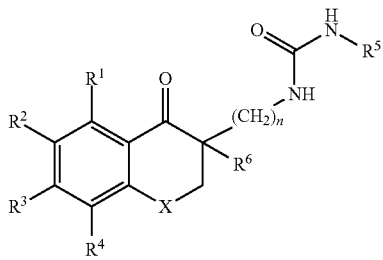

Ig in which X, n and $R^1$ to $R^5$ are each as defined above and $R^6$ is a hydrogen radical or is —(CH$_2$)$_p$—N(H)—C(=O)—N(H)—$R^{24}$ where p and $R^{24}$ are each as defined above; and the latter is optionally purified and/or isolated;

or at least one compound of the general formula III in a reaction medium, optionally in the presence of at least one base, preferably in the presence of at least one organic base, is reacted with at least one compound of the general formula $R^5$—N=C=S and optionally at least one compound of the general formula $R^{24}$—N=C=S, where $R^5$ and $R^{24}$ are defined identically as above, to give at least one compound of the general formula Ih

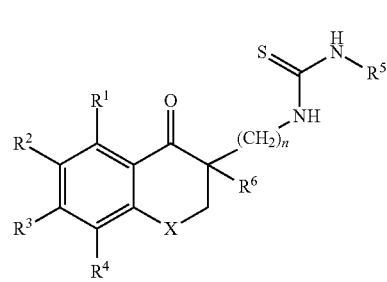

Ih in which X, n and $R^1$ to $R^5$ are each as defined above and $R^6$ is a hydrogen radical or is —(CH$_2$)$_p$—N(H)—C(=S)—N(H)—$R^{24}$ where p and $R^{24}$ are each as defined above; and the latter is optionally purified and/or isolated;

or at least one compound of the general formula III in a reaction medium, in the presence of at least one base, preferably in the presence of at least one metal hydride salt, more preferably in the presence of sodium hydride and/or potassium hydride, is reacted with a least one compound of the general formula $R^5$-LG and optionally at least one compound of the general formula $R^{24}$-LG, where $R^5$ and $R^{24}$ are defined identically as above and LG is a leaving group, preferably a halogen atom, more preferably a chlorine atom, to give at least one compound of the general formula Ik

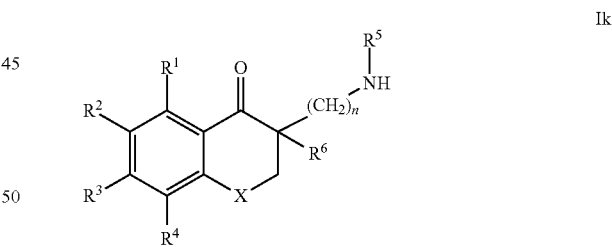

Ik in which X, n and $R^1$ to $R^5$ are each as defined above and $R^6$ is a hydrogen radical or is —(CH$_2$)$_p$— $R^{24}$ where p and $R^{24}$ are each as defined above; and the latter is optionally purified and/or isolated;

or optionally at least one compound of the general formula Ig, Ih or Ik in which X, n and $R^1$ to $R^5$ are each as defined above and Y is N(H), N(H)—C(=O)—N(H) or N(H)—C(=S)—N(H) and $R^6$ is —(CH$_2$)$_p$—NH$_2$; in a reaction medium, optionally in the presence of at least one base, preferably in the presence of at least one organic base, is reacted with at least one compound of the general formula $R^{24}$—N=C=O to give at least one compound of the general formula Ig, Ih or Ik in which X, n and $R^1$ to $R^5$ are each as defined above and Y is N(H), N(H)—C(=O)—N(H) or N(H)—C(=S)—N(H)

and R⁶ is —(CH₂)ₚ—N(H)—C(=O)—N(H)—R²⁴; and the latter is optionally purified and/or isolated;

or optionally at least one compound of the general formula Ig, Ih or Ik in which X, n and R¹ to R⁵ are each as defined above and Y is N(H), N(H)—C(=O)—N(H) or N(H)—C(=S)—N(H) and R⁶ is —(CH₂)ₚ—NH₂; in a reaction medium, optionally in the presence of at least one base, preferably in the presence of at least one organic base, is reacted with at least one compound of the general formula R²⁴—N=C=S to give at least one compound of the general formula Ig, Ih or Ik in which X, n and R¹ to R⁵ are each as defined above and Y is N(H), N(H)—C(=O)—N(H) or N(H)—C(=S)—N(H) and R⁶ is —(CH₂)ₚ—N(H)—C(=S)—N(H)—R²⁴; and the latter is optionally purified and/or isolated;

or optionally at least one compound of the general formula Ig, Ih or Ik in which X, n and R¹ to R⁵ are each as defined above and Y is N(H), N(H)—C(=O)—N(H) or N(H)—C(=S)—N(H) and R⁶ is —(CH₂)ₚ—NH₂; in a reaction medium, in the presence of at least one base, preferably in the presence of at least one metal hydride salt, more preferably in the presence of potassium hydride and/or sodium hydride, is reacted with at least one compound of the general formula R²⁴-LG to give at least one compound of the general formula Ig, Ih or Ik in which X, n and R¹ to R⁵ are each as defined above and Y is N(H), N(H)—C(=O)—N(H) or N(H)—C(=S)—N(H) and R⁶ is —(CH₂)ₚ—N(H)—R²⁴; and the latter is optionally purified and/or isolated;

and optionally at least one compound of the general formula Ig, Ih or Ik in which n, R¹ to R⁶ and Y are each as defined above and X is S in a reaction medium in the presence of sodium metaperiodate is converted to at least one compound of the general formula Ia, Ib, Ic, Id or Ie in which n, R¹ to R⁶ and Y are each as defined above and X is S(=O); and the latter is optionally purified and/or isolated;

and optionally at least one compound of the general formula Ig, Ih or Ik in which n, R¹ to R⁶ and Y are each as defined in one or more of claims 1 to 14 and X is S in a reaction medium in the presence of hydrogen peroxide and acetic acid is converted to at least one compound of the general formula Ia, Ib, Ic, Id or Ie in which n, R¹ to R⁶ and Y are each as defined in one or more of claims 1 to 14 and X is S(=O)₂; and the latter is optionally purified and/or isolated.

The reaction of compounds of the general formulae II, III, Ia, Ib, Ic, Id, Ie, If, Ig, Ih and Ik with isocyanates or isothiocyanates of the general formulae R⁵—N=C=O, R⁵—N=C=S, R²⁴—N=C=O and R²⁴—N=C=S is effected in a reaction medium, preferably selected from the group consisting of acetonitrile, tetrahydrofuran, toluene, benzene, ethanol, methanol, water and corresponding mixtures, optionally in the presence of at least one base, preferably in the presence of at least one base selected from the group consisting of triethylamine, N-methylmorpholine, pyridine, 4,4-dimethylamino-pyridine and diisopropylethylamine, at temperatures between 0° C. and 100° C.

The reaction of compounds of the general formulae II, III, Ia, Ib, Ic, Id, Ie, If, Ig, Ih and Ik with carboxylic acid derivatives, carbonic acid derivatives or sulfonic acid derivatives of the general formulae R⁵—C(=O)-LG, R²⁴—C(=O)-LG, R⁵—O—C(=O)-LG, R²⁴—O—C(=O)-LG, R⁵—S(=O)₂-LG and R²⁴—S(=O)₂-LG is effected in a reaction medium, preferably selected from the group consisting of diethyl ether, pyridine, tetrahydrofuran, acetonitrile, methanol, ethanol, dimethylformamide, dichloromethane and corresponding mixtures, optionally in the presence of an organic base, preferably selected from the group consisting of triethylamine, 4,4-dimethylaminopyridine, pyridine and diisopropylethylamine, or of an inorganic base, at temperatures of preferably from −70° C. to 100° C.

The reaction of compounds of the general formulae II, III, Ia, Ib, Ic, Id, Ie, If, Ig, Ih and Ik with compounds of the general formulae R⁵-LG and R²⁴-LG is effected in a reaction medium, preferably selected from the group consisting of dichloromethane, toluene, tetrahydrofuran, acetonitrile, diethyl ether, dioxane and corresponding mixtures, optionally in the presence of at least one base, preferably in the presence of at least one metal hydride salt, more preferably in the presence of sodium hydride and/or potassium hydride.

The compounds of the general formula II can be obtained as described in scheme 1.

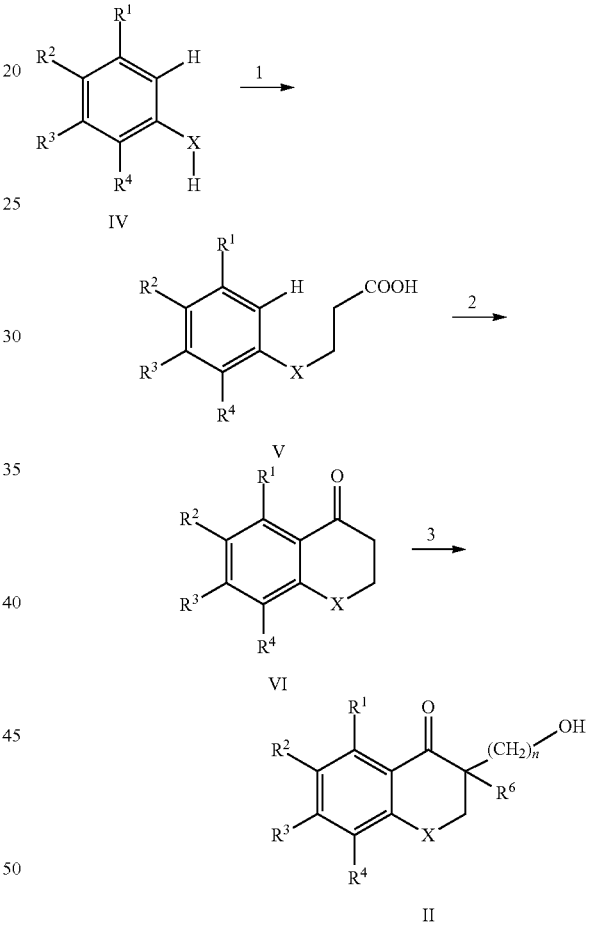

Scheme 1.

In stage 1, compounds of the general formula IV in which R¹ to R⁴ are each as defined above and X is O, S, N(H), N(R⁷), N[C(=O)—R⁸] or N[C(=O)—O—R⁹] are reacted in a reaction medium selected from the group consisting of tetrahydrofuran, dimethylformamide, dichloromethane, toluene, diethyl ether and corresponding mixtures, in the presence of at least one base, preferably of at least one organic base selected from the group consisting of triethylamine, N-methylmorpholine, diisopropylethylamine and pyridine, with acrylic acid [CH₂=CH—C(=O)—OH] at temperatures between 0° C. and 80° C., to compounds of the general formula V in which R¹ to R⁴ are each as defined above and X is O, S, N(H), N(R⁷), N[C(=O)—R⁸] or N[C(=O)—O—R⁹].

In stage 2, compounds of the general formula V in which $R^1$ to $R^4$ are each as defined above and X is $CH_2$, O, S, N(H), $N(R^7)$, $N[C(=O)-R^8]$ or $N[C(=O)-O-R^9]$ are converted in an acidic reaction medium, preferably in an acidic reaction medium selected from the group consisting of sulfuric acid and polyphosphoric acid, more preferably in polyphosphoric acid, at temperatures between 20° C. and 100° C. to compounds of the general formula VI, in which $R^1$ to $R^4$ are each as defined above and X is $CH_2$, O, S, N(H), $N(R^7)$, $N[C(=O)-R^8]$ or $N[C(=O)-O-R^9]$.

In stage 3 compounds of the general formula VI in which $R^1$ to $R^4$ are each as defined above and X is $CH_2$, O, S, N(H), $N(R^7)$, $N[C(=O)-R^8]$ or $N[C(=O)-O-R^9]$ from tetrahydrofuran, methanol, ethanol, isopropanol, water, dimethylformamide, dichloromethane, toluene, diethyl ether and corresponding mixtures in the presence of at least one base, preferably in the presence of at least one inorganic base, more preferably in the presence of potassium carbonate, sodium carbonate, lithium carbonate and magnesium carbonate, are reacted with formaldehyde, a formaldehyde equivalent or aqueous formalin solution at temperatures between 20° C. and 80° C. to give compounds of the general formula II in which $R^1$ to $R^4$ and $R^6$ are each as defined above, n is 1 and X is $CH_2$, O, S, N(H), $N(R^7)$, $N[C(=O)-R^8]$ or $N[C(=O)-O-R^9]$.

Optionally, compounds of the general formula II in which $R^1$ to $R^4$ and $R^6$ are each as defined above, n is 1 and X is S, in a reaction medium, preferably in a reaction medium selected from the group consisting of methanol, ethanol, isopropanol, water and corresponding mixtures, at temperatures between 0° C. and 50° C., are reacted with sodium metaperiodate to give compounds of the general formula II in which $R^1$ to $R^4$ and $R^6$ are each as defined above, n is 1 and X is S(=O).

Optionally, compounds of the general formula II in which $R^1$ to $R^4$ and $R^6$ are each as defined above, n is 1 and X is S, in a reaction medium, preferably in a reaction medium selected from the group consisting of methanol, ethanol, isopropanol, water and corresponding mixtures, at temperatures between 0° C. and 100° C., are reacted with acetic acid and with aqueous hydrogen peroxide solution to give compounds of the general formula II in which $R^1$ to $R^4$ and $R^6$ are each as defined above, n is 1 and X is $S(=O)_2$.

The compounds of the above-specified formulae IV, V, VI, $R^5-N=C=O$, $R^5-N=C=S$, $R^{24}-N=C=O$, $R^{24}-N=C=S$, $R^5-C(=O)$-LG, $R^{24}-C(=O)$-LG, $R^5-O-C(=O)$-LG, $R^{24}-O-C(=O)$-LG, $R^5-S(=O)_2$-LG, $R^{24}-S(=O)_2$-LG, $R^5$-LG and $R^{24}$-LG may in each case be available on the market and may also be prepared by customary processes known to those skilled in the art.

The above-described reactions may each be carried out under the customary conditions familiar to those skilled in the art, for example with regard to pressure or sequence of addition of the components. Optionally, the process regime which is optimal under the particular conditions can be determined by the person skilled in the art by simple preliminary experiments. The intermediates and end products obtained by the above-described reactions may in each case, if desired and/or necessary, be purified and/or isolated by customary methods known to those skilled in the art. Suitable purification processes are, for example, extraction processes and chromatographic processes such as column chromatography or preparative chromatography. All of the aforementioned process steps, and in each case also the purification and/or isolation of intermediates or end products, can be performed partly or completely under an inert gas atmosphere, preferably under a nitrogen atmosphere.

The inventive substituted benzofused cyclohexanone derivatives of the aforementioned general formulae I, Ia Ib, Ic, Id, Ie, If, Ig, Ih and Ik, referred to hereinafter only as benzofused cyclohexanone derivatives of the general formula I, and corresponding stereoisomers, may be obtained in the form of their free bases, of their free acids or else in the form of corresponding salts, especially physiologically compatible salts. The free bases of the particular inventive substituted benzofused cyclohexanone derivatives of the aforementioned general formula I and corresponding stereoisomers may, for example, be converted to the corresponding salts, preferably physiologically compatible salts, by reaction with an inorganic or organic acid, preferably with hydrochloric acid, hydrobromic acid, sulfuric acid, phosphoric acid, methanesulfonic acid, p-toluenesulfonic acid, carbonic acid, formic acid, acetic acid, oxalic acid, succinic acid, tartaric acid, mandelic acid, fumaric acid, lactic acid, citric acid, glutamic acid or aspartic acid. The free bases of the particular benzofused cyclohexanone derivatives of the aforementioned general formula I and corresponding stereoisomers can likewise be converted to the corresponding physiologically compatible salts with the free acid or a salt of a sugar substitute, for example saccharin, cyclamate or acesulfame.

Accordingly, the free acids of the substituted benzofused cyclohexanone derivatives of the aforementioned general formula I and corresponding stereoisomers can be converted to the corresponding physiologically compatible salts by reaction with a suitable base. Examples include the alkali metal salts, alkaline earth metal salts or ammonium salts $[NH_x R_{4-x}]^+$ in which x=0, 1, 2, 3 or 4 and R is a linear or branched $C_{1-4}$-alkyl radical.

The inventive substituted benzofused cyclohexanone derivatives of the aforementioned general formula I and corresponding stereoisomers may optionally, just like the corresponding acids, the corresponding bases or salts of these compounds, also be obtained in the form of their solvates, preferably in the form of their hydrates, by customary methods known to those skilled in the art.

When the inventive substituted benzofused cyclohexanone derivatives of the aforementioned general formula I, after they have been prepared, are obtained in the form of a mixture of their stereoisomers, preferably in the form of their racemates or other mixtures of their different enantiomers and/or diastereomers, they can be separated and optionally isolated by customary processes known to those skilled in the art. Examples include chromatographic separation processes, especially liquid chromatography processes under standard pressure or under elevated pressure, preferably MPLC and HPLC processes, and processes for fractional crystallization. It is possible especially to separate individual enantiomers from one another, for example by means of HPLC on a chiral stationary phase, or, by means of crystallization with diastereomeric salts formed with chiral acids, for instance (+)-tartaric acid, (−)-tartaric acid or (+)-10-camphorsulfonic acid.

The inventive substituted benzofused cyclohexanone derivatives of the aforementioned general formula I and corresponding stereoisomers, and also in each case the corresponding acids, bases, salts and solvates, are toxicologically safe and are therefore suitable as active pharmaceutical ingredients in medicaments.

The present invention therefore further provides a medicament comprising at least one substituted benzofused cyclohexanone derivative of the above-specified general formula I including the compounds excluded above, in each case optionally in the form of its pure stereoisomers, especially enantiomers or diastereomers, of its racemates or in the form of a mixture of stereoisomers, especially of the enantiomers and/or diastereomers, in any mixing ratio, or in each case in the form of a corresponding salt, or in each case in the form of a corresponding solvate, and optionally one or more pharmaceutically compatible assistants.

These inventive medicaments are suitable especially for vanilloid receptor 1 (VR1/TRPV1) regulation, especially for vanilloid receptor 1 (VR1/TRPV1) inhibition and/or for vanilloid receptor 1 (VR1/TRPV1) stimulation. In addition, the inventive medicaments are suitable for CB1 receptor regulation and/or for CB2 receptor regulation.

The inventive medicaments are likewise suitable with preference for prophylaxis and/or treatment of disorders or diseases which are mediated at least partly by vanilloid receptors 1, CB1 receptors and/or CB2 receptors.

The inventive medicament is suitable with preference for treatment and/or prophylaxis of one or more disorders selected from the group consisting of pain, preferably of pain selected from the group consisting of acute pain, chronic pain, neuropathic pain and visceral pain; joint pain; migraine; depression; neuropathy; neural injuries; neurodegenerative disorders, preferably selected from the group consisting of multiple sclerosis, Alzheimer's disease, Parkinson's disease and Huntington's disease; cognitive dysfunctions, preferably cognitive deficiencies, more preferably memory impairments; epilepsy; respiratory pathway disorders, preferably selected from the group consisting of asthma and lung inflammation; coughing; urine incontinence; an overactive bladder (OAB); stomach ulcers; irritable bowel syndrome; stroke; eye irritations; skin irritations; neurotic skin disorders; inflammation disorders, preferably inflammation of the intestine; diarrhea; pruritus; disorders of food uptake, preferably selected from the group consisting of bulimia, cachexia, anorexia and obesity; medicament dependence; medicament abuse; withdrawal symptoms in the case of medicament dependence; evolution of tolerance to medicaments, preferably to natural or synthetic opioids; drug dependence; drug abuse; withdrawal symptoms in the case of drug dependence; alcohol dependence; alcohol abuse and withdrawal symptoms in the case of alcohol dependence; for diuresis; for antinatriuresis; to influence the cardiovascular system; to enhance vigilance; to enhance libido; to modulate movement activity; for anxiolysis; for local anesthesia and/or to inhibit undesired side effects, preferably selected from the group consisting of hyperthermia, hypertension and narrowing of the bronchia, triggered by the administration of vanilloid receptor 1 (VR1/TRPV1 receptors) agonists, preferably selected from the group consisting of capsaicin, resiniferatoxin, olvanil, arvanil, SDZ-249665, SDZ-249482, nuvanil and capsavanil.

The inventive medicament is particularly suitable for treatment and/or prophylaxis of one or more disorders selected from the group consisting of pain, preferably from pain selected from the group consisting of acute pain, chronic pain, neuropathic pain and visceral pain; migraine; depression; neurodegenerative disorders, preferably selected from the group consisting of multiple sclerosis, Alzheimer's disease, Parkinson's disease and Huntington's disease; cognitive dysfunctions, preferably cognitive deficiencies, more preferably memory impairments; urine incontinence; an overactive bladder (OAB); medicament dependence, medicament abuse; withdrawal symptoms in the case of medicament dependence; evolution of tolerance to medicaments, preferably evolution of tolerance to natural or synthetic opioids; drug dependence; drug abuse; withdrawal symptoms in the case of drug dependence; alcohol dependence; alcohol abuse and withdrawal symptoms in the case of alcohol dependence.

The inventive medicament is very particularly suitable for treatment and/or prophylaxis of pain, preferably of pain selected from the group consisting of acute pain, chronic pain, neuropathic pain and visceral pain, and/or urine incontinence.

The present invention further provides for the use of at least one inventive compound and optionally of one or more pharmaceutically compatible assistants for producing a medicament for vanilloid receptor 1 (VR1/TRPV1) regulation, preferably for vanilloid receptor 1 (VR1/TRPV1) inhibition and/or for vanilloid receptor 1 (VR1/TRPV1) stimulation, for CB1 receptor regulation and/or for CB2 receptor regulation.

Preference is given to the use of at least one inventive compound and optionally of one or more pharmaceutically compatible assistants for producing a medicament for prophylaxis and/or treatment of disorders or diseases which are mediated at least partly by vanilloid receptors 1, CB1 receptors and/or CB2 receptors.

Particular preference is given to the use of at least one inventive compound and optionally of one or more pharmaceutically compatible assistants for producing a medicament for treatment and/or prophylaxis of one or more disorders selected from the group consisting of pain, preferably of pain selected from the group consisting of acute pain, chronic pain, neuropathic pain and visceral pain; joint pain; migraine; depression; neuropathy; neural injuries; neurodegenerative disorders, preferably selected from the group consisting of multiple sclerosis, Alzheimer's disease, Parkinson's disease and Huntington's disease; cognitive dysfunctions, preferably cognitive deficiencies, more preferably memory impairments; epilepsy; respiratory pathway disorders, preferably selected from the group consisting of asthma and lung inflammation; coughing; urine incontinence; an overactive bladder (OAB); stomach ulcers; irritable bowel syndrome; stroke; eye irritations; skin irritations; neurotic skin disorders; inflammation disorders, preferably inflammation of the intestine; diarrhea; pruritus; disorders of food uptake, preferably selected from the group consisting of bulimia, cachexia, anorexia and obesity; medicament dependence; medicament abuse; withdrawal symptoms in the case of medicament dependence; evolution of tolerance to medicaments, preferably to natural or synthetic opioids; drug dependence; drug abuse; withdrawal symptoms in the case of drug dependence; alcohol dependence; alcohol abuse and withdrawal symptoms in the case of alcohol independence; for diuresis; for antinatriuresis; to influence the cardiovascular system; to enhance vigilance; to enhance libido; to modulate movement activity; for anxiolysis; for local anesthesia and/or to inhibit undesired side effects, preferably selected from the group consisting of hyperthermia, hypertension and narrowing of the bronchia, triggered by the administration of vanilloid receptor 1 (VR1/TRPV1 receptors) agonists, preferably selected from the group consisting of capsaicin, resiniferatoxin, olvanil, arvanil, SDZ-249665, SDZ-249482, nuvanil and capsavanil.

Very particular preference is given to the use of at least one inventive compound and optionally of one or more pharmaceutically compatible assistants for producing a medicament for treatment and/or prophylaxis of one or more disorders selected from the group consisting of pain, preferably from pain selected from the group consisting of acute pain, chronic pain, neuropathic pain and visceral pain; migraine; depression; neurodegenerative disorders, preferably selected from the group consisting of multiple sclerosis, Alzheimer's disease, Parkinson's disease and Huntington's disease; cognitive dysfunctions, preferably cognitive deficiencies, more preferably memory impairments; urine incontinence; an overactive bladder (OAB); medicament dependence; medicament abuse; withdrawal symptoms in the case of medicament dependence; evolution of tolerance to medicaments, preferably evolution of tolerance to natural or synthetic opioids; drug dependence; drug abuse; withdrawal symptoms in the case of drug dependence; alcohol dependence; alcohol abuse and withdrawal symptoms in the case of alcohol dependence.

Ever more preferred is the use of at least one inventive compound and optionally of one or more pharmaceutically compatible assistants for producing a medicament for treatment and/or prophylaxis of pain, preferably selected from the group consisting of acute pain, chronic pain, neuropathic pain and visceral pain, and/or urine incontinence.

The inventive medicament is suitable for administration to adults and children, including infants and babies. The inventive medicament may be present as a liquid, semisolid or solid medicament form, for example in the form of injection solutions, drops, juices, syrups, sprays, suspensions, tablets, patches, capsules, plasters, suppositories, ointments, creams, lotions, gels, emulsions, aerosols or in multiparticulate form, for example in the form of pellets or granules, optionally compressed to tablets, filled into capsules or suspended in a liquid, and may also be administered as such.

In addition to at least one substituted benzofused cyclohexanone derivative of the above-specified general formula I, optionally in the form of its pure stereoisomers, especially enantiomers or diastereomers, of its racemates or in the form of mixtures of the stereoisomers, especially of the enantiomers or diastereomers, in any mixing ratio, or optionally in the form of a corresponding salt or in each case in the form of a corresponding solvate, the inventive medicament typically comprises further physiologically compatible pharmaceutical assistants which may, for example, be selected from the group consisting of carrier materials, fillers, solvents, diluents, surfactants, dyes, preservatives, disintegrants, lubricants, aromas and binders.

The selection of the physiologically compatible assistants and the amounts thereof to be used depends upon whether the medicament is to be administered orally, subcutaneously, parenterally, intravenously, intraperitoneally, intradermally, intramuscularly, intranasally, buccally, rectally or locally, for example to infections on the skin, the mucous membranes and in the eyes. For oral application, suitable formulations are preferably those in the form of tablets, coated tablets, capsules, granules, pellets, drops, juices and syrups; suitable formulations for parenteral, topical and inhalative application are preferably solutions, suspensions, readily reconstitutable dry formulations and sprays. The inventive substituted benzofused cyclohexanone derivatives used in the inventive medicament may, in a depot, in dissolved form or in a plaster, optionally with addition of skin penetration-promoting agents, are suitable percutaneous administration formulations. Orally or percutaneously applicable formulation forms may also release the particular inventive substituted benzofused cyclohexanone derivative in a retarded manner.

The inventive medicaments are produced with the aid of conventional means, apparatus, methods and processes known from the prior art, as described, for example, in "Remington's Pharmaceutical Sciences", editor A. R. Gennaro, 17th edition, Mack Publishing Company, Easton, Pa., 1985, more particularly in part 8, chapter 76 to 93. The corresponding description is hereby included as a reference and forms part of the disclosure. The amount of the particular inventive benzofused cyclohexanone derivatives of the above-specified general formula I to be administered to the patient may vary and is, for example, dependent on the weight or age of the patient and on the administration method, the indication and the severity of the disorder. Typically, from 0.001 to 100 mg/kg, preferably from 0.05 to 75 mg/kg, more preferably from 0.05 to 50 mg/kg, of body weight of the patient of at least one such inventive compound are administered.

Pharmacological Methods:
I. Functional Study on the Vanilloid Receptor 1 (VR1/TRPV1 Receptor)

The agonistic or antagonistic action of the substances to be studied on the vanilloid receptor 1 (VR1/TRPV1) of the rat species can be determined with the following assay. In this assay, the $Ca^{2+}$ current through the receptor channel is quantified with the aid of a $Ca^{2+}$-sensitive dye (Fluo-4 type, Molecular Probes Europe BV, Leiden the Netherlands) in a fluorescent imaging plate reader (FLIPR, Molecular Devices, Sunnyvale, USA).

Ia. Method:
Complete medium: 50 ml HAMS F12 Nutrient Mixture (Gibco Invitrogen GmbH, Karlsruhe, Germany) with
10% by volume of FCS (fetal calf serum, Gibco Invitrogen GmbH, Karlsruhe, Germany, heat-inactivated);
2 mM L-glutamine (Sigma, Munich, Germany);
1% by weight of AA solution (antibiotic/antimycotic solution, PAA, Pasching, Austria) and 25 ng/ml of NGF medium (2.5 S, Gibco Invitrogen GmbH, Karlsruhe, Germany)

Cell culture plate: poly-D-lysine-coated, black 96-hole plates with a clear bottom (96 well black/clear plate, BD Biosciences, Heidelberg, Germany) are additionally coated with laminin (Gibco Invitrogen GmbH, Karlsruhe, Germany) by diluting laminin to a concentration of 100 µg/ml with PBS (Ca—Mg-free PBS, Gibco Invitrogen GmbH, Karlsruhe, Germany). Aliquots having a concentration of 100 µg/ml of laminin are withdrawn and stored at −20° C. The aliquots are diluted with PBS in a ratio of 1:10 to 10 µg/ml of laminin and in each case 50 µl of the solution are pipetted into a well of the cell culture plate. The cell culture plates are incubated at 37° C. for at least two hours, the supernatant solution is removed by suction and the wells are each washed twice with PBS. The coated cell culture plates are stored with supernatant PBS which is not removed until directly before the application of the cells.

Preparation of the Cells:
The spinal column is removed from beheaded rats and placed directly into cold HBSS buffer (Hank's buffered saline solution, Gibco Invitrogen GmbH, Karlsruhe, Germany), i.e. placed in an ice bath, which has been admixed with 1% by volume of an AA solution (antibiotic/antimycotic solution, PAA, Pasching, Austria). The spinal column is severed longitudinally and removed from the spinal canal together with fasciae. Subsequently, the dorsal root ganglia (DRGs) are removed and in turn stored in cold HBSS buffer admixed with 1% by volume of an M solution. The DRGs freed completely of blood residues and spinal nerves are in each case transferred to 500 µl of cold type 2 collagenase (PAA, Pasching, Austria) and incubated at 37° C. for 35 minutes. After addition of 2.5% by volume of trypsin (PAA, Pasching, Austria), incubation is continued at 37° C. for a further 10 minutes. After complete incubation, the enzyme solution is cautiously pipetted off and the remaining DRGs are each admixed with 500 µl of complete medium.

The DRGs are each suspended repeatedly, drawn through cannulas No. 1, No. 12 and No. 16 by means of a syringe and transferred to 50 ml Falcon tubes which are made up to 15 ml with complete medium. The contents of each Falcon tube are in each case filtered through a 70 µm Falcon filter insert and centrifuged at 1200 revolutions and room temperature for 10 minutes. The resulting pellet is in each case taken up in 250 µl of complete medium and the cell count is determined.

The number of cells in the suspension is adjusted to 3 times $10^5$ per ml and in each case 150 μl of this suspension are added to one well of the cell culture plates coated as described above. In the incubator, the plates are left to stand at 37° C., 5% by volume of $CO_2$ and 95% relative air humidity for two to three days.

Subsequently, the cells are laden with 2 μM Fluo-4 and 0.01% by volume of Pluronic F127 (Molecular Probes Europe BV, Leiden, the Netherlands) in HBSS buffer (Hank's buffered saline solution, Gibco Invitrogen GmbH, Karlsruhe, Germany) at 37° C. for 30 min, washed 3× with HBSS buffer and, after a further incubation of 15 minutes, used in the FLIPR assay at room temperature for $Ca^{2+}$ measurement. The $Ca^{2+}$-dependent fluorescence is measured beforehand after addition of substances ($\lambda_{ex}$=488 nm, $\lambda_{em}$=540 nm). The quantification is effected by the measurement of the highest fluorescence intensity (FC, fluorescence counts) over the time.

Ib. Method:

Chinese hamster ovary cells (CHO K1 cells, European Collection of Cell Cultures (ECACC), England) are transfected stably with the human vanilloid receptor 1 (VR1) gene or the vanilloid receptor 1 (VR1) gene of the rat. For functional studies, these cells are plated out onto poly-D-lysine-coated black 96-well plates with a clear bottom (BD Biosciences, Heidelberg, Germany) in a density of 25 000 cells/well. The cells are incubated overnight at 37° C. and 5% $CO_2$ in culture medium (Ham's Nutrient Mixture F12, Gibco Invitrogen GmbH, Karlsruhe, Germany) with 10% by volume of FBS (fetal bovine serum, Gibco Invitrogen GmbH, Karlsruhe, Germany), and 18 μg/ml of L-proline (Gibco Invitrogen GmbH, Karlsruhe, Germany). The next day, the cells are laden with 2 μM Fluo-4 and 0.01% by volume of Pluronic F127 (Molecular Probes Europe BV, Leiden, The Netherlands) in HBSS buffer (Hank's buffered saline solution, Gibco Invitrogen GmbH, Karlsruhe, Germany) at 37° C. for 30 min. Subsequently, the plates are washed 3 times with HBSS buffer and, after a further incubation of 15 minutes at room temperature, used for $Ca^{2+}$ measurement in the FLIPR assay. The $Ca^{2+}$-dependent fluorescence is measured before and after addition of substances $\lambda_{ex}$=488 nm, $\lambda_{em}$=540 nm). The quantification is effected by measuring the highest fluorescence intensity (FC, fluorescence counts) over the time.

Ic. FLIPR Assay:

The FLIPR protocol consists of 2 substance additions. First, the compounds to be tested (10 μM) are pipetted onto the cells obtained according to Ia or Ib and the $Ca^{2+}$ current is compared with the control (capsaicin 10 μM). This gives rise to the result in % activation based on the $Ca^{2+}$ signal after addition of 10 μM capsaicin (CP). After incubation for 5 minutes, 100 nM capsaicin is applied and the current of $Ca^{2+}$ is likewise determined.

Desensitizing agonists and antagonists lead to a suppression in the $Ca^{2+}$ current. % inhibition is calculated compared to the maximum achievable inhibition with 10 μM capsaicin.

Triple determinations (n=3) are performed and they are repeated in at least 3 independent experiments (N=4).

II. Formalin Test on Mice

The test to determine the antinociceptive action of the inventive compounds is carried out in the formalin test on male mice (NMRI, body weight from 20 to 30 g, Iffa, Credo, Belgium).

In the formalin test, according to D. Dubuisson et al., Pain 1977, 4, 161-174, a distinction is drawn between the first (early) phase (from 0 to 15 minutes after the formalin injection) and the second (late) phase (from 15 to 60 minutes after the formalin injection). The early phase, as a direct reaction to the formalin injection, constitutes a model for acute pain, while the late phase is considered to be a model for persistent (chronic) pain (T. J. Coderre et al., Pain 1993, 52, 259-285). The corresponding literature descriptions are hereby included as a reference and form part of the disclosure.

The inventive compounds are tested in the second phase of the formalin test in order to obtain statements regarding substance effects on chronic/inflammatory pain.

According to the administration type of the inventive compounds, the administration time of the inventive compounds before the formalin injection is selected. The intravenous administration of 10 mg/kg of body weight of the test substances is effected 5 minutes before the formalin injection. This is done by a single subcutaneous formalin injection (20 μl, 1% aqueous solution) into the dorsal side of the right hind paw, such that a nociceptive reaction is induced in freely mobile test animals, which is manifested in obvious licking and biting of the paw affected.

Subsequently, for a test period of three minutes in the second (late) phase of the formalin test (from 21 to 24 minutes after the formalin injection), the nociceptive behavior is registered continuously by observing the animals. The pain behavior is quantified by summation of the seconds in which the animals exhibit licking and biting of the paw affected within the test period.

The comparison is in each case with control animals which, instead of the inventive compounds, receive vehicle (0.9% aqueous sodium chloride solution) before formalin administration. Based on the quantification of the pain behavior, the substance action in the formalin test is determined as the change relative to the corresponding control in percent.

After injection of substances which have antinociceptive activity in the formalin test, the behavior of the animals described, i.e. licking and biting, is reduced or eliminated.

III. Test for Analgesic Activity in the Writhing Test

The test of the inventive compounds of the general formula I for analgesic activity was carried out in phenylquinone-induced writhing in mice, modified according to I. C. Hendershot and J. Forsaith (1959), J. Pharmacol. Exp. Ther. 125, 237-240. The corresponding literature description is hereby included as a reference and forms part of the disclosure.

To this end, male NMRI mice with a weight of from 25 to 30 g were used. Groups of 10 animals per compound dose received, 10 minutes after intravenous administration of the compounds to be tested, 0.3 ml/mouse of a 0.02% aqueous solution of phenylquinone (phenylbenzoquinone, from Sigma, Deisenhofen, Germany; preparation of the solution with addition of 5% by weight of ethanol and storage in a water bath at 45° C.) which was applied intraperitoneally. The animals were placed individually into observation cages. With the aid of a push-button counter, the number of pain-induced stretching motions (so-called writhing reactions=arching of the back with stretching-out of the rear extremities) was counted for from 5 to 20 minutes after the phenylquinone administration. The control employed was animals which had received only physiological saline. All compounds were tested in the standard dosage of 10 mg/kg.

IV. Functional Study on the Human CB1 Receptor

Incubation and Washing Buffer:

50 mM TRIS (from Fluka, Cat. No. 93349); 2.5 mM EDTA (from Fluka Cat. No. 03680); 5 mM $MgCl_2$ (from Merck, Cat. No. 1.05833); 0.5 mg/ml BSA (from Sigma Cat. No. A-2153)

The pH of the buffer is adjusted to 7.4 at 4° C.

Medium for Softening the Filter Mats:

0.05% PEI (from Sigma, Cat. No. P-3143)

The membranes (RBHCB1M, from Perkin Elmer (human recombinant cell membranes)) were supplied in aliquots of 1 ml each in dry ice and stored at −80° C. The protein concentration of the batches was around 6 mg/ml. For the test, in each case 1 ml was thawed rapidly and diluted with 7 ml of incubation buffer (1:8). 20 μl of this dilution were used in the test. This corresponded to a protein content of approx. 15 μg in the batch.

Incubation Batch:

MTP from Costar® of the "U type" (assay MTP; Cat. No. 3794) was used. The pipetting sequence is reproduced in Table 1 below.

TABLE 1

| Substance | Molarity in the batch | μl | Protein in the batch |
|---|---|---|---|
| Incubatation buffer | — | 200 | — |
| Test substance or USB* | $10^{-5}$ M | 5 | — |
| Membrane | — | 20 | approx. 15 μg |
| [$^3$H]CP55,940 | 1 nM | 25 | — |

*USB (unspecific binding): WIN 55,212-mesylate (from Tocris, Cat. No. 1038) ($10^{-6}$ M in the batch)
[$^3$H] CP-55,940 (from Perkin Elmer Cat. No. 1051)

After the pipetting operation had ended, a lid was placed on the MTP and the incubation was effected at 25° C. for 90 min. Subsequently, the samples were removed by suction with the aid of a Brandel cell harvester (model MPXRI-96T) through a GF/B Unifilter MTP (from Packard, Cat. No. 6005177) presoftened with 0.05% PEI. The samples were washed twice with 200 ml of ice-cooled incubation buffer per 96-well MTP. Thereafter, the plate was dried in a drying cabinet +60° C. for 1 h. Subsequently, the bottom side of the MTP was sealed from the bottom exactly with a "back seal" from Packard. 35 μl of scintillator (Packard, "Ultima Gold"; Cat. No. 6013151) per well were pipetted thereto. In addition, the top side of the plate was now sealed with a "top seal" (from Packard; Cat. No. 6005185). After a wait time of 1 h, the plate was analyzed on a "Trilux" from Wallac.

V. Determination of the Affinity for the Cannabinoid Receptor CB2 (CB2 Receptor):

To determine the affinity of the inventive compounds for the cannabinoid receptor, membranes from human recombinant HEK-293EBNA cells were used, which had been transfected stably with the human CB2 receptor. The radioligand used was tritium-labeled 5-(1,1-dimethylheptyl)-2-(5-hydroxypropyl)cyclohexyl)-1-alpha,2-beta,5-alpha)phenol ([$^3$H]-CP 55,940 with 103.4 Ci/mmol, 1 mCi/ml). The determination was effected in a test buffer composed of 50 mM Tris-HCl, 2.5 mM EDTA, 5 mM MgCl$_2$ and 1.0 mg/ml of fatty acid-free BSA. The test substances were each dissolved in DMSO.

The affinity of the inventive compounds for the CB2 receptor is determined by their ability to displace [$^3$H]-CP 55,940 from CB2 receptors in membranes from HEK-293EBNA cells. To this end, in each case 8 μg of the membranes (20 μl of a solution from membranes in a concentration of 400 μg/ml) are incubated in wells on a microtiter plate with a 0.33 nM solution of [$^3$H]-CP 55,949 (120 Ci/mmol) in a total volume of test buffer of 200 μl at 30° C. for 90 minutes.

Subsequently, either the test substances or WIN 55212-2 to determine the unspecific binding, in each case dissolved in DMSO, are added to the wells so as to result in each case in a concentration of the corresponding substances of 10 μM. Incubation at 30° C. is continued for a further 40 minutes. The binding reaction was ended by rapid filtration through GF/C filter paper which had been treated with 0.05% PEI using a Brandel cell harvester with 96 wells. The filters are washed nine times with 0.5 ml of ice-cooled washing buffer (50 nM Tris-HCl, 5 mM MgCl$_2$, 2.5 mM EDTA, 2% BSA, pH 7.4), air-dried and placed in scintillation fluid, and the radioactivity is determined with the aid of a scintillation counter.

The percentage displacement of the radioactive ligand [$^3$H]-CP 55,940 from its binding to the CB2 receptor is reported as percent inhibition of the specific binding.

The invention will be illustrated hereinafter with the aid of some examples. These illustrations are merely by way of example and do not restrict the general concept of the invention.

EXAMPLES

The yields of the compounds prepared are not optimized.
All temperatures are uncorrected.
Abbreviations:
abs. absolute
aq. aqueous
eq. equivalent
DCM dichloromethane
DMAP 4-dimethylaminopyridine
DMF dimethylformamide
EtOAc ethyl acetate
sat. saturated
MeOH methanol
MTBE tert-butyl methyl ether
NMR nuclear resonance spectroscopy
RT room temperature
THF tetrahydrofuran The chemicals and solvents used were purchased commercially from the conventional suppliers (Acros, Avocado, Aldrich, Bachem, Fluka, Lancaster, Maybridge, Merck, Sigma, TCI, etc.) or synthesized by methods known to those skilled in the art.

The stationary phase used for the column chromatography was silica gel 60 (0.040-0.063 mm) from E. Merck, Darmstadt.

The thin layer chromatography analyses were carried out with ready-to-use HPTLC plates, silica gel 60 F 254, from E. Merck, Darmstadt.

The mixing ratios of solvents, eluents or for chromatographic analyses are always reported in volume/volume.

The analysis was effected by mass spectroscopy and NMR.

1. Synthesis of 3-phenylsulfanylpropionic acid

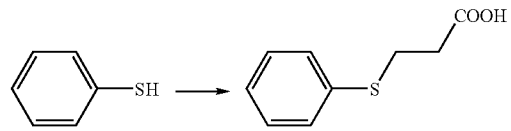

To a solution of thiophenol (8.87 g, 80.6 mmol) in THF (20 ml) and triethylamine (8.6 g, 11.9 ml, 85 mmol) was added dropwise, with ice cooling, acrylic acid (5.8 g, 5.5 ml, 81 mmol). The reaction mixture was stirred at 0° C. for 1 h and then at RT overnight, acidified with 2N hydrochloric acid and extracted with diethyl ether (2×100 ml). The combined organic phases were dried over sodium sulfate and the solvent was removed under reduced pressure. The desired 3-phenylsulfanylpropionic acid product (13.67 g, 93% of theory) was obtained as a white solid (m.p. 51-54° C.)

$^1$H NMR (DMSO-d$_6$) δ 2.53 (2H, t, J=7.1 Hz); 3.13 (2H, t, J=7.2 Hz); 7.18-7.23 (1H, m); 7.30-7.36 (4H, m); 12.31 (1H, br s)

2. Synthesis of thiochroman-4-one

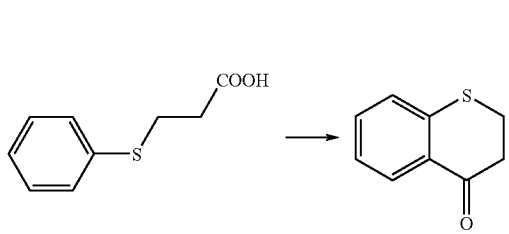

Polyphosphoric acid (110 g) was admixed with 3-phenylsulfanylpropionic acid (13.54 g, 74 mmol) and the reaction mixture was stirred at 60° C. for 96 h. After cooling to RT, the reaction mixture was admixed with water (250 ml) and extracted with diethyl ether (3×100 ml). The combined organic phases were washed with 5% eq. NaHCO$_3$ solution (50 ml), washed with water (50 ml) and dried over sodium sulfate, and the solvent was removed under reduced pressure. After column chromatography purification of the residue (silica gel, 8:1 cyclohexane/MTBE), the desired product was obtained as a greenish oil (8.0 g, 66% of theory).

$^1$H NMR (DMSO-d$_6$) δ 2.90 (2H, t, J=6.6 Hz); 3.32 (2H, t, J=6.3 Hz); 7.22 (1H, dd, J=8.1 and 8.1 Hz); 7.36 (1H, d, J=7.9 Hz); 7.47 (1H, dd, J=8.1 and 8.1 Hz); 7.96 (1H, d, J=8.1 Hz)

3. Synthesis of 3,3-bis(hydroxymethyl)thiochroman-4-one

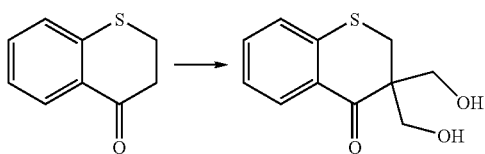

A solution of thiochroman-4-one (2.0 g, 12 mmol) in MeOH (40 ml) and water (8 ml) was admixed with 35% eq. formalin solution (8 ml) and potassium carbonate (200 mg). The reaction mixture was stirred at 40° C. for 2 h and then at RT for 2 h, the solvent was removed under reduced pressure and the residue was admixed with water. The aqueous solution was extracted repeatedly with EtOAc, the combined organic phases were dried over sodium sulfate and the solvent was removed under reduced pressure. After column chromatography purification of the residue (silica gel, 1:1 cyclohexane/EtOAc), the desired product was obtained as a white solid (1.71 g, 63% of theory, m.p. 136-139° C.).

$^1$H NMR (DMSO-d$_6$) δ 3.37 (2H, s); 3.61 (2H, dd, J=10.8 and 6.0 Hz); 3.82 (2H, dd, J=10.8 and 5.6 Hz); 4.78 (2H, t, J=5.6 Hz); 7.21 (1H, dd, J=8.1 and 8.1 Hz); 7.32 (1H, d, J=8.16 Hz); 7.45 (1H, dd, J=8.6 and 8.6 Hz); 7.89 (1H, d, J=8.0 Hz)

4. Synthesis of 3,3-bis(hydroxymethyl)thiochroman-4-one and 3-hydroxymethyl-3-methoxymethyl-4-thiochroman-4-one

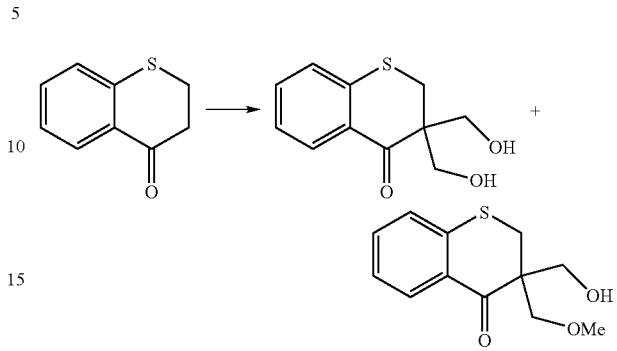

A solution of thiochroman-4-one (10.0 g, 60 mmol) in MeOH (200 ml) and water (40 ml) was admixed with 35% eq. formalin solution (40 ml) and potassium carbonate (1 g). The reaction mixture was stirred at 40° C. for 4 h and then at RT overnight, the solvent was removed under reduced pressure and the residue was admixed with water. The aqueous solution was extracted repeatedly with EtOAc, the combined organic phases were dried over sodium sulfate and the solvent was removed under reduced pressure.

The residue was dissolved in a little EtOAc and admixed with cyclohexane until the crystallization commenced. After filtration and column chromatography purification of the solid (silica gel, 1:1 cyclohexane/EtOAc), 3,3-bis(hydroxymethyl)thiochroman-4-one (3.02 g) was obtained. The filtrate was likewise freed from the solvent and the residue was purified by column chromatography (1:2 to 1:1 EtOAc/cyclohexane). Further 3,3-bis(hydroxymethyl)thiochroman-4-one (2.38 g, overall yield 40% of theory) and 3-hydroxymethyl-3-methoxymethyl-4-thiochroman-4-one (5.21 g, 36% of theory) were obtained.

$^1$H NMR (DMSO-d$_6$) δ 3.22 (3H, s); 3.32 (1H, d, J=13.7 Hz); 3.42 (1H, d, J=13.7 Hz); 3.56 (1H, d; J=9.3 Hz); 3.62 (1H, dd, J=10.9 and 5.7 Hz); 3.74 (1H, d; J=9.3 Hz); 3.79 (1H, dd, J=10.9 and 5.4 Hz); 4.91 (1H, t, J=5.5 Hz); 7.22 (1H, dd, J=7.0 and 7.0 Hz); 7.32 (1H, d, J=7.6 Hz); 7.44 (1H, dd, J=8.6 and 8.6 Hz); 7.90 (1 H, d, J=8.0 Hz)

$^{13}$C NMR (DMSO-d$_6$) δ 30.07; 50.69; 58.82; 60.93; 72.14; 124.75; 127.07; 128.97; 130.12; 133.00; 140.62; 194.07

5. Synthesis of 5-methyl-3,3-bis(hydroxymethyl)thiochroman-4-one

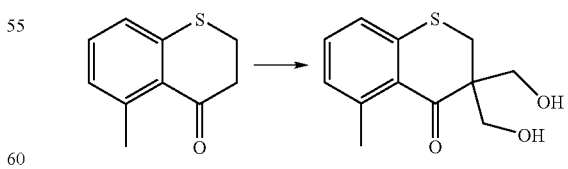

A solution of 5-methylthiochroman-4-one (1.00 g) in MeOH (20 ml) and water (4 ml) was admixed with 35% eq. formalin solution (4 ml) and potassium carbonate (100 mg). The reaction mixture was stirred at 40° C. for 2 h and then at RT for 2 h, the solvent was removed under reduced pressure and the residue was admixed with water. The aqueous solution was extracted repeatedly with EtOAc (3×50 ml), the combined organic phases were dried over sodium sulfate and the solvent was removed under reduced pressure. After column chromatography purification of the residue (silica gel, 1:1 cyclohexane/EtOAc), the desired product was obtained as a white solid (697 mg, 52% of theory, m.p. 138-142° C.).

$^1$H NMR (DMSO-$d_6$) $\delta$ 2.40 (3H, s); 3.29 (2H, s); 3.65 (2H, dd, J=10.8 and 5.4 Hz); 3.78 (2H, dd, J=10.8 and 5.6 Hz); 4.79 (2H, t, J=5.6 Hz); 7.02 (1H, d, J=7.6 Hz); 7.14 (1H, d, J=7.6 Hz); 7.25 (1H, dd, J=7.6 Hz)

6. General Procedure for Reaction of 3,3-bis(hydroxymethyl)thiochroman-4-one Derivatives with Isocyanates or Isothiocyanates of the General Formulae $R^5$—N=C=O, $R^5$—N=C=S, $R^{24}$—N=C=O and $R^{24}$—N=C=S 3,3-Bis(hydroxymethyl)thiochroman-4-one (1 equivalent) was dissolved in THF (1 ml per mmol of 3,3-bis(hydroxymethyl)thiochroman-4-one). Isocyanates or isothiocyanates of the general formulae $R^5$—N=C=O, $R^5$—N=C=S, $R^{24}$—N=C=O or $R^{24}$—N=C=S (2.2 equivalents) and triethylamine (1 equivalent) were added thereto and the reaction mixture was stirred at RT. After 24 hours, the solvent was removed under reduced pressure. The residue was purified by column chromatography (silica gel, cyclohexane/EtOAc or MTBE).

6a. Synthesis of Example Compound 41

3,3-bis(phenylcarbamoyloxymethyl)thiochroman-4-one

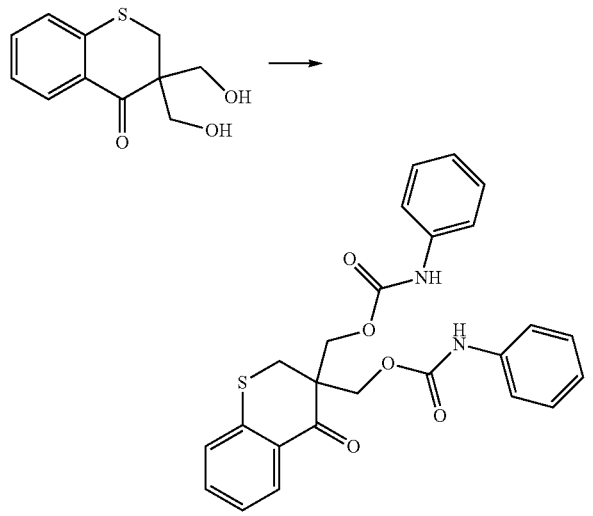

A solution of 3,3-bis(hydroxymethyl)thiochroman-4-one (100 mg, 0.4 mmol) in abs. THF (5 ml) was admixed with phenyl isocyanate (96 µl, 0.88 mmol) and triethylamine (63 µl, 0.4 mmol), and stirred at RT for 24 h. The solvent was removed under reduced pressure. After column chromatography purification of the residue (silica gel, 2:1 cyclohexane/MTBE), the desired product was obtained as a white solid (110 mg, 60% of theory, m.p. 67-69° C.).

$^1$H NMR (DMSO-$d_6$) $\delta$ 3.58 (2H, s); 4.52 (2H, d, J=11.2 Hz); 4.58 (2H, d, J=11.2 Hz); 6.96-7.53 (13H, m); 7.98-8.00 (1H, m); 9.64 (2H, s)

$^{13}$C NMR (DMSO-$d_6$) $\delta$ 30.13; 47.70; 63.17; 117.98; 122.29; 125.11; 127.19; 128.46; 129.24; 129.39; 133.55; 138.49; 140.25; 152.60; 191.97

6b. Synthesis of Example Compound 42

3,3-bis(4-methoxyphenylcarbamoyloxymethyl)thiochroman-4-one

A solution of 3,3-bis(hydroxymethyl)thiochroman-4-one (100 mg, 0.4 mmol) in abs. THF (5 ml) was admixed with 4-methoxyphenyl isocyanate (114 µl, 0.88 mmol) and triethylamine (63 µl, 0.4 mmol), and stirred at RT for 24 h. The solvent was removed under reduced pressure. After column chromatography purification of the residue (silica gel, 1:1 cyclohexane/MTBE), the desired product was obtained as a white solid (75 mg, 36% of theory, m.p. 58-63° C.).

$^1$H NMR (DMSO-$d_6$) $\delta$ 3.56 (2H, s); 3.70 (6H, s); 4.58 (2H, d, J=10.8 Hz); 4.55 (2H, d, J=10.8 Hz); 6.83-7.53 (11H, m); 7.97-8.00 (1H, m); 9.45 (2H, s)

$^{13}$C NMR (DMSO-$d_6$) $\delta$ 30.17; 47.72; 55.06; 63.09; 113.71; 119.54; 125.10; 127.17; 129.26; 129.38; 131.54; 133.52; 140.25; 152.75; 154.53; 192.03

6c. Synthesis of Example Compound 50

3,3-bis(4-tert-butylphenylcarbamoyloxymethyl)thiochroman-4-one

A solution of 3,3-bis(hydroxymethyl)thiochroman-4-one (250 mg, 1.1 mmol) in abs. THF (5 ml) was admixed with 4-tert-butylphenyl isocyanate (409 µl, 2.3 mmol) and triethylamine (152 µl, 1.1 mmol), and stirred at RT for 24 h. The solvent was removed under reduced pressure. After column chromatography purification of the residue (silica gel, 6:1 cyclohexane/EtOAc), the desired product was obtained as a white solid (255 mg, 40% of theory, m.p. 78-85° C.).

$^1$H NMR (DMSO-$d_6$) $\delta$ 1.24 (18H, s); 3.57 (2H, s); 4.50 (2H, d, J=10.8 Hz); 4.57 (2H, d, J=11.2 Hz); 7.26-7.53 (11H, m); 7.98-8.00 (1H, m); 9.45 (2H, s)

$^{13}$C NMR (DMSO-$d_6$) $\delta$ 30.16; 31.16; 33.85; 47.72; 63.12; 117.84; 125.08 (2C); 127.19; 129.26; 129.39; 133.53; 135.87; 140.24; 144.56; 152.66; 192.01

6d. Synthesis of Example Compound 51

3,3-bis(2-tert-butylphenylcarbamoyloxymethyl)thiochroman-4-one

A solution of 3,3-bis(hydroxymethyl)thiochroman-4-one (250 mg, 1.1 mmol) in abs. THF (5 ml) was admixed with 2-tert-butylphenyl isocyanate (409 µl, 2.3 mmol) and triethylamine (152 µl, 1.1 mmol), and stirred at RT for 24 h. The solvent was removed under reduced pressure. After column chromatography purification of the residue (silica gel, 6:1 cyclohexane/EtOAc), the desired product was obtained as a white solid (413 mg, 65% of theory, m.p. 62-68° C.).

$^1$H NMR (DMSO-$d_6$) $\delta$ 1.30 (18H, s); 3.40-3.50 (2H, br s); 4.35-4.55 (4H, br s); 7.03-7.50 (11H, m); 7.98-8.00 (1H, m); 8.64 (2H, s)

$^{13}$C NMR (DMSO-$d_6$) $\delta$ 30.04; 30.72; 34.75; 47.92; 63.17; 124.97; 126.10; 126.26; 126.66; 127.05; 129.28; 129.43; 131.16; 133.33; 135.27; 140.01; 146.25; 154.43; 191.96

6e. Synthesis of Example Compound 52

3,3-bis(4-trifluoromethyl phenylcarbamoyloxymethyl)thiochroman-4-one

A solution of 3,3-bis(hydroxymethyl)thiochroman-4-one (250 mg, 1.1 mmol) in abs. THF (5 ml) was admixed with 4-(trifluoromethyl)phenyl isocyanate (328 µl, 2.3 mmol) and triethylamine (152 µl, 1.1 mmol), and stirred at RT for 24 h. The solvent was removed under reduced pressure. After column chromatography purification of the residue (silica gel, 4:1 cyclohexane/EtOAc), the desired product was obtained as a white solid (567 mg, 86% of theory, m.p. 76-82° C.).

$^1$H NMR (DMSO-$d_6$) δ 3.60 (2H, s); 4.56 (2H, d, J=10.8 Hz); 4.64 (2H, d, J=11.2 Hz); 7.27-7.54 (3H, m); 7.62 (8H, s); 7.98-8.01 (1H, m); 10.08 (2H, s)

$^{13}$C NMR (DMSO-$d_6$) δ 30.11; 47.63; 63.46; 117.76; 122.24; 122.56; 125.16; 125.83; 127.22; 129.16; 129.42; 133.63; 140.27; 142.24; 152.50; 191.90 (the signals for the $CF_3$ group could not be identified.)

6f. Synthesis of Example Compound 53

3,3-bis(2-trifluoromethylphenylcarbamoyloxymethyl)thiochroman-4-one

A solution of 3,3-bis(hydroxymethyl)thiochroman-4-one (250 mg, 1.1 mmol) in abs. THF (5 ml) was admixed with 2-(trifluoromethyl)phenyl isocyanate (348 µl, 2.3 mmol) and triethylamine (152 µl, 1.1 mmol), and stirred at RT for 24 h. The solvent was removed under reduced pressure. After column chromatography purification of the residue (silica gel, 4:1 cyclohexane/EtOAc), the desired product was obtained as a viscous colorless oil (475 mg, 72% of theory).

$^1$H NMR (DMSO-$d_6$) δ 3.49 (2H, s); 4.44 (2H, d, J=10.8 Hz); 4.50 (2H, d, J=10.8 Hz); 7.43-7.71 (11H, m); 7.94-7.96 (1H, m); 9.11 (2H, s)

$^{13}$C NMR (DMSO-$d_6$) δ 29.92; 47.78; 63.48; 123.25 (q, J=274 Hz); 124.62; 125.05; 125.99; 126.04; 126.39; 127.11; 129.31; 129.39; 132.79; 133.45; 134.98; 140.10; 153.91; 191.84

6g. Synthesis of Example Compound 54

3,3-bis(3-trifluoromethylphenylcarbamoyloxymethyl)thiochroman-4-one

A solution of 3,3-bis(hydroxymethyl)thiochroman-4-one (250 mg, 1.1 mmol) in abs. THF (5 ml) was admixed with 3-(trifluoromethyl)phenyl isocyanate (322 µl, 2.3 mmol) and triethylamine (152 µl, 1.1 mmol), and stirred at RT for 24 h. The solvent was removed under reduced pressure. After column chromatography purification of the residue (silica gel, 4:1 cyclohexane/EtOAc), the desired product was obtained as a white solid (268 mg, 41% of theory, m.p. 58-63° C.).

$^1$H NMR (DMSO-$d_6$) δ 3.59 (2H, s); 4.55 (2H, d, J=10.8 Hz); 4.64 (2H, d, J=11.2 Hz); 7.28-7.65 (9H, m); 7.84 (2H, s); 7.98-8.00 (1H, m); 10.03 (2H, s)

$^{13}$C NMR (DMSO-$d_6$) δ 30.11; 47.68; 63.40; 113.94; 118.64; 121.56; 125.15; 127.23; 129.16; 129.40; 129.73; 133.64; 139.39; 140.29; 152.62; 191.92 (the signals for the $CF_3$ group and a further signal for an aromatic carbon atom could not be identified.)

6h. Synthesis of Example Compound 49

Phenylcarbamic acid 3-methoxymethyl-4-oxothiochroman-3-ylmethyl ester

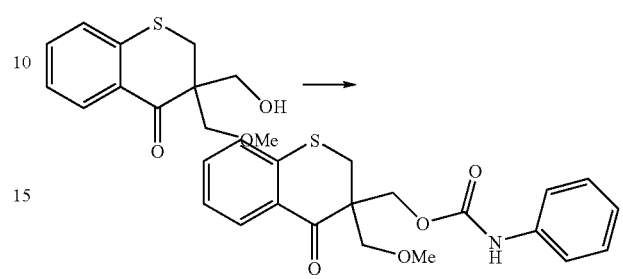

A solution of 3-hydroxymethyl-3-methoxymethyl-4-thiochroman-4-one (500 mg, 2.1 mmol) in abs. THF (10 ml) was admixed with phenyl isocyanate (251 µl, 2.3 mmol) and triethylamine (292 µl, 1.1 mmol), and stirred at RT for 24 h. The solvent was removed under reduced pressure. After column chromatography purification of the residue (silica gel, 9:1 cyclohexane/EtOAc), the desired product was obtained as a viscous oil (660 mg, 88% of theory).

$^1$H NMR (DMSO-$d_6$) δ 3.30 (3H, s); 3.41 (1H, d, J=13.6 Hz); 3.54 (1H, d, J=14.4 Hz); 3.67 (1H, d, J=9.6 Hz); 3.75 (1H, d, J=10.0 Hz); 4.47 (2H, s); 6.98-7.52 (8H, m); 7.95-7.98 (1H, m); 9.57 (1H, s)

$^{13}$C NMR (DMSO-$d_6$) δ 30.18; 48.65; 58.92; 63.80; 71.00; 117.96; 122.23; 124.98; 127.18; 128.46; 129.25; 129.45; 133.38; 138.59; 140.52; 152.75; 192.57

6j. Synthesis of Example Compound 40

(5-methyl-4-oxothiochroman-3,3-diyl)bis(methylene)bis(phenylcarbamate)

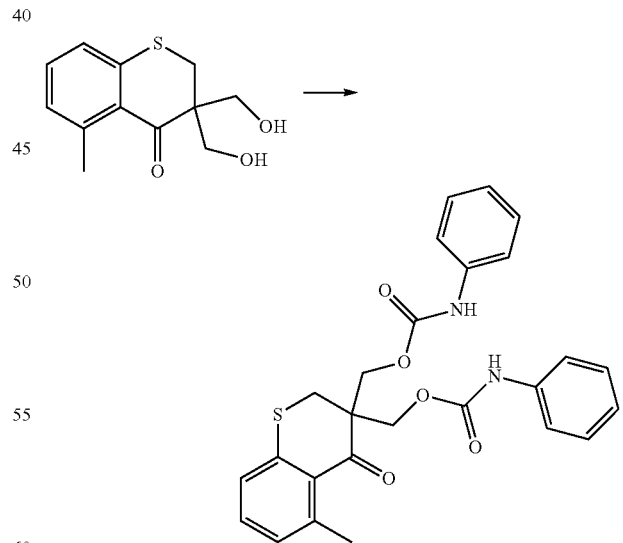

A solution of 3,3-bis(hydroxymethyl)-5-methylthiochroman-4-one (666 mg, 2.8 mmol) in abs. THF (15 ml) was admixed with phenyl isocyanate (667 mg, 5.6 mmol) and triethylamine (0.4 ml), and stirred at RT for 24 h. The solvent was removed under reduced pressure. After column chromatography purification of the residue (silica gel, 2:1 cyclohexane/MTBE), the desired product was obtained as a white solid (1.07 g, 80% of theory, m.p. 55-65° C.).

¹H NMR (DMSO-d$_6$) δ 2.43 (3H, s); 3.55 (2H, s); 4.46 (2H, d, J=11.2 Hz); 4.57 (2H, d, J=11.2 Hz); 6.95-7.50 (13H, m); 9.63 (2H, br s)

¹³C NMR (DMSO-d$_6$) δ 22.60; 29.73; 49.05; 63.72; 118.02; 122.30; 124.85; 128.46; 128.83; 129.04; 131.98; 138.49; 140.30; 141.98; 152.64; 195.58

7. Synthesis of 3,3-bis(hydroxymethyl)-1-oxo-1λ⁴-thiochroman-4-one

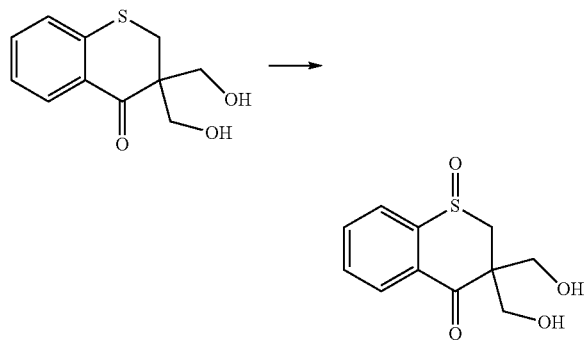

A solution of 3,3-bis(hydroxymethyl)thiochroman-4-one (200 mg, 0.9 mmol) in MeOH (5 ml) was admixed with a solution of sodium metaperiodate (206 mg, 0.96 mmol) in water (2 ml) and stirred at RT for 72 h. The reaction mixture was diluted with water (10 ml) and extracted with EtOAc (3×30 ml), the combined organic phases were dried over sodium sulfate and the solvent was removed under reduced pressure. After column chromatography purification of the residue (silica gel, EtOAc), the desired product was obtained as a white solid (113 mg, 52% of theory, m.p. 108-111° C.).

¹H NMR (DMSO-d$_6$) δ 3.47 (1H, dd, J=4.8 and 10.4 Hz); 3.56 (1H, d, J=12.4 Hz); 3.57 (1H, dd, J=5.6 and 10.8 Hz); 3.71 (1H, dd, J=5.6 and 11.2 Hz); 3.75 (1H, d, J=12.4 Hz); 3.86 (1H, dd, J=5.6 and 10.8 Hz); 5.05 (1H, t, J=5.2 Hz); 5.26 (1H, t, J=5.2 Hz); 7.68-7.84 (1H, m); 7.85-7.86 (2H, m); 7.88-7.96 (1H, m)

8. Synthesis of 3,3-bis(hydroxymethyl)-7-methyl-1-oxo-1λ⁴-thiochroman-4-one

A solution of 3,3-bis(hydroxymethyl)-7-methylthiochroman-4-one (300 mg, 1.26 mmol) in MeOH (6 ml) was admixed with a solution of sodium metaperiodate (286 mg, 1.34 mmol) in water (3 ml) and stirred at RT overnight. The reaction mixture was diluted with water (20 ml) and extracted with EtOAc (3×30 ml), the combined organic phases were dried over sodium sulfate and the solvent was removed under reduced pressure. After column chromatography purification of the residue (silica gel, 4:1 cyclohexane/EtOAc, 1% by vol. of acetic acid), the desired product was obtained as a white solid (186 mg, 58% of theory).

¹H NMR (DMSO-d$_6$) δ 2.47 (3H, s); 3.45 (1H, dd, J=10.4 and 5.0 Hz); 3.52 (1H, d, J=12.6 Hz); 3.53 (1H, dd, J=10.5 and 5.2 Hz); 3.69 (1H, dd, J=10.5 and 4.8 Hz); 3.73 (1H, d, J=12.5 Hz); 3.85 (1H, dd, J=10.4 and 5.9 Hz); 5.02 (1H, t, J=5.5 Hz); 5.24 (1H, t, J=5.1 Hz); 7.50 (1H, d, J=9.0 Hz); 7.66 (1H, s); 7.85 (1H, d, J=8.0 Hz)

9. Synthesis of 3,3-bis(hydroxymethyl)-1,1-dioxo-1λ⁶-thiochroman-4-one

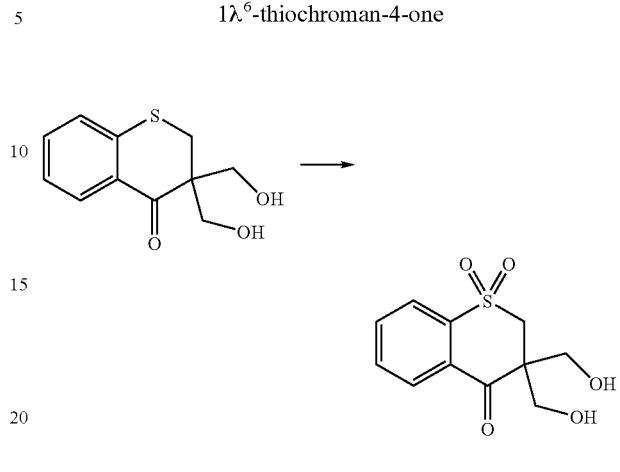

A solution of 3,3-bis(hydroxymethyl)thiochroman-4-one (200 mg, 0.9 mmol) in acetic acid (5 ml) was admixed with 30% aq. hydrogen peroxide solution (250 µl, 2.4 mmol) and stirred at 50° C. overnight. Subsequently, the reaction mixture was neutralized with sat. aq. NaHCO$_3$ solution and extracted with EtOAc (3×20 ml). The combined organic phases were dried over sodium sulfate and the solvent was removed under reduced pressure. After column chromatography purification (1:1 EtOAc/cyclo-hexane), the desired product was obtained as a pale yellow viscous oil (130 mg, 56% of theory).

¹H NMR (DMSO-d$_6$) δ 3.66 (2H, dd, J=5.2 and 10.4 Hz); 3.89 (2H, dd, J=5.6 and 10.4 Hz); 3.93 (2H, s); 5.16 (2H, t, J=5.6 Hz); 7.85-7.99 (4H, m)

10. Synthesis of 3,3-bis(hydroxymethyl)-7-methyl-1,1-dioxo-1λ⁶-thiochroman-4-one A solution of 3,3-bis(hydroxymethyl)-7-methylthiochroman-4-one (300 mg, 1.26 mmol) in acetic acid (6 ml) was admixed with 30% aq. hydrogen peroxide solution (260 µl, 2.52 mmol) and stirred at 50° C. overnight for 6 h, at RT for 72 h and again at 50° C. for 7 h. Subsequently, the reaction mixture was neutralized with sat. aq. NaHCO$_3$ solution and extracted with EtOAc (3×30 ml). The combined organic phases were dried over sodium sulfate and the solvent was removed under reduced pressure. After column chromatography purification (1:1 EtOAc/cyclohexane), the desired product was obtained as white crystals (219 mg, 64% of theory).

11. Synthesis of Example Compound 44

3,3-bis(phenylcarbamoyloxymethyl)-1-oxo-1λ⁴-thiochroman-4-one

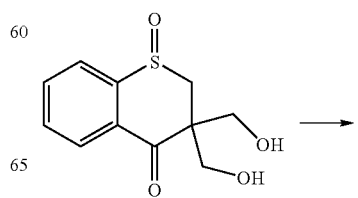

-continued

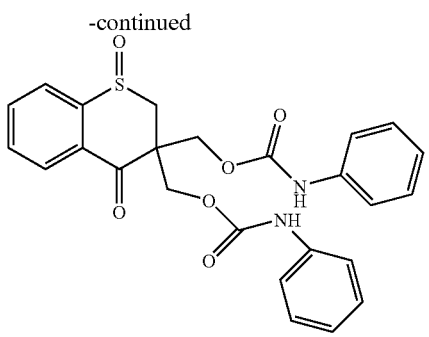

A solution of 3,3-bis(hydroxymethyl)-1-oxo-1λ⁴-thiochroman-4-one (122 mg, 0.5 mmol) in abs. THF (5 ml) was admixed with phenyl isocyanate (120 μl, 1.1 mmol) and triethylamine (70 μl, 0.5 mmol), and stirred at RT for 48 h. The solvent was removed under reduced pressure. After column chromatography purification of the residue (silica gel, 1:1 cyclohexane/EtOAc), the desired product was obtained as a pale yellow solid (85 mg, 27% of theory, m.p. 220-222° C.).

¹H NMR (DMSO-$d_6$) δ 3.72 (1H, d, J=12.8 Hz); 3.96 (1H, d, J=13.2 Hz); 4.42 (1H, d, J=10.8 Hz); 4.53 (1H, d, J=10.8 Hz); 4.60 (1H, d, J=10.8 Hz); 4.65 (1H, d, J=11.6 Hz); 6.94-7.01 (2H, m); 7.24-7.27 (4H, m); 7.38 (4H, br. s); 7.76-7.80 (1H, m); 7.92-7.98 (2H, m); 8.06-8.08 (1H, m); 9.63 (2H, s)

¹³C NMR (DMSO-$d_6$) δ 51.46; 52.64; 65.51; 66.13; 118.88; 123.27; 123.41; 128.25; 129.37; 129.40; 129.62; 132.35; 135.65; 139.32; 147.28; 153.21; 153.31; 193.42

As a result of the stereogenic center on the sulfur of the sulfoxide group, groups become diastereotopic, which results in some degree of signal doubling.

12. Synthesis of Example Compound 43

3,3-bis(phenylcarbamoyloxymethyl)-1,1-dioxo-1λ⁶-thiochroman-4-one

A solution of 3,3-bis(hydroxymethyl)-1,1-dioxo-1λ⁶-thiochroman-4-one (120 mg, 0.47 mmol) in abs. THF (5 ml) was admixed with phenyl isocyanate (109 μl, 1.0 mmol) and triethylamine (65 μl, 0.47 mmol), and stirred at RT for 24 h. The solvent was removed under reduced pressure. After column chromatography purification of the residue (silica gel, 4:1 cyclohexane/EtOAc), the desired product was obtained as a pale yellow solid (51 mg, 22% of theory, m.p. 72-78° C.).

¹H NMR (DMSO-$d_6$) d 4.26 (2H, s); 4.52 (2H, d, J=11.2 Hz); 4.73 (2H, d, J=10.8 Hz); 6.98-7.02 (2H, m); 7.25-7.29 (4H, m); 7.38-7.40 (4H, m); 7.92-8.10 (4H, m); 9.66 (2H, s)

¹³C NMR (DMSO-$d_6$) d 51.59; 51.96; 63.40; 117.97; 122.41; 122.74; 128.52; 128.81; 128.99; 133.69; 135.46; 138.35; 140.71; 152.28; 190.47

13. Synthesis of Example Compound 47

3,3-bis(phenylcarbamoyloxymethyl)-7-methyl-1-oxo-1λ⁴-thiochroman-4-one

A solution of 3,3-bis(hydroxymethyl)-1-oxo-1λ⁴-thiochroman-4-one (174 mg, 0.65 mmol) in abs. THF (8 ml) was admixed with phenyl isocyanate (153 μl, 1.4 mmol) and triethylamine (91 μl, 0.65 mmol), and stirred at RT for 48 h. The solvent was removed under reduced pressure. After column chromatography purification of the residue (silica gel, 1:1 cyclohexane/EtOAc), the desired product was obtained as a pale yellow solid (130 mg, 41% of theory, m.p. 65-73° C.).

¹H NMR (DMSO-$d_6$) δ 1.99 (3H, s); 3.69 (1H, d, J=12.8 Hz); 3.94 (1H, d, J=12.8 Hz); 4.40 (1H, d, J=11.6 Hz); 4.50 (1H, d, J=10.8 Hz); 4.59 (1H, d, J=10.4 Hz); 4.64 (1H, d, J=11.2 Hz); 6.98-7.01 (2H, m); 7.23-7.27 (4H, m); 7.38-7.40 (4H, m); 7.57-7.59 (1H, m); 7.73 (1H, s); 7.96-7.98 (1H, m); 9.62 (2H, s)

¹³C NMR (DMSO-$d_6$) δ 21.24; 50.55; 51.81; 64.69; 65.26; 117.97; 118.20; 122.34; 122.48; 126.20; 127.39; 128.44; 128.85; 132.05; 138.41; 145.88; 146.31; 152.29; 152.40; 192.06

As a result of the stereogenic center on the sulfur of the sulfoxide group, groups become diastereotopic, which results in some degree of signal doubling.

14. Synthesis of Example Compound 48

3,3-bis(phenylcarbamoyloxymethyl)-7-methyl-1,1-dioxo-1λ⁶-thiochroman-4-one

A solution of 3,3-bis(hydroxymethyl)-7-methyl-1,1-dioxo-1λ⁶-thiochroman-4-one (210 mg, 0.78 mmol) in abs. THF (8 ml) was admixed with phenyl isocyanate (176 μl, 1.6 mmol) and triethylamine (103 μl, 0.78 mmol), and stirred at RT for 120 h. The solvent was removed under reduced pressure. After column chromatography purification of the residue (silica gel, 4:1 cyclohexane/EtOAc), the desired product was obtained as a pale yellow solid (222 mg, 56% of theory, m.p. 85-95° C.).

¹H NMR (DMSO-$d_6$) δ 2.53 (3H, s); 4.22 (2H, s); 4.52 (2H, d, J=11.2 Hz); 4.70 (2H, d, J=11.6 Hz); 6.97-7.02 (2H, m); 7.27 (4H, t, J=8.0 Hz); 7.39 (4H, d, J=8.4 Hz); 7.71-7.73 (1H, m); 7.87 (1H, s); 7.98 (1H, d, J=8.4 Hz); 9.66 (2H, s)

¹³C NMR (DMSO-$d_6$) δ 21.21; 51.67; 51.85; 63.49; 117.95; 122.39; 122.60; 126.60; 128.51; 128.91; 134.28; 138.36; 140.66; 146.88; 152.27; 190.15

15. Synthesis of Example Compound 45

3,3-bis(phenylcarbamoyloxymethyl)-5-methyl-1-oxo-1λ⁴-thiochroman-4-one

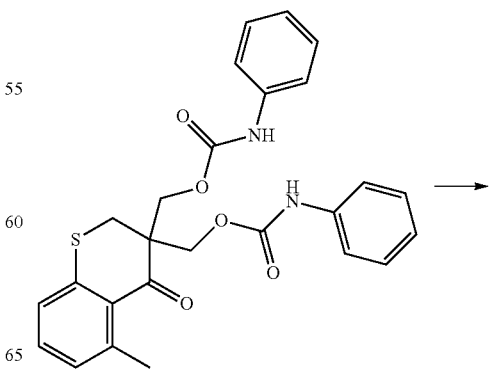

-continued

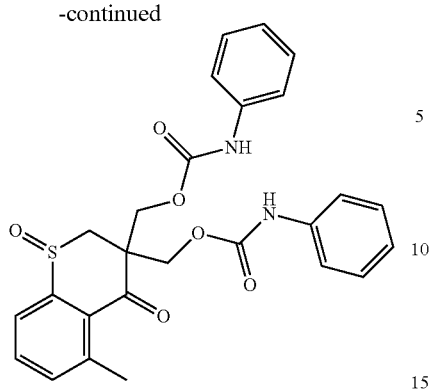

A solution of 3,3-bis(phenylcarbamoyloxymethyl)-5-methylthiochroman-4-one (190 mg, 0.4 mmol) in MeOH (5 ml) was admixed with a solution of sodium metaperiodate (92 mg, 0.43 mmol) in water (1 ml), and stirred at RT for 72 h. The reaction mixture was diluted with water (50 ml) and extracted with EtOAc (3×30 ml), the combined organic phases were dried over sodium sulfate and the solvent was removed under reduced pressure. After column chromatography purification of the residue (silica gel, 1:1 cyclohexane/EtOAc), the desired product was obtained as a white solid (190 mg, 89% of theory, m.p. 76-82° C.).

$^1$H NMR (DMSO-d$_6$) δ 2.43 (3H, s); 4.08 (2H, s); 4.41 (2H, d, J=11.2 Hz); 4.63 (2H, d, J=11.2 Hz); 6.99-7.02 (2H, m); 7.26-7.30 (4H, m); 7.40-7.42 (4H, m); 7.72-7.83 (3H, m); 9.69 (2H, s)

$^{13}$C NMR (DMSO-d$_6$) δ 20.40; 50.27; 52.95; 63.55; 118.06; 120.57; 122.47; 128.52; 130.14; 133.15; 136.86; 138.34; 140.65; 140.81; 152.35; 193.90

16. General Procedure for Reaction of 3,3-bis(hydroxymethyl)thiochroman-4-one Derivatives with Carboxylic Acid Derivatives, Carbonic Acid Derivatives and Sulfonic Acid Derivatives of the General Formulae R$^5$—C(=O)-LG, R$^{24}$—C(=O)-LG, R$^5$—O—C(=O)-LG, R$^{24}$—O—C(=O)-LG, R$^5$—S(=O)$_2$-LG and R$^{24}$—S(=O)$_2$-LG To a solution of the 3,3-bis(hydroxymethyl)thiochroman-4-one derivatives (1 equivalent) in pyridine (4 ml per mmol of 3,3-bis(hydroxymethyl)thiochroman-4-one derivative) was in each case added the carboxylic acid derivative, carbonic acid derivative or sulfonic acid derivative of the general formulae R$^5$—C(=O)-LG, R$^{24}$—C(=O)-LG, R$^5$—O—C(=O)-LG, R$^{24}$—O—C(=O)-LG, R$^5$—S(=O)$_2$-LG and R$^{24}$—S(=O)$_2$-LG (2.1 equivalents) and optionally a catalytic amount of DMAP at 0° C. The reaction solution was warmed to RT and stirred overnight. The reaction mixture was added to an aq. hydrochloric acid solution/ice mixture at 0° C. and extracted repeatedly with diethyl ether. The solvent was removed under reduced pressure and the residue was purified by column chromatography on silica gel with EtOAc/cyclohexane mixtures as the eluent in order to obtain the desired product.

Synthesis of Example Compound 9

(8-methyl-4-oxothiochroman-3,3-diyl)bis(methylene)bis(4-tert-butylbenzenesulfonate)

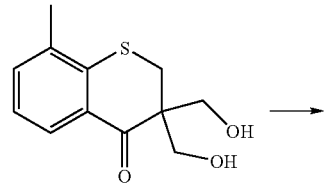

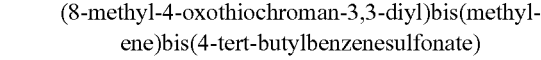

To a solution of 3,3-bis(hydroxymethyl)-8-methylthiochroman-4-one (300 mg, 1.26 mmol) in pyridine (5 ml) was added, at 0° C., 4-tert-butylbenzenesulfonyl chloride (614 mg, 2.64 mmol). The reaction mixture was stirred at RT overnight, added to an aq. hydrochloric acid solution/ice mixture with ice cooling and admixed with diethyl ether. The aqueous phase was extracted repeatedly with diethyl ether (100 ml in total), the combined organic phases were dried over sodium sulfate and the solvent was removed under reduced pressure. The residue was dissolved in a little EtOAc and admixed with hexane for crystal formation. The desired product was obtained as a white solid (190 mg, 35% of theory).

Synthesis of Example Compound 2

(4-oxothiochroman-3,3-diyl)bis(methylene)bis(2-(trifluoromethyl)benzoate)

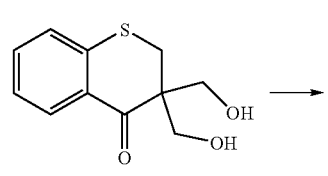

-continued

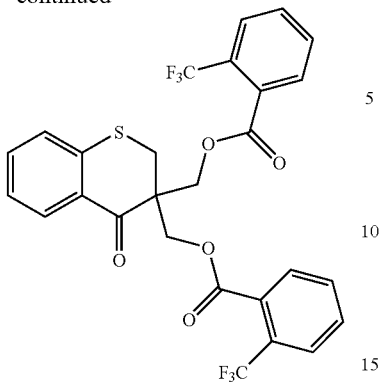

To a solution of 3,3-bis(hydroxymethyl)thiochroman-4-one (300 mg, 1.338 mmol) in pyridine (5.3 ml) was added, at 0° C., 2-(trifluoromethyl)benzoyl chloride (585 mg, 2.81 mmol). The reaction mixture was stirred at RT overnight, added to an aq. hydrochloric acid solution/ice mixture with ice cooling and admixed with diethyl ether. The aqueous phase was extracted repeatedly with diethyl ether (100 ml in total), the combined organic phases were dried over magnesium sulfate and the solvent was removed under reduced pressure. The desired product was obtained as a white solid (692 mg, 91% of theory).

Synthesis of Example Compound 56 bis(3-trifluoromethyl)-(4-oxothiochroman-3,3-diyl)bis(methylene)dicarbonate

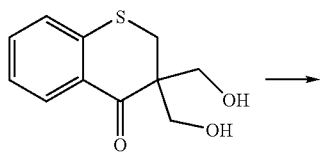 →

-continued

To a solution of 3,3-bis(hydroxymethyl)thiochroman-4-one (300 mg, 1.338 mmol) and 4-dimethylaminopyridine (16 mg, 0.13 mmol) in pyridine (5.3 ml) was added, at 0° C., 3-(trifluoromethyl)phenyl chloroformate (630 mg, 2.81 mmol). The reaction mixture was stirred at RT overnight, adjusted to pH=5 with 10% aq. KHSO$_4$ solution and admixed with diethyl ether. The aqueous phase was extracted repeatedly with diethyl ether (100 ml in total), the combined organic phases were washed with sat. aq. NaHCO$_3$ solution and dried over magnesium sulfate, and the solvent was removed under reduced pressure. The residue was boiled in diethyl ether while heating and the solution was slowly cooled to 4° C. The desired product was obtained as a white solid (315 mg, 39% of theory).

The further example compounds were prepared according to the synthesis procedure described above. The starting compounds required for this purpose are known to those skilled in the art.

| | |
|---|---|
| [1] | (4-oxothiochroman-3,3-diyl)bis(methylene)bis(2-(trifluoromethyl)benzoate) |
| [3] | (6-methoxy-4-oxothiochroman-3,3-diyl)bis(methylene)bis(3-(trifluoromethyl)benzoate) |
| [4] | (8-chloro-4-oxothiochroman-3,3-diyl)bis(methylene)bis(3-(trifluoromethyl)benzoate) |
| [5] | (8-methyl-4-oxothiochroman-3,3-diyl)bis(methylene)bis(3-(trifluoromethyl)benzoate) |
| [6] | (8-methyl-4-oxothiochroman-3,3-diyl)bis(methylene)bis(2-(trifluoromethyl)benzoate) |
| [7] | (6,8-dimethyl-4-oxothiochroman-3,3-diyl)bis(methylene)bis(4-tert-butylbenzenesulfonate) |
| [8] | 4-tert-butylbenzenesulfonic acid 3-hydroxymethyl-4-oxothiochroman-3-ylmethyl ester |
| [10] | (6,8-dimethyl-4-oxothiochroman-3,3-diyl)bis(methylene)bis(3-(trifluoromethyl)benzoate) |
| [11] | (6-fluoro-4-oxothiochroman-3,3-diyl)bis(methylene)bis(3-(trifluoromethyl)benzoate) |
| [12] | (6,8-dimethyl-4-oxothiochroman-3,3-diyl)bis(methylene)bis(2-(trifluoromethyl)benzoate) |
| [13] | 4-tert-butylbenzenesulfonic acid 3-hydroxymethyl-8-methyl-4-oxothiochroman-3-ylmethyl ester |
| [14] | (8-chloro-4-oxothiochroman-3,3-diyl)bis(methylene)bis(2-(trifluoromethyl)phenylcarbamate) |
| [15] | (6-fluoro-4-oxothiochroman-3,3-diyl)bis(methylene)bis(2-(trifluoromethyl)benzoate) |
| [16] | 2-trifluoromethylbenzoic acid 6-fluoro-3-hydroxymethyl-4-oxothiochroman-3-ylmethyl ester |
| [17] | (6-fluoro-4-oxothiochroman-3,3-diyl)bis(methylene)bis(4-tert-butylbenzenesulfonate) |

-continued

| | |
|---|---|
| [18] | 4-tert-butylbenzenesulfonic acid 6-fluoro-3-hydroxymethyl-4-oxothiochroman-3-ylmethyl ester |
| [19] | 4-tert-butylbenzenesulfonic acid 8-chloro-3-hydroxymethyl-4-oxothiochroman-3-ylmethyl ester |
| [20] | (8-chloro-4-oxothiochroman-3,3-diyl)bis(methylene)bis(3-(trifluoromethyl)phenylcarbamate) |
| [21] | 2-trifluoromethylbenzoic acid 8-chloro-3-hydroxymethyl-4-oxothiochroman-3-ylmethyl ester |
| [22] | (5-methyl-4-oxothiochroman-3,3-diyl)bis(methylene)bis(4-tert-butylbenzenesulfonate) |
| [23] | 2-trifluoromethylbenzoic acid 3-hydroxymethyl-6-methoxy-4-oxothiochroman-3-ylmethyl ester |
| [24] | (7,8-dichloro-4-oxothiochroman-3,3-diyl)bis(methylene)bis(4-tert-butylbenzenesulfonate) |
| [25] | (6-methoxy-4-oxothiochroman-3,3-diyl)bis(methylene)bis(4-tert-butylbenzenesulfonate) |
| [26] | (8-chloro-4-oxothiochroman-3,3-diyl)bis(methylene)bis(2-(trifluoromethyl)benzoate) |
| [27] | (5-methyl-4-oxothiochroman-3,3-diyl)bis(methylene)bis(2-(trifluoromethyl)phenylcarbamate) |
| [28] | (5-methyl-4-oxothiochroman-3,3-diyl)bis(methylene)bis(3-(trifluoromethyl)phenylcarbamate) |
| [29] | (7,8-dichloro-4-oxothiochroman-3,3-diyl)bis(methylene)bis(3-(trifluoromethyl)phenylcarbamate) |
| [30] | (6-fluoro-4-oxothiochroman-3,3-diyl)bis(methylene)bis(3-(trifluoromethyl)phenylcarbamate) |
| [31] | (7,8-dichloro-4-oxothiochroman-3,3-diyl)bis(methylene)bis(2-(trifluoromethyl)phenylcarbamate) |
| [32] | 2-trifluoromethylbenzoic acid 3-hydroxymethyl-5-methyl-4-oxothiochroman-3-ylmethyl ester |
| [33] | (5-methyl-4-oxothiochroman-3,3-diyl)bis(methylene)bis(3-(trifluoromethyl)benzoate) |
| [34] | 3-trifluoromethylbenzoic acid 3-hydroxymethyl-5-methyl-4-oxothiochroman-3-ylmethyl ester |
| [35] | (5-methyl-4-oxothiochroman-3,3-diyl)bis(methylene)bis(2-(trifluoromethyl)benzoate) |
| [36] | 3,3-bis(4-tert-butylbenzenesulfonyloxymethyl)-5-methyl-1,1-dioxo-1$\lambda^6$-thiochroman-4-one |
| [37] | 3,3-bis(3-trifluoromethylphenylcarbamoyloxymethyl)-5-methyl-1,1-dioxo-1$\lambda^6$-thiochroman-4-one |
| [38] | bis(4-chlorophenyl)(4-oxothiochroman-3,3-diyl)bis(methylene)dicarbonate |
| [39] | (7-methyl-4-oxothiochroman-3,3-diyl)bis(methylene)bis(phenylcarbamate) |
| [46] | 3,3-bis(phenylcarbamoyloxymethyl)-5-methyl-1,1-dioxo-1$\lambda$-$^6$-thiochroman-4-one |
| [55] | phenylcarbamic acid 4-oxothiochroman-3-ylmethyl ester |

Pharmacological Data

The affinity of the inventive substituted benzofused cyclohexanone derivatives for vanilloid receptor 1 (VR1/TRPV1 receptor) was determined as described below.

| | VR1 (human) (% inhibition compared to 10 µM CP) | VR1 (rat) (% stimulation compared to 10 µM CP) | VR1 (rat) (% inhibition compared to 10 µM CP) | $EC_{50}$ VR1 (rat) [µM] | $EC_{50}$ VR1 (human) [µM] | $IC_{50}$ VR1 (rat) [µM] | $IC_{50}$ VR1 (human) [µM] |
|---|---|---|---|---|---|---|---|
| 13 | 23.80 | 0.81 | 40.33 | | | | |
| 14 | 69.64 | 17.64 | 61.99 | | | | |
| 20 | 88.98 | 47.96 | 107.78 | | | 6.44 | 5.78 |
| 29 | 91.55 | 88.01 | 100.80 | | | | |
| 30 | 80.26 | 94.65 | 44.38 | | | | |
| 31 | 83.36 | 22.05 | 38.68 | | | | |
| 39 | 88.33 | 109.36 | 119.74 | 5.86 | 0.99 | | |
| 40 | 96.61 | 66.98 | 106.17 | 4.1 | 1.4 | | |
| 41 | 94.98 | 38 | 14 | 2.4 | 0.995 | | |
| 42 | 73.22 | 37.77 | 41.12 | 9.95 | 3.05 | | |
| 43 | 9.79 | 48.54 | 83.88 | 25.4 | 9.0 | | |
| 46 | 38.46 | 25.04 | 96.76 | 13.8 | 6.4 | | |
| 47 | 59.17 | 11.79 | 61.54 | 20.3 | 13.4 | | |
| 48 | 81.12 | 64.93 | 88.83 | 3.4 | 1.85 | | |
| 50 | 0 | 0 | 99.87 | | | 5.7 | >20 |

The invention claimed is:
1. A substituted benzofused cyclohexanone derivative of the general formula I

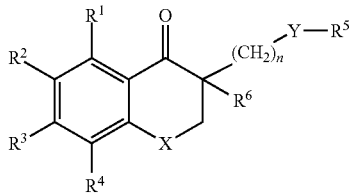

in which
n is 1, 2 or 3;
X is S, S(=O), S(=O)$_2$;
Y is O, O—C(=O), O—C(=O)—O, O—S(=O)$_2$, O—C(=O)—N(H), O—C(=S)—N(H), N(H), N(H)—C(=O)—N(H) or N(H)—C(=S)—N(H); where the free atom which binds to the $R^5$ radical is always stated last;
$R^1$, $R^2$, $R^3$ and $R^4$ are each independently F, Cl, Br, I, —S$_5$, —CN, NC, —SO$_3$H, —NH$_2$, —OH, —SH, —OR$^{10}$, —SR$^{11}$, —NR$^{12}$R$^{13}$, —NH—R$^{14}$, —NH—C(=O)—R$^{15}$, —NR$^{16}$—C(=O)—R$^{17}$, —C(=O)—NH$_2$, —C(=O)—NH—R$^{18}$, —C(=O)—NR$^{19}$R$^{20}$, —C(=)—H, —C(=O)—R$^{21}$, —C(=O)—OH, —C(=O)—OR$^{22}$, —O—C(=O)—R$^{23}$ or a linear or branched, saturated or unsaturated, unsubstituted or at least monosubstituted aliphatic radical;
$R^5$ is a —C(=O)—R$^{26}$ group;
is a —S(=O)$_2$—R$^{27}$ group;
is a linear or branched, saturated or unsaturated, unsubstituted or at least monosubstituted aliphatic radical;
is an unsubstituted or at least monosubstituted, unsaturated or saturated cycloaliphatic radical optionally having at least one heteroatom as a ring member which may be bonded via a linear or branched, unsubstituted or at least monosubstituted alkylene, alkenylene or alkynylene group;
or an unsubstituted or at least monosubstituted aryl or heteroaryl radical which may be bonded via a linear or branched, unsubstituted or at least monosubstituted alkylene, alkenylene or alkynylene group, and/or fused to an unsubstituted or at least monosubstituted mono- or polycyclic ring system;
with the proviso that $R^5$ is not a linear or branched, saturated or unsaturated, unsubstituted or at least monosubstituted aliphatic radical when $R^6$ is —(CH$_2$)$_q$—O—R$^{24}$ in which q=1, 2 or 3 and $R^{24}$ is a linear or branched, saturated or unsaturated, unsubstituted or at least monosubstituted aliphatic radical;
$R^6$ is —(CH$_2$)$_p$—Z—R$^{24}$ where p=1, 2 or 3;
or is —(CH$_2$)$_q$—OR$^{25}$ where q=1, 2 or 3;
$R^{10}$, $R^{11}$, $R^{12}$, $R^{13}$, $R^{11}$, $R^{15}$, $R^{16}$, $R^{17}$, $R^{18}$, $R^{19}$, $R^{20}$, $R^{21}$, $R^{22}$, $R^{23}$, $R^{26}$, $R^{27}$, $R^{28}$ and $R^{29}$ are each independently
a linear or branched, saturated or unsaturated, unsubstituted or at least monosubstituted aliphatic radical;
an unsubstituted or at least monosubstituted, unsaturated or saturated cycloaliphatic radical optionally having at; least one heteroatom as a ring member;
or is an unsubstituted or at least monosubstituted aryl or heteroaryl radical which may be bonded via a linear or branched, unsubstituted or at least monosubstituted alkylene, alkenylene or alkynylene group and/or may be fused to an unsubstituted or at least monosubstituted mono- or polycyclic ring system;
Z is O, O—C(=O), O—C(=O)—O, O—S(=O)$_2$, O—C(=S)—N(H), N(H), N(H)—C(=O)—N(H) or N(H)—C(=S)N(H); where the free atom which binds to the $R^{24}$ radical is always stated last;
$R^{24}$ is a —C(=O)—R$^{28}$ group;
is a —S(=O)$_2$—R$^{29}$ group;
is a linear or branched, saturated or unsaturated, unsubstituted or at least monosubstituted aliphatic; radical;
is an unsubstituted or at least monosubstituted, unsaturated or saturated cycloaliphatic radical optionally having at least one heteroatom as a ring member which may be bonded via a linear or branched, unsubstituted or at least monosubstituted alkylene, alkenylene or alkynylene group;
or is an unsubstituted or at least monosubstituted aryl or heteroaryl radical which may be bonded via a linear or branched, unsubstituted or at least monosubstituted alkylene, alkenylene or alkynylene group and/or may be fused to an unsubstituted or at least monosubstituted mono- or polycyclic ring system; and
$R^{25}$ is a hydrogen radical;
in each case, as appropriate, in the form of one of its pure stereoisomers, especially enantiomers or diastereomers, of its racemates or in the form of a mixture of stereoisomers, especially of the enantiomers and/or diastereomers, in any mixing ratio, or in each case in the form of corresponding salts, or in each case in the form of corresponding solvates;
excluding the compounds
(4-oxothiochroman-3,3-diyl)bis(methylene) bis(4-methoxybenzoate),
(4-oxothiochroman-3,3-diyl)bis(methylene) bis(2,4-dichlorobenzoate),
(4-oxothiochroman-3,3-diyl) bis(methylene)dibenzoate, and
(4-oxothiochroman-3,3-diyl)bis(methylene) bis(3-(trifluoromethyl)benzoate).
2. A compound as claimed in claim 1, characterized in that n is 1, 2 or 3;
X is S, S(=O), S(=O)$_2$;
Y is O, O—C(=O), O—C(=O)—O, O—S(=O)$_2$, O—C(=O)—N(H), O—C(=S)—N(H), N(H), N(H)—C(=O)—N(H) or N(H)—C(=S)—N(H); where the atom which binds to $R^5$ is always stated last;
$R^1$, $R^2$, $R^3$ and $R^4$ are each independently H, F, Cl, Br, I, —SF$_5$, —CN, —NC, —NO$_2$, —SO$_3$H, —NH$_2$, —OH, —SH, —OR$^{10}$, —SR$^{11}$, —NR$^{12}$R$^{13}$, —NH—R$^{14}$, —NH—C(=O)—R$^{15}$, —NR$^{16}$—C(=O)—R$^{17}$, —C(=O)—NH$_2$, —C(=O)—NH—R$^{18}$, —C(=O)—NR$^{19}$R$^{20}$, —C(=O)—H, —C(=O)—R$^{21}$, —C(=O)—OH, —C(=O)—OR$^{22}$, —O—C(=O)—R$^{23}$ or a linear or branched, saturated or unsaturated, optionally substituted C$_{1-10}$ aliphatic radical;
$R^5$ is a —C(=O)—R$^{26}$ group;
is a —S(=O)$_2$—R$^{27}$ group;
is a linear or branched, saturated or unsaturated, optionally substituted C$_{1-10}$ aliphatic radical,
is an unsaturated or saturated, optionally substituted 3-, 4-, 5-, 6-, 7-, 8- or 9-membered cycloaliphatic radical which may be bonded via a —(CH$_2$)—, —(CH$_2$)—(CH$_2$)— or —(CH$_2$)—(CH$_2$)—(CH$_2$)— group;
or is an optionally substituted 5- to 14-membered aryl or heteroaryl radical which may be fused to a saturated or unsaturated, optionally substituted mono- or polycyclic ring system and/or may be bonded via a —(CH$_2$)—, —(CH$_2$)—(CH$_2$)— or —(CH$_2$)—(CH$_2$)—(CH$_2$)— group;

R$^6$ is —(CH$_2$)$_p$—Z—R$^{24}$ where p=1, 2 or 3;
or is —(CH$_2$)$_q$—OR$^{25}$ where q=1, 2 or 3;

R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$, R$^{23}$, R$^{26}$, R$^{27}$, R$^{28}$ and R$^{29}$ are each independently
a linear or branched, saturated or unsaturated, optionally substituted C$_{1-10}$ aliphatic radical;
an unsaturated or saturated, optionally substituted 3-, 4-, 5-, 6-, 7-, 8- or 9-membered cycloaliphatic radical;
or an optionally substituted 5- to 14-membered aryl or heteroaryl radical which may be fused to a saturated or unsaturated, optionally substituted mono- or polycyclic ring system and/or may be bonded via a —(CH$_2$)—, —(CH$_2$)—(CH$_2$)— or —(CH$_2$)—(CH$_2$)—(CH$_2$)— group;

Z is O, O—C(=O), O—C(=O)—O, O—S(=O)$_2$, O—C(=O)—N(H), O—C(=S)—N(H), N(H), N(H)—C(=O)—N(H) or N(H)—C(=S)—N(H); where the free atom which binds to the R$^{24}$ radical is always stated last;

R$^{24}$ is a —C(=O)—R$^{28}$ group;
is a —S(=O)$_2$—R$^{29}$ group;
is an unsaturated or saturated, optionally substituted 3-, 4-, 5-, 6-, 7-, 8- or 9-membered cycloaliphatic radical which may be bonded via a —(CH$_2$)—, —(CH$_2$)—(CH$_2$)— or —(CH$_2$)—(CH$_2$)—(CH$_2$)— group;
is a linear or branched, saturated or unsaturated, optionally substituted C$_{1-10}$ aliphatic radical;
or an optionally substituted 5- to 14-membered aryl or heteroaryl radical, which may be fused to a saturated or unsaturated, optionally substituted mono- or polycyclic ring system and/or may be bonded via a —(CH$_2$)—, —(CH$_2$)—(CH$_2$)— or —(CH$_2$)—(CH$_2$)—(CH$_2$)— group; and R$^{25}$ is a hydrogen radical;

where
the aforementioned C$_{1-10}$ aliphatic radicals may each optionally be substituted by 1, 2, 3, 4, 5, 6, 7, 8 or 9 substituents selected independently from the group consisting of F, Cl, Br, I, —CN, —NO$_2$, —OH, —SH and —NH$_2$;

the aforementioned aryl or heteroaryl radicals may each optionally be substituted by 1, 2, 3, 4 or 5 substituents selected independently from the group consisting of F, Cl, Br, I, —CN, —CF$_3$, —SF$_5$, —OH, —O—C$_{1-5}$-alkyl, —NH$_2$, —NO$_2$, —O—CF$_3$, —S—CF$_3$, —SH, —S—C$_{1-5}$-alkyl, —C$_{1-10}$-alkyl, —C(=O)—OH, —C(=O)—O—C$_{1-5}$-alkyl, —O—C(=O)—C$_{1-5}$-alkyl, —NH—C$_{1-5}$-alkyl, —N(C$_{1-5}$-alkyl)$_2$, —NH—C(=O)—O—C$_{1-5}$-alkyl, —C(=O)—H, —C(=O)—C$_{1-5}$-alkyl, —C(=O)—NH$_2$, —C(=O)—NH—C$_{1-5}$-alkyl, C(=O)—N—(C$_{1-5}$-alkyl)$_2$, —S(=O)$_2$—C$_{1-5}$-alkyl, —S(=O)$_2$-phenyl, —NH—S(=O)$_2$—C$_{1-5}$-alkyl, —S(=O)$_2$—NH—C$_{1-5}$-alkyl, cyclohexyl, cyclopentyl, pyridinyl, pyridazinyl, —(CH$_2$)-benzo[b]furanyl, —O-phenyl, —O-benzyl, phenyl and benzyl, where the cyclic moiety of the pyridinyl, cyclopentyl, cyclohexyl, pyridazinyl, —S(=O)$_2$-phenyl, —O-phenyl, —O-benzyl, phenyl, —(CH$_2$)-benzo[b]furanyl and benzyl radicals may in each case be substituted by 1, 2, 3, 4 or 5 substituents selected independently from the group consisting of F, Cl, Br, —OH, —CF$_3$, —SF$_5$, —CN, —NO$_2$, —C$_{1-5}$-alkyl, —O—C$_{1-5}$-alkyl, —O—CF$_3$, —S—CF$_3$, phenyl and —O-benzyl, and the aforementioned heteroaryl radicals may each optionally have 1, 2, 3, 4 or 5 heteroatom(s) selected independently from the group consisting of oxygen, nitrogen and sulfur as ring member(s);

the rings of the aforementioned mono- or polycyclic ring systems may each be optionally substituted by 1, 2, 3, 4 or 5 substituents selected independently from the group consisting of oxo (=O), thioxo (=S), F, Cl, Br, I, —CN, —CF$_3$, —SF$_5$, —OH, —O—C$_{1-5}$-alkyl, —NH$_2$, —NO$_2$, —O—CF$_3$, —S—CF$_3$, —SH, —S—C$_{1-5}$-alkyl, —C$_{1-5}$-alkyl, —C(=O)—OH, —C(=O)—O—C$_{1-5}$-alkyl, —O—C(=O)—C$_{1-5}$-alkyl, —NH—C$_{1-5}$-alkyl, —N(C$_{1-5}$-alkyl)$_2$, —NH—C(=O)—O—C$_{1-5}$-alkyl, —C(=O)—H, —C(=O)—C$_{1-5}$-alkyl, —C(=O)—NH$_2$, —C(=O)—NH—C$_{1-5}$-alkyl, C(=O)—N—(C$_{1-5}$-alkyl)$_2$, —S(=O)$_2$—C$_{1-5}$-alkyl, —S(=O)$_2$-phenyl, —NH—S(=O)$_2$—C$_{1-5}$-alkyl, —S(=O)$_2$—NH—C$_{1-5}$-alkyl, cyclohexyl, cyclopentyl, pyridinyl, pyridazinyl, —(CH$_2$)-benzo[b]furanyl, —O-phenyl, —O-benzyl, phenyl and benzyl, where the cyclic moiety of the pyridinyl, cyclopentyl, cyclohexyl, pyridazinyl, —S(=O)$_2$-phenyl, —O-phenyl, —O-benzyl, phenyl, —(CH$_2$)-benzo[b]furanyl and benzyl radicals may in each case be substituted by 1, 2, 3, 4 or 5 substituents selected independently from the group consisting of F, Cl, Br, —OH, —CF$_3$, —SF$_5$, —CN, —NO$_2$, —C$_{1-5}$-alkyl, —O—C$_{1-5}$-alkyl, —O—CF$_3$, —S—CF$_3$, phenyl and —O-benzyl, and the aforementioned cycloaliphatic radicals may each optionally have 1, 2, 3, 4 or 5 heteroatom(s) selected independently from the group consisting of oxygen, nitrogen and sulfur as ring member(s), in each case, as appropriate, in the form of one of its pure stereoisomers, especially enantiomers or diastereomers, of its racemates or in the form of a mixture of stereoisomers, especially of the enantiomers and/or diastereomers, in any mixing ratio, or in each case in the form of corresponding salts, or in each case in the form of corresponding solvates.

3. A compound as claimed in claim 1, characterized in that n is 1.

4. A compound as claimed in claim 1, characterized in that Y is O, O—C(=O), O—C(=O)—O, O—S(=O)$_2$, O—C(=S)—N(H) or O—C(=O)—N(H), where the free atom which binds to the R$^5$ radical is always stated last.

5. A compound as claimed in claim 1, characterized in that R$^1$, R$^2$, R$^3$ and R$^4$ are each independently H, F, Cl, Br, I, —SF$_5$, —CN, —NC, —NO$_2$, —SO$_3$H, —NH$_2$, —OH, —SH, —OR$^{10}$, —SR$^{11}$, —NR$^{12}$R$^{13}$, —NH—R$^{14}$, —NH—C(=O)—R$^{15}$, —C(=O)—OH, —C(=O)—OR$^{22}$, —O—C(=O)—R$^{23}$ or a radical selected form the group consisting of methyl, ethyl, n-propyl, isopropyl, n-butyl, sec-butyl, isobutyl, tert-butyl, 1,1-dimethylpropyl, n-pentyl, sec-pentyl, n-hexyl and n-heptyl; where the radical may in each case optionally be substituted by 1, 2, 3, 4 or 5 substituents selected independently from the group consisting of F, Cl, Br, I, —CN, —NO$_2$, —OH, —SH and —NH$_2$.

6. A compound as claimed in claim 1, characterized in that R$^5$ is a —C(=O)—R$^{26}$ group;

is a —S(=O)$_2$—R$^{27}$ group;

is a radical selected from the group consisting of methyl, ethyl, n-propyl, isopropyl, n-butyl, sec-butyl, isobutyl, tert-butyl, 1,1-dimethylpropyl, n-pentyl, sec-pentyl, n-hexyl and n-heptyl; where the radical may optionally be substituted by 1, 2, 3, 4 or 5 substituents selected independently from the group consisting of F, Cl, Br, I, —CN, —NO$_2$, —OH, —SH and —NH$_2$;

is a radical selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl and thiomorpholinyl;

where the radical may be bonded via a —(CH$_2$)—, —(CH$_2$)—(CH$_2$)— or —(CH$_2$)—(CH$_2$)—(CH$_2$)— group and may in each case optionally be substituted by 1, 2, 3, 4 or 5 substituents selected independently from the group consisting of oxo (=O), thioxo (=S), F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl, tert-butyl, —C(=O)—OH, —C(=O)—O—CH$_3$, —C(=O)—O—C$_2$H$_5$, —C(=O)—O—C(CH$_3$)$_3$, —O—C(=O)—CH$_3$, —O—C(=O)—C$_2$H$_5$, —O—C(=O)—C(CH$_3$)$_3$, —N(CH$_3$)$_2$, —N(C$_2$H$_5$)$_2$, —NH—CH$_3$, —NH—C$_2$H$_5$, —NH—C(=O)—O—CH$_3$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—C(CH$_3$)$_3$, —C(=O)—NH$_2$, —C(=O)—NH—CH$_3$, —C(=O)—NH—C$_2$H$_5$, —C(=O)—N—(CH$_3$)$_2$, —C(=O)—N—(C$_2$H$_5$)$_2$, —S(=O)$_2$—CH$_3$ and —S(=O)$_2$—C$_2$H$_5$;

or is a radical selected from the group consisting of phenyl, naphthyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinolinyl, isoquinolinyl, benzimidazolinyl, benzoxazolyl, benzisoxazolyl and benzothiazolyl, where the radical may be bonded via a —(CH$_2$)—, —(CH$_2$)—(CH$_2$)— or —(CH$_2$)—(CH$_2$)—(CH$_2$)— group and may in each case optionally be substituted by 1, 2, 3, 4 or 5 substituents selected independently from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl, tert-butyl, —C(=O)—OH, —C(=O)—O—CH$_3$, —C(=O)—O—C$_2$H$_5$, —C(=O)—O—C(CH$_3$)$_3$, —O—C(=O)—CH$_3$, —O—C(=O)—C$_2$H$_5$, —O—C(=O)—C(CH$_3$)$_3$, —N(CH$_3$)$_2$, —N(C$_2$H$_5$)$_2$, —NH—CH$_3$, —NH—C$_2$H$_5$, —NH—C(=O)—O—CH$_3$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—C(CH$_3$)$_3$, —C(=O)—NH$_2$, —C(=O)—NH—CH$_3$, —C(=O)—NH—C$_2$H$_5$, —C(=O)—N—(CH$_3$)$_2$, —C(=O)—N—(C$_2$H$_5$)$_2$, —S(=O)$_2$—CH$_3$, —S(=O)$_2$—C$_2$H$_5$, —S(=O)$_2$-phenyl, —NH—S(=O)$_2$—CH$_3$, —NH—S(=O)$_2$—C$_2$H$_5$, —S(=O)$_2$—NH—CH$_3$, —S(=O)$_2$—NH—C$_2$H$_5$, cyclohexyl, cyclopentyl, pyridinyl, pyridazinyl, —(CH$_2$)-benzo[b]furanyl, —O-phenyl, —O-benzyl, phenyl and benzyl where the cyclic moiety of the pyridinyl, cyclopentyl, cyclohexyl, pyridazinyl, —S(=O)2-phenyl, —O-phenyl, —O-benzyl, phenyl, —(CH$_2$)-benzo[b]furanyl and benzyl radicals may in each case optionally be substituted by 1, 2, 3, 4 or 5 substituents independently from the group consisting of F, Cl, Br, —OH, —CF$_3$, —SF$_5$, —CN, —NO$_2$, methyl, ethyl, n-propyl, isopropyl, n-butyl, sec-butyl, isobutyl, tert-butyl, —O—CH$_3$, —O—C$_2$H$_5$, —O—CF$_3$, —S—CF$_3$, phenyl and —O-benzyl.

7. A compound as claimed in claim 1, characterized in that R$^6$ is —(CH$_2$)$_p$Z—R$^{24}$ or is —(CH$_2$)—OR$^{25}$.

8. A compound as claimed in claim 1, characterized in that R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$, R$^{23}$, R$^{26}$, R$^{27}$, R$^{28}$ and R$^{29}$ are each independently a radical selected from the group consisting of methyl, ethyl, n-propyl, isopropyl, n-butyl, sec-butyl, isobutyl, tert-butyl, 1,1-dimethylpropyl, n-pentyl, sec-pentyl, n-hexyl and n-heptyl; where the radical may in each case optionally be substituted by 1, 2, 3, 4 or 5 substituents selected independently from the group consisting of F, Cl, Br, I, —CN, —NO$_2$, —OH, —SH and —NH$_2$;

a radical selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl and thiomorpholinyl;

or a radical selected from the group consisting of phenyl, naphthyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinolinyl, isoquinolinyl, benzimidazolinyl, benzoxazolyl, benzisoxazolyl and benzothiazolyl, where the radical may be bonded via a —(CH$_2$)—, —(CH$_2$)—(CH$_2$)— or —(CH$_2$)—(CH$_2$)—(CH$_2$)— group and may in each case optionally be substituted by 1, 2, 3, 4 or 5 substituents selected independently from the group consisting of F, Cl, Br, I, —CN, —CF$_3$, —SF$_5$, —OH, —O—CH$_3$, —O—$C_2H_5$, —$NH_2$, —$NO_2$, —O—$CF_3$, —S—$CF_3$, —SH, —S—$CH_3$, —S—$C_2H_5$, methyl, ethyl, n-propyl, isopropyl, n-butyl, sec-butyl, isobutyl, tert-butyl, —C(=O)—OH, —C(=O)—O—$CH_3$, —C(=O)—O—$C_2H_5$, —C(=O)—O—C($CH_3$)$_3$, —O—C(=O)—$CH_3$, —O—C(=O)—$C_2H_5$, —O—C(=O)—C($CH_3$)$_3$, —N($CH_3$)$_2$, —N($C_2H_5$)$_2$, —NH—$CH_3$, —NH—$C_2H_5$, —NH—C(=O)—O—$CH_3$, —NH—C(=O)—O—$C_2H_5$, —NH—C(=O)—O—C($CH_3$)$_3$, —C(=O)—H, —C(=O)—$CH_3$, —C(=O)—$C_2H_5$, —C(=O)—C($CH_3$)$_3$, —C(=O)—$NH_2$, —C(=O)—NH—$CH_3$, —C(=O)—NH—$C_2H_5$, —C(=O)—N—($CH_3$)$_2$, —C(=O)—N—($C_2H_5$)$_2$.

9. A compound as claimed in claim 1, characterized in that $R^{24}$ is a —C(=O)—$R^{28}$ group;

is a —S(=O)$_2$—$R^{29}$ group;

is a radical selected from the group consisting of methyl, ethyl, n-propyl, isopropyl, n-butyl, sec-butyl, isobutyl, tert-butyl, 1,1-dimethylpropyl, n-pentyl, sec-pentyl, n-hexyl and n-heptyl; where the radical may in each case optionally be substituted by 1, 2, 3, 4 or 5 substituents selected independently from the group consisting of F, Cl, Br, I, —CN, —$NO_2$, —OH, —SH and —$NH_2$;

is a radical selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl and thiomorpholinyl; where the radical may be bonded via a —($CH_2$)—, —($CH_2$)—($CH_2$)— or —($CH_2$)—($CH_2$)—($CH_2$)— group and may in each case optionally be substituted by 1, 2, 3, 4 or 5 substituents selected independently from the group consisting of oxo (=O), thioxo (=S), F, Cl, Br, I, —CN, —$CF_3$, —$SF_5$, —OH, —O—$CH_3$, —O—$C_2H_5$, —$NH_2$, —$NO_2$, —O—$CF_3$, —S—$CF_3$, —SH, —S—$CH_3$, —S—$C_2H_5$, methyl, ethyl, n-propyl, isopropyl, n-butyl, sec-butyl, isobutyl, tert-butyl, —C(=O)—OH, —C(=O)—O—$CH_3$, —C(=O)—O—$C_2H_5$, —C(=O)—O—C($CH_3$)$_3$, —O—C(=O)—$CH_3$, —O—C(=O)—$C_2H_5$, —O—C(=O)—C($CH_3$)$_3$, —N($CH_3$)$_2$, —N($C_2H_5$)$_2$, —NH—$CH_3$, —NH—$C_2H_5$, —NH—C(=O)—O—$CH_3$, —NH—C(=O)—O—$C_2H_5$, —NH—C(=O)—O—C($CH_3$)$_3$, —C(=O)—H, —C(=O)—$CH_3$, —C(=O)—$C_2H_5$, —C(=O)—C($CH_3$)$_3$, —C(=O)—$NH_2$, —C(=O)—NH—$CH_3$, —C(=O)—NH—$C_2H_5$, —C(=O)—N—($CH_3$)$_2$, —C(=O)—N—($C_2H_5$)$_2$, —S(=O)$_2$—$CH_3$ and —S(=O)$_2$—$C_2H_5$;

or a radical selected from the group consisting of phenyl, naphthyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinolinyl, isoquinolinyl, benzimidazolinyl, benzoxazolyl, benzisoxazolyl and benzothiazolyl, where the radical may be bonded via a —($CH_2$)—, —($CH_2$)—($CH_2$)— or —($CH_2$)—($CH_2$)—($CH_2$)— group and may in each case optionally be substituted by 1, 2, 3, 4 or 5 substituents selected independently from the group consisting of F, Cl, Br, I, —CN, —$CF_3$, —$SF_5$, —OH, —O—$CH_3$, —O—$C_2H_5$, —$NH_2$, —$NO_2$, —O—$CF_3$, —S—$CF_3$, —SH, —S—$CH_3$, —S—$C_2H_5$, methyl, ethyl, n-propyl, isopropyl, n-butyl, sec-butyl, isobutyl, tert-butyl, —C(=O)—OH, —C(=O)—O—$CH_3$, —C(=O)—O—$C_2H_5$, —C(=O)—O—C($CH_3$)$_3$, —O—C(=O)—$CH_3$, —O—C(=O)—$C_2H_5$, —O—C(=O)—C($CH_3$)$_3$, —N($CH_3$)$_2$, —N($C_2H_5$)$_2$, —NH—$CH_3$, —NH—$C_2H_5$, —NH—C(=O)—O—$CH_3$, —NH—C(=O)—O—$C_2H_5$, —NH—C(=O)—O—C($CH_3$)$_3$, —C(=O)—H, —C(=O)—$CH_3$, —C(=O)—$C_2H_5$, —C(=O)—C($CH_3$)$_3$, —C(=O)—$NH_2$, —C(=O)—NH—$CH_3$, —C(=O)—NH—$C_2H_5$, —C(=O)—N—($CH_3$)$_2$, —C(=O)—N—($C_2H_5$)$_2$, —S(=O)$_2$—$CH_3$, —S(=O)$_2$—$C_2H_5$, —S(=O)$_2$-phenyl, —NH—S(=O)$_2$—$CH_3$, —NH—S(=O)$_2$—$C_2H_5$, —S(=O)$_2$—NH—$CH_3$, —S(=O)$_2$—NH—$C_2H_5$, cyclohexyl, cyclopentyl, pyridinyl, pyridazinyl, —($CH_2$)-benzo[b]furanyl, —O-phenyl, —O-benzyl, phenyl and benzyl; where the cyclic moiety of the pyridinyl, cyclopentyl, cyclohexyl, pyridazinyl, —S(=O)2-phenyl, —O-phenyl, —O-benzyl, phenyl, —($CH_2$)-benzo[b]furanyl and benzyl radicals may in each case be substituted by 1, 2, 3, 4 or 5 substituents selected independently from the group consisting of F, Cl, Br, —OH, —$CF_3$, —$SF_5$, —CN, —$NO_2$, methyl, ethyl, n-propyl, isopropyl, n-butyl, sec-butyl, isobutyl, tert-butyl, —O—$CH_3$, —O—$C_2H_5$, —O—$CF_3$, —S—$CF_3$, phenyl and —O-benzyl.

10. A compound as claimed in claim 1, characterized in that $R^{25}$ is a hydrogen radical.

11. A compound as claimed in claim 1, characterized in that n is 1;

X is S, S(=O), S(=O)$_2$, N(H), N($R^7$), N[C(=O)—$R^8$] or N[C(=O)—O—$R^9$];

Y is O, O—C(=O), O—C(=O)—O, O—S(=O)$_2$, O—C(=S)—N(H) or O—C(=O)—N(H), where the free atom which binds to the $R^5$ radical is always stated last;

$R^1$, $R^2$, $R^3$ and $R^4$ are each independently

H, F, Cl, Br, I, —$SF_5$, —CN, —NC, —$NO_2$, —OH, —SH, —$OR^{10}$, —$SR^{11}$, or a radical selected from the group consisting of methyl, —$CF_3$, —$CHF_2$, —$CH_2F$, —$CCl_3$, —$CBr_3$, —$CH_2$—CN, —$CH_2$—$NO_2$, ethyl, —$CF_2$—$CF_3$, —$CH_2$—$CF_3$, —$CCl_2$—$CCl_3$, —$CF_2$—$CH_3$, —$CH_2$—$CH_2$—CN, —$CH_2$—$CH_2$—$NO_2$, n-propyl, —$CF_2$—$CF_2$—$CF_3$, —$CH_2$—$CH_2$—$CH_2$—CN, —$CH_2$—$CH_2$—$CH_2$—$NO_2$, isopropyl, n-butyl, sec-butyl, isobutyl, tert-butyl, 1,1-dimethylpropyl, n-pentyl, sec-pentyl, n-hexyl and n-heptyl;

$R^5$ is a —C(=O)—$R^{26}$ group;

is a —S(=O)$_2$—$R^{27}$ group;

is a radical selected from the group consisting of methyl, ethyl, n-propyl, isopropyl, n-butyl, sec-butyl, isobutyl, tert-butyl, 1,1-dimethylpropyl, n-pentyl, sec-pentyl, n-hexyl and n-heptyl;

is a radical selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl and thiomorpholinyl;

or is a radical selected from the group consisting of phenyl, benzyl, phenethyl, naphthyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinolinyl, isoquinolinyl, benzimidazolinyl, benzoxazolyl, benzisoxazolyl and benzothiazolyl, where the radical may in each case optionally be substituted by 1, 2, 3, 4 or 5 substituents selected independently from the group consisting of —$SF_5$, F, Cl, Br, I, —CN, —$CF_3$, —$SF_5$, —OH, —O—$CH_3$, —O—$C_2H_5$, —$NH_2$, —$NO_2$, —O—$CF_3$, —S—$CF_3$, —SH, —S—$CH_3$, —S—$C_2H_5$, methyl, ethyl, n-propyl, isopropyl, n-butyl, sec-butyl, isobutyl, tert-butyl, —C(=O)—OH, —C(=O)—O—$CH_3$, —C(=O)—O—$C_2H_5$, —C(=O)—O—C($CH_3$)$_3$, —O—C(=O)—$CH_3$, —O—C(=O)—$C_2H_5$, —O—C(=O)—C($CH_3$)$_3$, —N($CH_3$)$_2$, —N($C_2H_5$)$_2$, —NH—$CH_3$, —NH—$C_2H_5$, —NH—C(=O)—O—$CH_3$, —NH—C(=O)—O—$C_2H_5$, —NH—C(=O)—O—C($CH_3$)$_3$, —C(=O)—H, —C(=O)—$CH_3$, —C(=O)—$C_2H_5$, —C(=O)—C($CH_3$)$_3$, —C(=O)—$NH_2$, —C(=O)—NH—$CH_3$, —C(=O)—NH—$C_2H_5$, —C(=O)—N—($CH_3$)$_2$, —C(=O)—N—($C_2H_5$)$_2$, —S(=O)$_2$—$CH_3$, —S(=O)$_2$—$C_2H_5$, —NH—S(=O)$_2$—$CH_3$, —NH—S(=O)$_2$—$C_2H_5$, —S(=O)$_2$—NH—$CH_3$ and —S(=O)$_2$—NH—$C_2H_5$;

$R^6$ is —(CH$_2$)—Z—$R^{24}$;
or is —(CH$_2$)—O$R^{25}$;

$R^{10}$ and $R^{11}$ are each independently
a radical selected from the group consisting of methyl, ethyl, n-propyl, isopropyl, n-butyl, sec-butyl, isobutyl, tert-butyl, 1,1-dimethylpropyl, n-pentyl, sec-pentyl, n-hexyl and n-heptyl;
or a radical selected from the group consisting of phenyl, benzyl and phenethyl, where the radical may in each case optionally be substituted by 1, 2, 3, 4 or 5 substituents selected independently from the group consisting of F, Cl, Br, I, —CN, —$CF_3$, —$SF_5$, —OH, —O—$CH_3$, —O—$C_2H_5$, —$NH_2$, —$NO_2$, —O—$CF_3$, —S—$CF_3$, —SH, —S—$CH_3$, —S—$C_2H_5$, methyl, ethyl, n-propyl, isopropyl, n-butyl, sec-butyl, isobutyl and tert-butyl;

Z is O, O—C(=O), O—C(=O)—O, O—S(=O)$_2$, O—C(=S)—N(H) or O—C(=O)—N(H) where the free atom which binds to the $R^{24}$ radical is always stated last;

$R^{24}$ is a —C(=O)—$R^{28}$ group;
is a —S(=O)$_2$—$R^{29}$ group;
is a radical selected from the group consisting of methyl, ethyl, n-propyl, isopropyl, n-butyl, sec-butyl, isobutyl, tert-butyl, 1,1-dimethylpropyl, n-pentyl, sec-pentyl, n-hexyl and n-heptyl;
is a radical selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl and thiomorpholinyl;
or is a radical selected from the group consisting of phenyl, benzyl, phenethyl, naphthyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinolinyl, isoquinolinyl, benzimidazolinyl, benzoxazolyl, benzisoxazolyl and benzothiazolyl, where the radical may in each case optionally be substituted by 1, 2, 3, 4 or 5 substituents selected independently from the group consisting of —$SF_5$, F, Cl, Br, I, —CN, —$CF_3$, —$SF_5$, —OH, —O—$CH_3$, —O—$C_2H_5$, —$NH_2$, —$NO_2$, —O—$CF_3$, —S—$CF_3$, —SH, —S—$CH_3$, —S—$C_2H_5$, methyl, ethyl, n-propyl, isopropyl, n-butyl, sec-butyl, isobutyl, tert-butyl, —C(=O)—OH, —C(=O)—O—$CH_3$, —C(=O)—O—$C_2H_5$, —C(=O)—O—C($CH_3$)$_3$, —O—C(=O)—$CH_3$, —O—C(=O)—$C_2H_5$, —O—C(=O)—C($CH_3$)$_3$, —N($CH_3$)$_2$, —N($C_2H_5$)$_2$, —NH—$CH_3$, —NH—$C_2H_5$, —NH—C(=O)—O—$CH_3$, —NH—C(=O)—O—$C_2H_5$, —NH—C(=O)—O—C($CH_3$)$_3$, —C(=O)—H, —C(=O)—$CH_3$, —C(=O)—$C_2H_5$, —C(=O)—C($CH_3$)$_3$, —C(=O)—$NH_2$, —C(=O)—NH—$CH_3$, —C(=O)—NH—$C_2H_5$, —C(=O)—N—($CH_3$)$_2$, —C(=O)—N—($C_2H_5$)$_2$, —S(=O)$_2$—$CH_3$, —S(=O)$_2$—$C_2H_5$, —NH—S(=O)$_2$—$CH_3$, —NH—S(=O)$_2$—$C_2H_5$, —S(=O)$_2$—NH—$CH_3$ and —S(=O)$_2$—NH—$C_2H_5$;

$R^{25}$ is a hydrogen radical; and $R^{26}$, $R^{27}$, $R^{28}$ and $R^{29}$ are each independently
a radical selected from the group consisting of phenyl, naphthyl, thiophenyl, furanyl and pyridinyl, where the radical may in each case optionally be substituted by 1, 2, 3, 4 or 5 substituents selected independently from the group consisting of F, Cl, Br, I, —CN, —$CF_3$, —$SF_5$, —OH, —O—$CH_3$, —O—$C_2H_5$, —$NH_2$, —$NO_2$, —O—$CF_3$, —S—$CF_3$, —SH, —S—$CH_3$, —S—$C_2H_5$, methyl, ethyl, n-propyl, isopropyl, n-butyl, sec-butyl, isobutyl, tert-butyl, —N($CH_3$)$_2$, —N($C_2H_5$)$_2$, —NH—$CH_3$ and —NH—$C_2H_5$;

in each case, as appropriate, in the form of one of its pure stereoisomers, especially enantiomers or diastereomers, of its racemates or in the form of a mixture of stereoisomers, especially of the enantiomers and/or diastereomers, in any mixing ratio, or in each case in the form of corresponding salts, or in each case in the form of corresponding solvates.

12. A compound as claimed in claim 1, characterized in that
n is 1;
X is S, S(=O) or S(=O)$_2$;
Y is O, O—C(=O), O—C(=O)—O, O—S(=O)$_2$, O—C(=S)—N(H) or O—C(=O)—N(H) where the free atom which binds to the $R^5$ radical is always stated last;
$R^1$, $R^2$, $R^3$ and $R^4$, are each independently
H, F, Cl, Br, —$SF_5$, —OH, —O$R^{10}$,
or a radical selected from the group consisting of methyl, —$CF_3$, —$CHF_2$, —$CH_2F$, —$CCl_3$, —$CBr_3$, —$CH_2$—CN, —$CH_2$—$NO_2$, ethyl, —$CF_2$—$CF_3$, —$CH_2$—$CF_3$, n-propyl, isopropyl, n-butyl, sec-butyl, isobutyl, tert-butyl, 1,1-dimethylpropyl and n-pentyl;

$R^5$ is a —C(=O)—$R^{26}$ group;
is a —S(=O)$_2$—$R^{27}$ group;
is a radical selected from the group consisting of methyl, ethyl, n-propyl, isopropyl, n-butyl, sec-butyl, isobutyl, tert-butyl, 1,1-dimethylpropyl, n-pentyl, sec-pentyl, n-hexyl and n-heptyl;
is a radical selected from the group consisting of cyclopropyl, cyclobutyl, cyclopentyl, cyclohexyl, cycloheptyl, cyclopentenyl, cyclohexenyl and cycloheptenyl;
or is a radical selected from the group consisting of phenyl, naphthyl, thiophenyl, furanyl, pyridinyl, indolyl, thiazolyl and oxazolyl, where the radical may in each case optionally be substituted by 1, 2, 3, 4 or 5 substituents selected independently from the group consisting of F, Cl, Br, —$CF_3$, —O—$CH_3$, —O—C$_2$H$_5$, —O—CF$_3$, —S—CF$_3$, methyl, ethyl, n-propyl, isopropyl, n-butyl, sec-butyl, isobutyl and tert-butyl;

R$^6$ is —(CH$_2$)—Z—R$^{24}$;
or is —(CH$_2$)—OR$^{25}$;

R$^{10}$ is a radical selected from the group consisting of methyl, ethyl, n-propyl, isopropyl, n-butyl, sec-butyl, isobutyl, tert-butyl, 1,1-dimethylpropyl, n-pentyl, sec-pentyl, n-hexyl and n-heptyl;

Z is O, O—C(=O), O—C(=O)—O, O—S(=O)$_2$, O—C(=S)—N(H) or O—C(=O)—N(H), where the free atom which binds to the R$^{24}$ radical is always stated last;

R$^{24}$ is a —C(=O)—R$^{28}$ group;
is a —S(=O)$_2$—R$^{29}$ group;
is a radical selected from the group consisting of methyl, ethyl, n-propyl, isopropyl, n-butyl, sec-butyl, isobutyl, tert-butyl, 1,1-dimethylpropyl, n-pentyl, sec-pentyl, n-hexyl and n-heptyl;
is a radical selected from the group consisting of cyclopropyl, cyclobutyl, cyclopentyl, cyclohexyl, cycloheptyl, cyclopentenyl, cyclohexenyl and cycloheptenyl;
or is a radical selected from the group consisting of phenyl, naphthyl, thiophenyl, furanyl, pyridinyl, indolyl, thiazolyl and oxazolyl, where the radical may in each case optionally be substituted by 1, 2, 3, 4 or 5 substituents selected independently from the group consisting of F, Cl, Br, —CF$_3$, —O—CH$_3$, —O—C$_2$H$_5$, —O—CF$_3$, —S—CF$_3$, methyl, ethyl, n-propyl, isopropyl, n-butyl, sec-butyl, isobutyl and tert-butyl;

R$^{25}$ is a hydrogen radical; and

R$^{26}$, R$^{27}$, R$^{28}$ and R$^{29}$ are each independently
a radical selected from the group consisting of phenyl, naphthyl, thiophenyl, furanyl and pyridinyl, where the radical may in each case optionally be substituted by 1, 2, 3, 4 or 5 substituents selected independently from the group consisting of F, Cl, Br, I, —CF$_3$, —SF$_5$, —O—CH$_3$, —O—C$_2$H$_5$, —S—CF$_3$, methyl, ethyl, n-propyl, isopropyl, n-butyl, sec-butyl, isobutyl and tert-butyl;

in each case, as appropriate, in the form of one of its pure stereoisomers, especially enantiomers or diastereomers, of its racemates or in the form of a mixture of stereoisomers, especially of the enantiomers and/or diastereomers, in any mixing ratio, or in each case in the form of corresponding salts, or in each case in the form of corresponding solvates.

13. A compound as claimed in claim 1 selected from the group consisting of
[2] (4-oxothiochroman-3,3-diyl)bis(methylene)bis(2-(trifluoromethyl)-benzoate)
[3] (6-methoxy-4-oxothiochroman-3,3-diyl)bis(methylene)bis(3-(trifluoromethyl)benzoate)
[4] (8-chloro-4-oxothiochroman-3,3-diyl)bis(methylene)bis(3-(trifluoromethyl)benzoate)
[5] (8-methyl-4-oxothiochroman-3,3-diyl)bis(methylene)bis(3-(trifluoromethyl)benzoate)
[6] (8-methyl-4-oxothiochroman-3,3-diyl)bis(methylene)bis(2-(trifluoromethyl)benzoate)
[7] (6,8-dimethyl-4-oxothiochroman-3,3-diyl)bis(methylene)bis(4-tert-butylbenzenesulfonate)
[8] 4-tert-butylbenzenesulfonic acid 3-hydroxymethyl-4-oxo-thiochroman-3-ylmethyl ester
[9] (8-methyl-4-oxothiochroman-3,3-diyl)bis(methylene)bis(4-tert-butylbenzenesulfonate)
[10] (6,8-dimethyl-4-oxothiochroman-3,3-diyl)bis(methylene)bis(3-(trifluoromethyl)benzoate)
[11] (6-fluoro-4-oxothiochroman-3,3-diyl)bis(methylene)bis(3-(trifluoromethyl)benzoate)
[12] (6,8-dimethyl-4-oxothiochroman-3,3-diyl)bis(methylene)bis(2-(trifluoromethyl)benzoate)
[13] 4-tert-butylbenzenesulfonic acid 3-hydroxymethyl-8-methyl-4-oxo-thiochroman-3-ylmethyl ester
[14] (8-chloro-4-oxothiochroman-3,3-diyl)bis(methylene)bis(2-(trifluoromethyl)phenylcarbamate)
[15] (6-fluoro-4-oxothiochroman-3,3-diyl)bis(methylene)bis(2-(trifluoromethyl)benzoate)
[16] 2-trifluoromethylbenzoic acid 6-fluoro-3-hydroxymethyl-4-oxo-thiochroman-3-ylmethyl ester
[17] (6-fluoro-4-oxothiochroman-3,3-diyl)bis(methylene)bis(4-tert-butylbenzenesulfonate)
[18] 4-tert-butylbenzenesulfonic acid 6-fluoro-3-hydroxymethyl-4-oxo-thiochroman-3-ylmethyl ester
[19] 4-tert-butylbenzenesulfonic acid 8-chloro-3-hydroxymethyl-4-oxo-thiochroman-3-ylmethyl ester
[20] (8-chloro-4-oxothiochroman-3,3-diyl)bis(methylene)bis(3-(trifluoromethyl)-phenylcarbamate)
[21] 2-trifluoromethylbenzoic acid 8-chloro-3-hydroxymethyl-4-oxo-thiochroman-3-ylmethyl ester
[22] (5-methyl-4-oxothiochroman-3,3-diyl)bis(methylene)bis(4-tert-butylbenzenesulfonate)
[23] 2-trifluoromethylbenzoic acid 3-hydroxymethyl-6-methoxy-4-oxo-thiochroman-3-ylmethyl ester
[24] (7,8-dichloro-4-oxothiochroman-3,3-diyl)bis(methylene)bis(4-tert-butylbenzenesulfonate)
[25] (6-methoxy-4-oxothiochroman-3,3-diyl)bis(methylene)bis(4-tert-butylbenzenesulfonate)
[26] (8-chloro-4-oxothiochroman-3,3-diyl)bis(methylene)bis(2-(trifluoromethyl)benzoate)
[27] (5-methyl-4-oxothiochroman-3,3-diyl)bis(methylene)bis(2-(trifluoromethyl)phenylcarbamate)
[28] (5-methyl-4-oxothiochroman-3,3-diyl)bis(methylene)bis(3-(trifluoromethyl)phenylcarbamate)
[29] (7,8-dichloro-4-oxothiochroman-3,3-diyl)bis(methylene)bis(3-(trifluoromethyl)phenylcarbamate)
[30] (6-fluoro-4-oxothiochroman-3,3-diyl)bis(methylene)bis(3-(trifluoromethyl)phenylcarbamate)
[31] (7,8-dichloro-4-oxothiochroman-3,3-diyl)bis(methylene)bis(2-(trifluoromethyl)phenylcarbamate)
[32] 2-trifluoromethylbenzoic acid 3-hydroxymethyl-5-methyl-4-oxo-thiochroman-3-ylmethyl ester
[33] (5-methyl-4-oxothiochroman-3,3-diyl)bis(methylene)bis(3-(trifluoromethyl)benzoate)
[34] 3-trifluoromethylbenzoic acid 3-hydroxymethyl-5-methyl-4-oxo-thiochroman-3-ylmethyl ester
[35] (5-methyl-4-oxothiochroman-3,3-diyl)bis(methylene)bis(2-(trifluoromethyl)benzoate)
[36] 3,3-bis(4-tert-butylbenzenesulfonyloxymethyl)-5-methyl-1,1-dioxo-1λ$^6$-thiochroman-4-one
[37] 3,3-bis(3-trifluoromethylphenylcarbamoyloxymethyl)-5-methyl-1,1-dioxo-1λ$^6$-thiochroman-4-one
[38] bis(4-chlorophenyl)(4-oxothiochroman-3,3-diyl)bis(methylene)-dicarbonate
[39] (7-methyl-4-oxothiochroman-3,3-diyl)bis(methylene)bis(phenyl-carbamate)
[40] (5-methyl-4-oxothiochroman-3,3-diyl)bis(methylene)bis(phenyl-carbamate)
[41] 3,3-bis(phenylcarbamoyloxymethyl)thiochroman-4-one
[42] 3,3-bis(4-methoxyphenylcarbamoyloxymethyl)thiochroman-4-one

[43] 3,3-bis(phenylcarbamoyloxymethyl)-1,1-dioxo-1$\lambda^6$-thiochroman-4-one
[44] 3,3-bis(phenylcarbamoyloxymethyl)-1-oxo-1$\lambda^4$-thiochroman-4-one
[45] 3,3-bis(phenylcarbamoyloxymethyl)-5-methyl-1-oxo-1$\lambda^4$-thiochroman-4-one
[46] 3,3-bis(phenylcarbamoyloxymethyl)-5-methyl-1,1-dioxo-1$\lambda^6$-thiochroman-4-one
[47] 3,3-bis(phenylcarbamoyloxymethyl)-7-methyl-1-oxo-1$\lambda^4$-thiochroman-4-one
[48] 3,3-bis(phenylcarbamoyloxymethyl)-7-methyl-1,1-dioxo-1$\lambda^6$-thiochroman-4-one
[49] phenylcarbamic acid 3-methoxymethyl-4-oxothiochroman-3-ylmethyl ester
[50] 3,3-bis(4-tert-butylphenylcarbamoyloxymethyl)thiochroman-4-one
[51] 3,3-bis(2-tert-butylphenylcarbamoyloxymethyl)thiochroman-4-one
[52] 3,3-bis(4-trifluoromethylphenylcarbamoyloxymethyl)thiochroman-4-one
[53] 3,3-bis(2-trifluoromethylphenylcarbamoyloxymethyl)thiochroman-4-one
[54] 3,3-bis(3-trifluoromethylphenylcarbamoyloxymethyl)thiochroman-4-one
[55] phenylcarbamic acid 4-oxothiochroman-3-ylmethyl ester, and
[56] bis(3-trifluoromethyl)(4-oxothiochroman-3,3-diyl)bis(methylene)-dicarbonate;

in each case, as appropriate, in the form of one of its pure stereoisomers, especially enantiomers or diastereomers, of its racemates or in the form of a mixture of stereoisomers, especially of the enantiomers and/or diastereomers, in any mixing ratio, or in each case in the form of corresponding salts, or in each case in the form of corresponding solvates.

14. A pharmaceutical composition comprising a compound as claimed in claim 1, including the excluded compounds and one or more physiologically compatible excipients.

15. A pharmaceutical composition comprising
[1] (4-oxothiochroman-3,3-diyl)bis(methylene)bis(3-(trifluoromethyl)benzoate;

as appropriate, in the form of one of its pure stereoisomers, especially enantiomers or diastereomers, of its racemates or in the form of a mixture of stereoisomers, especially of the enantiomers and/or diastereomers, in any mixing ratio, or in each case in the form of corresponding salts, or in each case in the form of corresponding solvates.

* * * * *